US011110150B2

(12) United States Patent
Felber et al.

(10) Patent No.: US 11,110,150 B2
(45) Date of Patent: Sep. 7, 2021

(54) COMPLEXES OF IL-15 AND IL-15RALPHA AND USES THEREOF

(71) Applicants: NOVARTIS AG, Basel (CH); The United States of America, as Represented by the Secretary, Department of Health and Human Services, Bethesda, MD (US)

(72) Inventors: Barbara K. Felber, Rockville, MD (US); Sergio Finkielsztein, Newton, MA (US); George N. Pavlakis, Bethesda, MD (US); John V. Vournakis, Charleston, SC (US)

(73) Assignees: NOVARTIS AG, Basel (CH); The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/291,561

(22) Filed: Mar. 4, 2019

(65) Prior Publication Data

US 2019/0290734 A1    Sep. 26, 2019

Related U.S. Application Data

(63) Continuation of application No. 15/424,621, filed on Feb. 3, 2017, now Pat. No. 10,265,382, which is a continuation of application No. 12/666,052, filed as application No. PCT/US2008/008084 on Jun. 27, 2008, now Pat. No. 9,931,377.

(60) Provisional application No. 60/937,471, filed on Jun. 27, 2007.

(51) Int. Cl.
| | | |
|---|---|---|
| C12N 15/85 | (2006.01) | |
| A61K 38/20 | (2006.01) | |
| A61K 39/00 | (2006.01) | |
| A61K 38/17 | (2006.01) | |
| A61K 35/13 | (2015.01) | |
| A61K 47/36 | (2006.01) | |
| C07K 16/24 | (2006.01) | |
| C07K 16/28 | (2006.01) | |
| C12N 5/071 | (2010.01) | |

(52) U.S. Cl.
CPC .......... *A61K 38/2086* (2013.01); *A61K 35/13* (2013.01); *A61K 38/1793* (2013.01); *A61K 39/0011* (2013.01); *A61K 39/00114* (2018.08); *A61K 47/36* (2013.01); *C07K 16/244* (2013.01); *C07K 16/2866* (2013.01); *C12N 5/0686* (2013.01); *C12N 15/85* (2013.01); *A61K 2039/5152* (2013.01); *A61K 2039/5156* (2013.01); *A61K 2039/55527* (2013.01); *C07K 2317/24* (2013.01); *C07K 2317/76* (2013.01); *C12N 2500/90* (2013.01); *C12N 2510/00* (2013.01)

(58) Field of Classification Search
CPC .................................................. C12N 15/85
See application file for complete search history.

(56) References Cited

U.S. PATENT DOCUMENTS

| | | | |
|---|---|---|---|
| 5,552,303 A | 9/1996 | Grabstein et al. | |
| 5,574,138 A | 11/1996 | Grabstein et al. | |
| 5,965,726 A | 10/1999 | Pavlakis et al. | |
| 5,972,596 A | 10/1999 | Pavlakis et al. | |
| 6,001,973 A | 12/1999 | Strom et al. | |
| 6,063,911 A | 5/2000 | Vournalds et al. | |
| 6,174,666 B1 | 1/2001 | Pavlakis et al. | |
| 6,291,664 B1 | 9/2001 | Pavlakis et al. | |
| 6,414,132 B1 | 7/2002 | Pavlakis et al. | |
| 6,451,308 B1 | 9/2002 | Strom et al. | |
| 6,548,065 B1 | 4/2003 | Anderson et al. | |
| 6,764,836 B2 | 7/2004 | Anderson et al. | |
| 6,787,132 B1 | 9/2004 | Gabizon | |
| 6,794,498 B2 | 9/2004 | Pavlakis et al. | |
| 6,864,245 B2 | 3/2005 | Vournakis et al. | |
| 6,998,476 B2 | 2/2006 | Strom et al. | |
| 7,067,132 B2 | 6/2006 | Grabstein et al. | |
| 7,112,436 B1 | 9/2006 | Rose-John et al. | |
| 7,258,853 B2 | 8/2007 | Strom et al. | |
| 7,435,596 B2 | 10/2008 | Campana et al. | |
| 7,638,604 B2 | 12/2009 | Li et al. | |
| 7,858,081 B2 | 12/2010 | Bernard et al. | |
| 8,124,084 B2 | 2/2012 | Lefrancois et al. | |
| 8,163,879 B2 | 4/2012 | Wong et al. | |

(Continued)

FOREIGN PATENT DOCUMENTS

| | | |
|---|---|---|
| CA | 2625694 | 4/2007 |
| EP | 1777294 | 4/2007 |

(Continued)

OTHER PUBLICATIONS

Alpdogan et al., 2005, IL-7 and IL-15: therapeutic cytokines for immunodeficiency, Trends Immunol., 26:56-64.

(Continued)

*Primary Examiner* — Prema M Mertz
(74) *Attorney, Agent, or Firm* — Yichen Liu

(57) ABSTRACT

The present invention relates to agents that modulate interleukin-15 ("IL-15") signal transduction or function ("Therapeutic Agents") and the use ol" those agents to modulate immune function. The Therapeutic Agents target the interaction between IL-15 and its receptor and modulate IL-15-induced signal transduction. The Therapeutic Agents may be formulated with polymers, such as poly-β-1-♦4-N-acetyl-glucosamine. for administration to a human subject to modulate IL-15-mediated immune function.

4 Claims, 15 Drawing Sheets

Figure 4C:
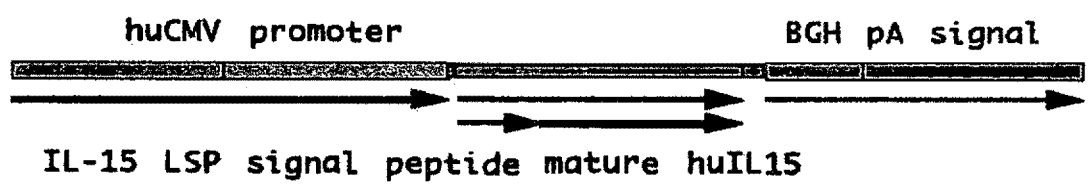

Specification includes a Sequence Listing.

(56) References Cited

U.S. PATENT DOCUMENTS

| | | | |
|---|---|---|---|
| 8,224,578 | B2 | 7/2012 | Raab et al. |
| 8,492,118 | B2 | 7/2013 | Wong et al. |
| 8,507,222 | B2 | 8/2013 | Wong et al. |
| 8,940,288 | B2 | 1/2015 | Lefrancois et al. |
| 2002/0022030 | A1 | 2/2002 | Marrack et al. |
| 2002/0127201 | A1 | 9/2002 | Boussiotis et al. |
| 2002/0182178 | A1 | 12/2002 | Grooten et al. |
| 2003/0105295 | A1 | 6/2003 | Strom et al. |
| 2004/0087015 | A1 | 5/2004 | Vournalds et al. |
| 2004/0170604 | A1 | 9/2004 | Ekida et al. |
| 2004/0253587 | A1 | 12/2004 | Grabstein et al. |
| 2005/0032167 | A1 | 2/2005 | Anderson et al. |
| 2005/0042220 | A1 | 2/2005 | Li et al. |
| 2006/0057680 | A1 | 3/2006 | Zheng et al. |
| 2006/0093605 | A1 | 5/2006 | Campana et al. |
| 2006/0104945 | A1 | 5/2006 | Choi |
| 2006/0147419 | A1 | 7/2006 | Perera et al. |
| 2006/0165668 | A1 | 7/2006 | Liu et al. |
| 2006/0257361 | A1 | 11/2006 | Watanabe et al. |
| 2006/0263857 | A1 | 11/2006 | Lefrancois et al. |
| 2007/0110714 | A1 | 5/2007 | Hayashi |
| 2007/0134718 | A1 | 6/2007 | Grooten et al. |
| 2007/0141557 | A1 | 6/2007 | Raab et al. |
| 2007/0160578 | A1 | 7/2007 | Waldmann et al. |
| 2008/0255039 | A1 | 10/2008 | Bernard et al. |
| 2009/0082299 | A1 | 3/2009 | Felber et al. |
| 2009/0238791 | A1 | 9/2009 | Jacques et al. |
| 2009/0324538 | A1 | 12/2009 | Wong et al. |
| 2011/0081311 | A1 | 4/2011 | Pavlakis et al. |
| 2011/0158938 | A1 | 6/2011 | Bernard et al. |
| 2012/0177598 | A1 | 7/2012 | Lefrancois et al. |
| 2012/0230946 | A1 | 9/2012 | Wong et al. |
| 2014/0134128 | A1 | 5/2014 | Wong et al. |

FOREIGN PATENT DOCUMENTS

| | | |
|---|---|---|
| JP | A-S62-205784 | 9/1987 |
| JP | A-H7-255470 | 10/1995 |
| JP | 2008-520250 A | 6/2008 |
| WO | WO 1995/027722 A1 | 10/1995 |
| WO | WO 1995/030695 A1 | 11/1995 |
| WO | WO 1996/037223 A1 | 11/1996 |
| WO | WO 1997/041232 A1 | 11/1997 |
| WO | WO 1998/036768 A1 | 8/1998 |
| WO | WO 00/36918 | 6/2000 |
| WO | WO 2001/080889 A1 | 11/2001 |
| WO | WO 2002/022805 A2 | 3/2002 |
| WO | WO 2003/092737 | 11/2003 |
| WO | WO 2004/059556 A2 | 7/2004 |
| WO | WO 2005/085282 A1 | 9/2005 |
| WO | WO 2006/020849 A2 | 2/2006 |
| WO | 2006/055915 A2 | 5/2006 |
| WO | WO 2006/089064 | 8/2006 |
| WO | WO 2007/001677 A2 | 1/2007 |
| WO | WO 2007/046006 A2 | 4/2007 |
| WO | WO 2007/084342 A2 | 7/2007 |
| WO | WO 2007/095643 A2 | 8/2007 |
| WO | WO 2008/089144 A2 | 7/2008 |
| WO | WO 2008/143794 A1 | 11/2008 |
| WO | 2009/002562 A2 | 12/2008 |
| WO | WO 2011/020047 A1 | 2/2011 |
| WO | WO 2012/040323 A2 | 3/2012 |
| WO | WO 2012/175222 A1 | 12/2012 |

OTHER PUBLICATIONS

Alpdogan et al., 2005, "Interleukin-15 enhances immune reconstitution after allogeneic bone marrow transplantation," Blood 105, 865-873.

Altman et al., 1996, "Phenotypic analysis of antigen-specific T lymphocytes," Science, 274:94-96.

Anderson et al., 1995, "Functional characterization of the human interleukin-15 receptor alpha chain and close linkage of IL15RA and IL2RA genes," J. Biol. Chem., 270(50):29862-29869.

Armitage et al., 1995, "IL-15 has stimulatory activity for the induction of B cell proliferation and differentiation," J. Immunol., 154:483-490.

Ausubel et al., 1993, Current Protocols in Molecular Biology, John Wiley & Sons, pp. 2.10.1-2.10.16.

Baccala et al., 2005, "Tumor immunity via homeostatic T cell proliferation: mechanistic aspects and clinical perspectives," Springer Semin Immunopathol; 27:75-85.

Badoual et al., "The soluble alpha chain of interleukin-15 receptor: a proinflammatory molecule associated with tumor progression in head and neck cancer," Cancer Res., 2008, 68(10):3907-14.

Bamford et al., 1994, "The interleukin (IL) 2 receptor beta chain is shared by IL-2 and a cytokine, provisionally designated IL-T, that stimulates T-cell proliferation and the induction of lymphokine-activated killer cells," Proc. Natl. Acad. Sci., USA 91(11):4940-4944.

Bamford et al., 1996, "Interleukin (IL) 15/IL-T production by the adult T-cell leukemia cell line HuT-102 is associated with a human T-cell lymphotrophic virus type I region /IL-15 fusion message that lacks many upstream AUGs that normally attenuates IL-15 mRNA translation," Proc. Natl. Acad. Sci. USA, 93(7):2897-2902.

Bamford et al., 1998, "The 5' untranslated region, signal peptide, and the coding sequence of the carboxyl terminus of IL-15 participate in its multifaceted translational control," J Immunol., 160(9):4418-4426.

Becker et al., 2002, "Interleukin 15 is required for proliferative renewal of virus-specific memory CD8 T cells," J. Exp. Med., 195(12):1541-1548.

Berard et al., 2003, "IL-15 promotes the survival of naive and memory phenotype CD8+ T cells," J. Immunol., 170(10):5018-5026.

Berger et al., 2009, "Safety and immunologic effects of IL-15 administration in nonhuman primates", Blood; 114:2417-2426.

Bernard et al., 2004, "Identification of an interleukin-15α receptor-binding site on human interleukin-15," J Biol Chem., vol. 279:24313-24322.

Bindon et al., 1983, "Clearance rates and systemic effects of intravenously administered interleukin 2 (IL-2) containing preparations in human subjects," Br. J. Cancer, 47:123-133.

Brocker, 1997, "Survival of mature CD4 T lymphocytes is dependent on major histocompatibility complex class II-expressing dendritic cells," J. Exp. Med., 186:1223-1232.

Budagian et al., 2004, "Reverse signaling through membrane-bound interleukin-15," J. Biol. Chem., 279:42192-42201.

Burkett et al., 2003, "IL-15R alpha expression on CD8+ T cells is dispensable for T cell memory," Proc. Natl. Acad. Sci. USA, 100:4724-4729.

Burkett et al., 2004, "Coordinate expression and trans presentation of interleukin (IL)-15Ralpha and IL-15 supports natural killer cell and memory CD8+ T cell homeostasis," J. Exp. Med., 200:825-834.

Burton et al., 1994, "A lymphokine, provisionally designated interleukin T and produced by a human adult T-cell leukemia line, stimulates T-cell proliferation and the induction of lymphokine-activated killer cells," Proc. Natl. Acad. Sci. USA, 91(11):4935-4939.

Carson et al., 1994, "Interleukin (IL) 15 is a novel cytokine that activates human natural killer cells via components of the IL-2 receptor," J Exp. Med., 180:1395-1403.

Castelli et al., 2004, "Mature dendritic cells can enhance CD8+ cell noncytotoxic anti-HIV responses: the role of IL-15," Blood, 103:2699-2704.

Chapoval et al., 1998, "Combination chemotherapy and IL-15 administration induce permanent tumor regression in a mouse lung tumor model: NK and T cell-mediated effects antagonized by B cells," J Immunol., 161:6977-6984.

Chehimi et al., 1997, "IL-15 enhances immune functions during HIV infection", J Immunol; 158(12):5978-5987.

Chitnis et al., 2003, "Determinants of HIV-specific CD8 T-cell responses in HIV-infected pediatric patients and enhancement of HIV-gag-specific responses with exogenous IL-15," Clin Immunol., 107:36-45.

(56) References Cited

OTHER PUBLICATIONS

Cho et al., 2000, "Homeostasis-stimulated proliferation drives naive T cells to differentiate directly into memory T cells," J. Exp. Med., 192:549-556.
Cooper et al., 2002, "In vivo evidence for a dependence on interleukin 15 for survival of natural killer cells," Blood, 100:3633-3638.
Davis et al., 1991, "Reduction of Immunogenicity and Extension of Circulating Half-life of Peptides and Proteins," Peptide and Protein Drug Delivery, Marcel Deker Inc., New York, pp. 831-864.
De Jong et al., 1996, "Interaction of IL-15 with the shared IL-2 receptor beta and gamma c subunits. The IL-15/beta/gamma c receptor-ligand complex is less stable than the IL-2/beta/gamma c receptor-ligand complex," J. Immunol., 156:1339-1348.
Dubois et al., 1999, "Natural splicing of exon 2 of human interleukin-15 receptor α-chain mRNA results in a shortened form with a distinct pattern of expression," J Biol Chem, vol. 274:26978-26984.
Dubois et al., 2002, "IL-15Ralpha recycles and presents IL-15 in trans to neighboring cells," Immunity, 17:537-547.
Dudley et al., 2005, "Adoptive cell transfer therapy following non-myeloablative but lymphodepleting chemotherapy for the treatment of patients with refractory metastatic melanoma," J. Clin. Oncol., 23:2346-2357.
Dummer et al., 2002, "T cell homeostatic proliferation elicits effective antitumor autoimmunity," J. Clin. Invest, 110:185-192.
Dunne et al., 2001, "Selective expansion and partial activation of human NK cells and NK receptor-positive T cells by IL-2 and IL-15," J. Immunol., 167:3129-3138.
EMBL Database accession No. BC074726, "*Homo sapiens* interleukin 15 receptor, alpha, transcript variant 1, m Rna (cDNA clone MGC:103798 Image:30915179), complete cds", dated Aug. 4, 2004.
Epardaud et al., 2008, "Interleukin-15/interleukin-15Rα complexes promote destruction of established tumors by reviving tumor-resident CD8+ T cells," Cancer Res., vol. 68:2972-2983.
Fehniger et al., 2001, "Interleukin 15: biology and relevance to human disease," Blood, vol. 97:14-32.
Ferrari-Lacraz et al., 2004, "Targeting IL-15 receptor-bearing cells with an antagonist mutant IL-15/Fc protein prevents disease development and progression in murine collagen-induced arthritis," J. Immunol., 173:5818-5826.
Fewkes et al., 2010, "Novel gamma-chain cytokines as candidate immune modulators in immune therapies for cancer", J Cancer; 16:392-398.
Fischer et al., "A bioactive designer cytokine for human hematopoietic progenitor cell expansion," Nat. Biotechnol., 1997, 15(2):142-145.
Forcina et al., 2004, "Interleukin-15 modulates interferon-gamma and beta-chemokine production in patients with HIV infection: implications for immune-based therapy," Cytokine, 25:283-290.
Giri et al., 1994, "Utilization of the beta and gamma chains of the IL-2 receptor by the novel cytokine IL-15," EMBO J., 13(12):2822-2830.
Giri et al., 1995, "Identification and cloning of a novel IL-15 binding protein that is structurally related to the alpha chain of the IL-2 receptor," EMBO J., 14(15):3654-3663.
Giri et al., 1995, "IL-15, a novel T cell growth factor that shares activities and receptor components with IL-2," J. Leukocyte Biol., 57:763-766.
Giron-Michel et al., 2005, "Membrane-bound and soluble IL-15/IL-15Rα complexes display differential signaling and functions on human hematopoietic progenitors," Blood, vol. 106:2302-2310.
Goldrath et al., 2000, "Low-affinity ligands for the TCR drive proliferation of mature CD8+ T cells in lymphopenic hosts," Immunity, 11(2):183-190.
Goldrath et al., 2002, "Cytokine requirements for acute and Basal homeostatic proliferation of naive and memory CD8+ T cells," J. Exp. Med., 195(12):1515-1522.
Grabstein et al., 1994, "Cloning of a T cell growth factor that interacts with the beta chain of the interleukin-2 receptor," Science, 264:965-968.

Hsu et al., 2005, "Primary human T lymphocytes engineered with a codon-optimized IL-15 gene resist cytokine withdrawal-induced apoptosis and persist long-term in the absence of exogenous cytokine", J Immunol; 175:7226-7234.
International Search Report of International application No. PCT/US08/08084, dated Dec. 30, 2008.
Judge et al., 2002, "Interleukin 15 controls both proliferation and survival of a subset of memory-phenotype CD8(+) T cells," J. Exp. Med., 196:935-946.
Jung et al., 2002, "In vivo depletion of CD11c+ dendritic cells abrogates printing of CD8+ T cells by exogenous cell-associated antigens," Immunity, 17:211-220.
Kassiotis et al., 2002, "Impairment of immunological memory in the absence of MHC despite survival of memory T cells," Nat. Immunol., 3:244-250.
Kennedy et al., 2000, "Reversible defects in natural killer and memory CD8 T cell lineages in interleukin 15-deficient mice," J. Exp. Med., 191:771-780.
Khan et al., 1996, IL-15 augments CD8+ T cell-mediated immunity against Toxoplasma gondii infection in mice, J. Immunol., 157(2):2103-2108.
Khan et al., 2002, "Treatment with soluble interleukin-15R alpha exacerbates intracellular parasitic infection by blocking the development of memory CD8+ T cell response", J Exp Med; 195(11):1463-1470.
Kieper et al., 2000, Homeostatic expansion and phenotypic conversion of naïve T cells in response to self peptide/MHC ligands, Proc Natl. Acad. Sci. USA., 96(23):13306-13311.
Kim et al., 1998, "Generation of mucosal cytotoxic T cells against soluble protein by tissue-specific environmental and costimulatory signals," Proc Natl. Acad. Sci. USA, 95:10814-10819.
Kishimoto et al., 2010, "IL-6: from its discovery to clinical applications", International Immunology; 22(5):347-352.
Klebanoff et al., 2004, "IL-15 enhances the in vivo antitumor activity of tumor-reactive CD8+ T cells," Proc. Natl. Acad. Sci. USA, 101(7):1969-1974.
Kobayashi et al., 2000, "Differences of biodistribution, pharmacokinetics, and tumor targeting between interleukins 2 and 15," Cancer Res., 60(13):3577-3583.
Koka et al., 2003, "Interleukin (IL)-15R[alpha]deficient natural killer cells survive in normal but not IL-15R[alpha]-deficient mice," J. Exp. Med. 197:977-984.
Ku et al., 2000, "Control of homeostasis of CD8+ memory T cells by opposing cytokines," Science, 288:675-678.
Kutzler et al., 2005, "Coimmunization with an optimized IL-15 plasmid results in enhanced function and longevity of CD8 T cells that are partially independent of CD4 T cell help," Immunol., vol. 175:112-123.
Lodolce et al., 1998, "IL-15 receptor maintains lymphoid homeostasis by supporting lymphocyte homing and proliferation," Immunity, 9:669-676.
Lodolce et al., 2001, "T cell-independent interleukin 15Ralpha signals are required for bystander proliferation," J. Exp. Med., 194:1187-1193.
Lum et al., 2004, "Differential effects of interleukin-7 and interleukin-15 on NK cell anti-human immunodeficiency virus activity," J. Virol., 78:6033-6042.
Maeurer et al., 2000, "Interleukin-7 or interleukin-15 enhances survival of Mycobacterium tuberculosis-infected mice," Infect. Immun. 68:2962-2970.
Masopust et al., 2001, "Direct analysis of the dynamics of the intestinal mucosa CD8 T cell response to systemic virus infection," J. Immunol., 166:2348-2356.
Mastroianni et al., 2000, "Interleukin-15 enhances neutrophil functional activity in patients with human immunodeficiency virus infection," Blood, 96:1979-1984.
Matsumoto et al., "On-column refolding and characterization of soluble human interleukin-15 receptor alpha-chain produced in *Escherichia coli*," Protein Expr. Purif., 2003, 31(1):64-71.
Mortier et al., 2004, "Natural, proteolytic release of a soluble form of human IL-15 receptor α-chain that behaves as a specific, high affinity IL-15 antagonist," J of Immunol., vol. 173:1681-1688.

(56) References Cited

OTHER PUBLICATIONS

Mortier et al., 2006, "Soluble interleukin-15 receptor α(IL-15Rα)-sushi as a selective and potent agonist of IL-15 action through IL-15R β/γ. Hyperagonist IL-15 x IL-15Rα fusion proteins," J Biol Chem., vol. 281:1612-1619.
Mueller et al., 2003, "IL-15 enhances survival and function of HIV-specific CD8+ T cells," Blood, 101(3):1024-1029.
Murali-Krishna et al., 1999, "Persistence of memory CD8 T cells in MHC class I-deficient mice," Science, 286:1377-1381.
Nguyen et al., 2000, "TNF receptor 1 (TNFR1) and CD95 are not required for T cell deletion after virus infection but contribute to peptide-induced deletion under limited conditions," Eur. J. Immunol., 30:683-688.
Nishimura et al., 2005, "A novel autoregulatory mechanism for transcriptional activation of the IL-15 gene by a nonsecretable isoform of IL-15 generated by alternative splicing," FASEB J., 19:19-28.
Oehen et al., 1998, "Differentiation of naive CTL to effector and memory CTL: correlation of effector function with phenotype and cell division," J. Immunol., 161:5338-5346.
Oh et al., 2003, "Coadministration of HIV vaccine vectors with vaccinia viruses expressing IL-15 but not IL-2 induces long-lasting cellular immunity," Proc. Natl. Acad. Sci. USA, 100(6):3392-3397.
Oh et al., 2004, "IL-15/IL-15Ralpha-mediated avidity maturation of memory CD8+ T cells," Proc. Natl. Acad. Sci. USA, 101(42):15154-15159.
Ohteki et al., 2001, "Critical role of IL-15-IL-15R for antigen-presenting cell functions in the innate immune response," Nat. Immunol., 2:1138-1143.
Park et al., 2004, "Follicular dendritic cells produce IL-15 that enhances germinal center B cell proliferation in membrane-bound form," J. Immunol., 173:6676-6683.
PCT International Search Report, International Application No. PCT/US06/19403, dated May 11, 2007.
Pettit et al., 1997, "Structure-function studies of interleukin 15 using site-specific mutagenesis, polyethylene glycol conjugation, and homology modeling", J Biol Chem; 272(4):2312-2318.
Pflanz et al., "A fusion protein of interleukin-11 and soluble interleukin-11 receptor acts as a superagonist on cells expressing gp130," FESB Lett., 1999, 450:117-122.
Porter et al., 2005, "T-cell reconstitution and expansion after hematopoietic stem cell transplantation: 'T' it up!," Bone Marrow Transplant, 35(10):935-942.
Prlic et al., 2003, "In vivo survival and homeostatic proliferation of natural killer cells," J. Exp. Med., 197:967-976.
Jalah et al., 2007, "Efficient systemic expression of bioactive IL-15 in mice upon delivery of optimized DNA expression plasmids", DNA and Cell Biology; 26(12):827-840.
Roychowdhury et al., 2004, "Failed adoptive immunotherapy with tumor-specific T cells: reversal with low-dose interleukin 15 but not low-dose interleukin 2," Cancer Res., 64:8062-8067.
Rubinstein et al., 2006, "Converting IL-15 to a superagonist by binding to soluble IL-15Rα," PNAS, vol. 103(24):9166-9171.
Rubinstein et al., 2002, "Systemic administration of IL-15 augments the antigen-specific primary CD8+ T cell response following vaccination with peptide-pulsed dendritic cells," J. Immunol., 169:4928-4935.
Ruchatz et al., 1998, "Soluble IL-15 receptor alpha-chain administration prevents murine collagen-induced arthritis: a role for IL-15 in development of antigen-induced immunopathology," J. Immunol., 160:5654-5660.
Ruckert et al., 2003, "Dendritic cell-derived IL-15 controls the induction of CD8 T cell immune responses," Eur. J. Immunol., 33:3493-3503.
Sandau et al., 2004, "Cutting edge: transpresentation of IL-15 by bone marrow-derived cells necessitates expression of IL-15 and IL-15R alpha by the same cells," J. Immunol., 173:6537-6541.
Sato et al., 2007, "The IL-15/IL-15Ralpha on cell surfaces enables sustained I-15 activity and contributes to the long survival of CD8 memory T cells." Proc. Natl. Acad. Sci. 104(2):588-593.

Schluns et al., 2000, "Interleukin-7 mediates the homeostasis of naïve and memory CD8 T cells in vivo," Nat. Immunol., 1:426-432.
Schluns et al., 2002, "Cutting edge: requirement for IL-15 in the generation of primary and memory antigen-specific CD8 T cells," J. Immunol., 168:4827-4831.
Schluns et al., 2004, "Distinct cell types control lymphoid subset development by means of IL-15 and IL-15 receptor alpha expression," Proc. Natl. Acad. Sci. USA, 101(15):5616-5621.
Schluns et al., 2004, "Transregulation of memory CD8 T-cell proliferation by IL-15Ralpha+ bone marrow-derived cells," Blood; 103(3):988-994.
Schluns et al., 2005, "The roles of interleukin-15 receptor α:Transpresentation, receptor component, or both?" Int J Biochem Cell Biol., vol. 37:1567-1571.
Smith et al., 2000, "Selective blockade of IL-15 by soluble IL-15 receptor alpha-chain enhances cardiac allograft survival," J. Immunol., 165(6):3444-3450.
Stoklasek et al., 2006, "Combined IL-15/IL-15Rα immunotherapy maximizes IL-15 activity in vivo,", J of Immunol., vol. 177(9):6072-6080.
Tan et al., 2002, "Interleukin (IL)-15 and IL-7 jointly regulate homeostatic proliferation of memory phenotype CD8+ cells but are not required for memory phenotype CD4+ cells," J. Exp. Med., 195:1523-1532.
Tsunobuchi et al., 2000, "A protective role of interleukin-15 in a mouse model for systemic infection with herpes simplex virus," Virology, 275:57-66.
Umemura et al., 2001, "Overexpression of IL-15 in vivo enhances protection against Mycobacterium bovis bacillus Calmette-Guérin infection via augmentation of NK and T cytotoxic 1 responses," J. Immunol., 167:946-956.
Van Belle et al., 2005, "IL-15 and IL-15Rα in CD4+ T cell immunity," Arch Immunol Ther Exp., vol. 53:115-126.
Villinger et al., 2004, "IL-15 is superior to IL-2 in the generation of long-lived antigen specific memory CD4 and CD8 T cells in rhesus macaques," Vaccine, 22:3510-3521.
Waldmann et al., 1999, "The multifaceted regulation of interleukin-15 expression and the role of this cytokine in NK cell differentiation and host response to intracellular pathogens," Annu Rev Immunol., vol. 17:19-49.
Waldmann et al., 2001, "Contrasting roles of IL-2 and IL-15 in the life and death of lymphocytes: implications for immunotherapy," Immunity, vol. 14:105-110.
Waldmann, T.A., 2006, "The biology of interleukin-2 and interleukin-15: implications for cancer therapy and vaccine design," Nat Rev Immunol., vol. 6:595-601.
Wang et al., 1987, "The interleukin 2 receptor. Functional consequences of its bimolecular structure," J. Exp. Med., 166(4):1055-1069.
Warren et al., 1996, "Analysis of the costimulatory role of IL-2 and IL-15 in initiating proliferation of resting (CD56dim) human NK cells," J. Immunol., 156:3254-3259.
Wei et al., 2001, "The Sushi domain of soluble IL-15 receptor α is essential for binding IL-15 and inhibiting inflammatory and allogenic responses in vitro and in vivo," J Immunol., vol. 167:277-282.
Williams et al., 2007, "T cell immune reconstitution following lymphodepletion", Seminars in Immunology; 19(5):318-330.
Written Opinion of International application No. PCT/US08/08084, dated Dec. 30, 2008.
Wrzesinski et al., 2005, "Less is more: lymphodepletion followed by hematopoietic stem cell transplant augments adoptive T-cell-based anti-tumor immunotherapy," Curr. Opin. Immunol., 17:195-201.
Wysocka et al., 2004, "Enhancement of the host immune responses in cutaneous T-cell lymphoma by CpG oligodeoxynucleotides and IL-15," Blood, 104:4142-4149.
Zeng et al., 2005, "Synergy of IL-21 and IL-15 in regulating CD8+ T cell expansion and function," J. Exp. Med., 201:139-148.
Scheller et al., 2006, "Interleukin-6 and its receptor: from bench to bedside", Med Microbiol Immunol; 195:173-183.
Johnston et al., 1995, Tyrosine phosphorylation and activation of STAT5, STAT3, and Janus kinases by interleukins 2 and 15. Proc Natl Acad Sci U S A. 92(19):8705-9.

(56) References Cited

OTHER PUBLICATIONS

Krause et al., 1996, Genomic structure and chromosomal localization of the human interleukin 15 gene (IL-15). Cytokine. 8(9):667-74.
Lyons et al., 1994, Determination of lymphocyte division by flow cytometry. J Immunol Methods. 2;171(1):131-7.
Pereno et al., 2000, IL-15/IL-15Ralpha intracellular trafficking in human melanoma cells and signal transduction through the IL-15Ralpha. Oncogene. 19(45):5153-62.
Zammit et al., 2005, Dendritic cells maximize the memory CD8 T cell response to infection. Immunity. 22(5):561-70.
Barzegar et al., 1998, "IL-15 is produced by a subset of human melanomas, and is involved in the regulation of markers of melanoma progression through juxtacrine loops", Oncogene; 16(19):2503-2512.
Bergamaschi et al., 2008, "Intracellular Interaction of Interleukin-15 with Its Receptor α during Production Leads to Mutual Stabilization and Increased Bioactivity", J. Biol. Chem.; 283(7):4189-4199.
European Search Report of EP application No. 13195495.0-1402, dated Mar. 28, 2014.
European Search Report of EP application No. 13195499.1-1402, dated Mar. 27, 2014.
International Preliminary Report on Patentablility of International application No. PCT/US2008/008084, dated Jan. 5, 2010.
International Search Report on International application No. PCT/US2013/066424, dated May 8, 2014.
Notice of Allowance and Fees Due of U.S. Appl. No. 11/435,497, dated Oct. 19, 2011.
Office Action of U.S. Appl. No. 11/435,497, dated Feb. 25, 2009.
Office Action of U.S. Appl. No. 11/435,497, dated Jan. 13, 2011.
Office Action of U.S. Appl. No. 11/435,497, dated Jun. 27, 2008.
Office Action of U.S. Appl. No. 11/435,497, dated Jun. 27, 2011.
Office Action of U.S. Appl. No. 11/435,497, dated Jun. 7, 2011.
Office Action of U.S. Appl. No. 11/435,497, dated Oct. 30, 2009.
Supplementary European Search Report of EP application No. 06784439.9-2401, dated Apr. 22, 2009.
Written Opinion of International application No. PCT/US2006/19403, dated May 11, 2007.
Written Opinion of International application No. PCT/US2013/066424, dated May 8, 2014.
Bergamaschi et al., 2012, "Circulating IL-15 exists as heterodimeric complex with soluble IL-15Rα in human and mouse serum", Blood, 120(1):e1-e8.
Cheever, 2008, "Twelve immunotherapy drugs that could cure cancers", Immunol Rev.; 222:357-368.
Chertova et al., 2013, "Characterization and favorable in vivo properties of heterodimeric soluble IL-15•IL-15Rα cytokine compared to IL-15 monomer", J Biol Chem, 288(25):18093-18103.
Cui et al., 2014, "Characterization of the IL-15 niche in primary and secondary lymphoid organs in vivo", Proc. Natl. Acad. Sci. USA; 111(5):1915-1920.
Dubois et al., 2008, "Preassociation of IL-15 with IL-15R alpha-IgG1-Fc enhances its activity on proliferation of NK and CD8+/CD44$^{high}$ T cells and its antitumor action", J Immunol.;180(4):2099-2106.
Jensen et al., 2012, "Structural analysis of N- and O-glycans released from glycoproteins", Nature Protocols, 7 (7): 1299-1310.
Kobayashi et al., 2005, "Role of trans-cellular IL-15 presentation in the activation of NK cell-mediated killing, which leads to enhanced tumor immunosurveillance", Blood; 105(2): 721-727.
Mlecnik et al., 2014, "Functional network pipeline reveals genetic determinants associated with in situ lymphocyte proliferation and survival of cancer patients", Sci Transl Med.; 6(228):228ra37.
Nasioulas et al., 1994, "Elements distinct from human immunodeficiency virus type 1 splice sites are responsible for the Rev dependence of env mRNA", J Virol, 68(5):2986-2993.
Rubenstein et al., 2006, "Converting IL-15 to a superagonist by binding to soluble IL-15Rα", Proc Natl Acad Sci USA, 103:24:9166-9171.
Schneider et al., 1997, Inactivation of the human immunodeficiency virus type 1 inhibitory elements allows Rev-independent expression of Gag and Gag/protease and particle formation, J Virol, 71(7):4892-4903.
Schwartz et al., 1992, "Mutational inactivation of an inhibitory sequence in human immunodeficiency virus type 1 results in Rev-independent gag expression", J Virol, 66(12):7176-7182.
Southern and Berg, 1982, "Transformation of mammalian cells to antibiotic resistance with a bacterial gene under control of the SV40 early region promoter", J Mol Appl Genet, 1:327-341.
Tagaya et al., 1997, "Generation of secretable and nonsecretable interleukin 15 isoforms through alternate usage of signal problems", Proc Natl Acad Sci USA, 94:14444-14449.
Chu et al., 2001, "Industrial choices for protein production by large-scale cell culture" *Curr Opin Biotechnol.* 12(2):180-187.
Kayukawa, K., *Biotechnology Journal* pp. 234-235, Mar. 4, 2007.
Oberg et al., Characterization of a U-937 Subline which can be Induced to Differentiate in Serum-Free Medium *Int. J. Cancer* 50:153-160, 1992.
Onu et al., "Regulation of IL-15 Secretion via the Leader peptide of Two IL-15 Isoforms" *Journal of Immunology* 158(1):255-262, 2017.
Tagaya et al., "IL-15: A Pleiotropic Cytokine with Diverse Receptor/Signaling pathways Whose Express is Controlled at Multipe Levels" *Immunity* 4:329-336, 1996.
Kazutomo Imahori, Tamio Yamakawa, Dictionary of Biochemistry (3rd Edition), Japan, published Nov. 20, 1998, Tokyo Kagaku Dojin, p. 1385.
Mikio Shikita, Kazuko Tsuneoka, GM-CSF secreted by serum-free cultured cells, Progress of Medicine, Japan, published Nov. 10, 1990, vol. 155, No. 6, pp. 355-359.

native human IL-15

ATGAGAAT TCGAAACCA CATTTGAGAA GTATTTCCAT CCAGTGCTAC
TTGTGTTTAC TTCTAAACAG TCATTTTCTA ACTGAAGCTG GCATTCATGT
CTTCATTTTG GGCTGTTTCA GTGCAGGGCT TCCTAAAACA GAAGCCAACT
GGGTGAATGT AATAAGTGAT TTGAAAAAAA TTGAAGATCT TATTCAATCT
ATGCATATTG ATGCTACTTT ATATACGGAA AGTGATGTTC ACCCCAGTTG
CAAAGTAACA GCAATGAAGT GCTTTCTCTT GGAGTTACAA GTTATTTCAC
TTGAGTCCGG AGATGCAAGT ATTCATGATA CAGTAGAAAA TCTGATCATC
CTAGCAAACA ACAGTTTGTC TTCTAATGGG AATGTAACAG AATCTGGATG
CAAAGAATGT GAGGAACTGG AGGAAAAAAA TATTAAAGAA TTTTTGCAGA
GTTTTGTACA TATTGTCCAA ATGTTCATCA ACACTTCTTG A

Fig. 1A

MRISKPHLRSISIQCYLCLLLNSHFLTEAGIHVFILGCFSAGLPKTEAN*WVNV
ISDLKKIEDLIQSMHIDATLYTESDVHPSCKVTAMKCFLLELQVISLESGDASIHDT
VENLIILANNSLSSNGNVTESGCKECEELEEKNIKEFLQSFVHIVQMFINTS*

Fig. 1B native human IL-15Ra

ATGGCCCC GCGGCGGGCG CGCGGCTGCC GGACCCTCGG TCTCCCGGCG
CTGCTACTGC TGCTGCTGCT CCGGCCGCCG GCGACGCGGG GCATCACGTG
CCCTCCCCCC ATGTCCGTGG AACACGCAGA CATCTGGGTC AAGAGCTACA
GCTTGTACTC CAGGGAGCGG TACATTTGTA ACTCTGGTTT CAAGCGTAAA
GCCGGCACGT CCAGCCTGAC GGAGTGCGTG TTGAACAAGG CCACGAATGT
CGCCCACTGG ACAACCCCA GTCTCAAATG CATTAGAGAC CCTGCCCTGG
TTCACCAAAG GCCAGCGCCA CCCTCCACAG TAACGACGGC AGGGGTGACC
CCACAGCCAG AGAGCCTCTC CCCTTCTGGA AAAGAGCCCG CAGCTTCATC
TCCCAGCTCA ACAACACAG CGGCCACAAC AGCAGCTATT GTCCCGGGCT
CCCAGCTGAT GCCTTCAAAA TCACCTTCCA CAGGAACCAC AGAGATAAGC
AGTCATGAGT CCTCCCACGG CACCCCCTCT CAGACAACAG CCAAGAACTG
GGAACTCACA GCATCCGCCT CCCACCAGCC GCCAGGTGTG TATCCACAGG
GCCACAGCGA CACCACTGTG GCTATCTCCA CGTCCACTGT CCTGCTGTGT
GGGCTGAGCG CTGTGTCTCT CCTGGCATGC TACCTCAAGT CAAGGCAAAC
TCCCCCGCTG GCCAGCGTTG AAATGGAAGC CATGGAGGCT CTGCCGGTGA
CTTGGGGGAC CAGCAGCAGA GATGAAGACT TGGAAAACTG CTCTCACCAC
CTATGA

Fig. 2A

MAPRRARGCRTLGLPALLLLLLLRPPATRGITCPPPMSVEHADIWVKSYSLYSRERYICN
SGFKRKAGTSSLTECVLNKATNVAHWTTPSLKCIRDPALVHQRPAPPSTVTTAGVTPQPES
LSPSGKEPAASSPSSNNTAATTAAIVPGSQLMPSKSPSTGTTEISSHESSHGTPSQTTAKNWE
LTASASHQPPGVYPQGHSDTTVAISTSTVLLCGLSAVSLLACYLKSRQTPPLASVEMEAMEA
LPVTWGTSSRDEDLENCSHHL

Fig. 2B native soluble human IL-15Ra

ATGGCCCC GCGGCGGGCG CGCGGCTGCC GGACCCTCGG TCTCCCGGCG
CTGCTACTGC TGCTGCTGCT CCGGCCGCCG GCGACGCGGG GCATCACGTG
CCCTCCCCCC ATGTCCGTGG AACACGCAGA CATCTGGGTC AAGAGCTACA
GCTTGTACTC CAGGGAGCGG TACATTTGTA ACTCTGGTTT CAAGCGTAAA
GCCGGCACGT CCAGCCTGAC GGAGTGCGTG TTGAACAAGG CCACGAATGT
CGCCCACTGG ACAACCCCA GTCTCAAATG CATTAGAGAC CCTGCCCTGG
TTCACCAAAG GCCAGCGCCA CCCTCCACAG TAACGACGGC AGGGGTGACC
CCACAGCCAG AGAGCCTCTC CCCTTCTGGA AAAGAGCCCG CAGCTTCATC
TCCAGCTCA AACAACACAG CGGCCACAAC AGCAGCTATT GTCCCGGGCT
CCCAGCTGAT GCCTTCAAAA TCACCTTCCA CAGGAACCAC AGAGATAAGC
AGTCATGAGT CCTCCCACGG CACCCCCTCT CAGACAACAG CCAAGAACTG
GGAACTCACA GCATCCGCCT CCCACCAGCC GCCAGGTGTG TATCCACAGG
GCCACAGCGA CACCACT

Fig. 3A

MAPRRARGCRTLGLPALLLLLLLRPPATRG*ITCPPPMSVEHADIWVKSYSLYSRERYICN
SGFKRKAGTSSLTECVLNKATNVAHWTTPSLKCIRDPALVHQRPAPPSTVTTAGVTPQPES
LSPSGKEPAASSPSSNNTAATTAAIVPGSQLMPSKSPSTGTTEISSHESSHGTPSQTTAKNWE
LTASASHQPPGVYPQGHSDTT*

Fig. 3B

AG32 huIL15opt

```
CCTGGCCATTGCATACGTTGTATCCATATCATAATATGTACATTTATATTGGCTCATGTCCA
ACATTACCGCCATGTTGACATTGATTATTGACTAGTTATTAATAGTAATCAATTACGGGGTC
ATTAGTTCATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCATAGTAACG
CCAATAGGGACTTTCCATTGACGTCAATGGGTGGAGTATTTACGGTAAACTGCCCACTTGGC
AGTACATCAAGTGTATCATATGCCAAGTACGCCCCCTATTGACGTCAATGATGGTAAATGGC
CCGCCTGGCATTATGCCCAGTACATGACCTTATGGGACTTTCCTACTTGGCAGTACATCTAC
GTATTAGTCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATG
GGCGGTAGGCGTGTACGGTGGAGGTCTATATAAGCAGAGCTCGTTTAGTGAACCGTCAGAT
CGCCTGGAGACGCCATCCACGCTGTTTTGACCTCCATAGAAGACACCGGGACCGATCCAGCC
TCCGCGGGcgcgcgtcgacaagaaATGCGGATCTCGAAGCCGCACCTGCGGTCGATATCGAT
CCAGTGCTACCTGTGCCTGCTCCTGAACTCGCACTTCCTCACGGAGGCCGGTATACACGTCT
TCATCCTGGGCTGCTTCTCGGCGGGGCTGCCGAAGACGGAGGCGAACTGGGTGAACGTGATC
TCGGACCTGAAGAAGATCGAGGACCTCATCCAGTCGATGCACATCGACGCGACGCTGTACAC
GGAGTCGGACGTCCACCCGTCGTGCAAGGTCACGGCGATGAAGTGCTTCCTCCTGGAGCTCC
AAGTCATCTCGCTCGAGTCGGGGGACGCGTCGATCCACGACACGGTGGAGAACCTGATCATC
CTGGCGAACAACTCGCTGTCGTCGAACGGGAACGTCACGGAGTCGGGCTGCAAGGAGTGCGA
GGAGCTGGAGGAGAAGAACATCAAGGAGTTCCTGCAGTCGTTCGTGCACATCGTCCAGATGT
TCATCAACACGTCGTGAgggcccggcgcgccgaattcgcggatatcggttaacggatccaGA
TCTGCTGTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCGCATTGTC
TGAGTAGGTGTCATTCTATTCTGGGGGGTGGGGTGGGGCAGGACAGCAAGGGGGAGGATTGG
GAAGACAATAGCAGGCATGCTGGGGATGCGGTGGGCTCTATGGGTACCCAGGTGCTGAAGAA
TTGACCCGGTTCCTCCTGGGCCAGAAAGAAGCAGGCACATCCCCTTCTCTGTGACACACCCT
GTCCACGCCCCTGGTTCTTAGTTCCAGCCCCACTCATAGGACACTCATAGCTCAGGAGGGCT
CCGCCTTCAATCCCACCCGCTAAAGTACTTGGAGCGGTCTCTCCCTCCCTCATCAGCCCACC
AAACCAAACCTAGCCTCCAAGAGTGGGAAGAAATTAAAGCAAGATAGGCTATTAAGTGCAGA
GGGAGAGAAAATGCCTCCAACATGTGAGGAAGTAATGAGAGAAATCATA
```

```
   1 CCTGGCCATTGCATACGTTGTATCCATATCATAATATGTACATTTATATTGGCTCATGTCCAACATTACCGCCAT
  76 GTTGACATTGATTATTGACTAGTTATTAATAGTAATCAATTACGGGGTCATTAGTTCATAGCCCATATATGGAGT
 151 TCCGCGTTACATAACTTACGGTAAATGGCCCGCCTGGCTGACCGCCCAACGACCCCCGCCCATTGACGTCAATAA
 226 TGACGTATGTTCCCATAGTAACGCCAATAGGGACTTTCCATTGACGTCAATGGGTGGAGTATTTACGGTAAACTG
 301 CCCACTTGGCAGTACATCAAGTGTATCATATGCCAAGTACGCCCCCTATTGACGTCAATGATGGTAAATGGCCCG
 376 CCTGGCATTATGCCCAGTACATGACCTTATGGGACTTTCCTACTTGGCAGTACATCTACGTATTAGTCATCGCTA
 451 TTACCATGGTGATGCGGTTTTGGCAGTACATCAATGGGCGTGGATAGCGGTTTGACTCACGGGGATTTCCAAGTC
 526 TCCACCCCATTGACGTCAATGGGAGTTTGTTTTGGCACCAAAATCAACGGGACTTTCCAAAATGTCGTAACAACT
 601 CCGCCCCATTGACGCAAATGGGCGGTAGGCGTGTACGGTGGGAGGTCTATATAAGCAGAGCTCGTTTAGTGAACC
 676 GTCAGATCGCCTGGAGACGCCATCCACGCTGTTTTGACCTCCATAGAAGACACCGGGACCGATCCAGCCTCCGCG
 751 GGcgcgcgtcgacaagaa ATG CGG ATC TCG AAG CCG CAC CTG CGG TCG ATA TCG ATC CAG
                     1▶ M   R   I   S   K   P   H   L   R   S   I   S   I   Q
 811 TGC TAC CTG TGC CTG CTC CTG AAC TCG CAC TTC CTC ACG GAG GCC GGT ATA CAC GTC
  15▶ C   Y   L   C   L   L   L   N   S   H   F   L   T   E   A   G   I   H   V
 868 TTC ATC CTG GGC TGC TTC TCG GCG GGG CTG CCG AAG ACG GAG GCG AAC TGG GTG AAC
  34▶ F   I   L   G   C   F   S   A   G   L   P   K   T   E   A   N   W   V   N
 925 GTG ATC TCG GAC CTG AAG AAG ATC GAG GAC CTC ATC CAG TCG ATG CAC ATC GAC GCG
  53▶ V   I   S   D   L   K   K   I   E   D   L   I   Q   S   M   H   I   D   A
 982 ACG CTG TAC ACG GAG TCG GAC GTC CAC CCG TCG TGC AAG GTC ACG GCG ATG AAG TGC
  72▶ T   L   Y   T   E   S   D   V   H   P   S   C   K   V   T   A   M   K   C
1039 TTC CTC CTG GAG CTC CAA GTC ATC TCG CTC GAG TCG GGG GAC GCG TCG ATC CAC GAC
  91▶ F   L   L   E   L   Q   V   I   S   L   E   S   G   D   A   S   I   H   D
1096 ACG GTG GAG AAC CTG ATC ATC CTG GCG AAC AAC TCG CTG TCG TCG AAC GGG AAC GTC
 110▶ T   V   E   N   L   I   I   L   A   N   N   S   L   S   S   N   G   N   V
1153 ACG GAG TCG GGC TGC AAG GAG TGC GAG GAG CTG GAG GAG AAG AAC ATC AAG GAG TTC
 129▶ T   E   S   G   C   K   E   C   E   E   L   E   E   K   N   I   K   E   F
1210 CTG CAG TCG TTC GTG CAC ATC GTC CAG ATG TTC ATC AAC ACG TCG TGA gggcccggcgc
 148▶ L   Q   S   F   V   H   I   V   Q   M   F   I   N   T   S   *
1269 gccgaattcgcggatatcggttaacggatccaGATCTGCTGTGCCTTCTAGTTGCCAGCCATCTGTTGTTTGCCC
1344 CTCCCCCGTGCCTTCCTTGACCCTGGAAGGTGCCACTCCCACTGTCCTTTCCTAATAAAATGAGGAAATTGCATC
1419 GCATTGTCTGAGTAGGTGTCATTCTATTCTGGGGGGTGGGGTGGGGCAGGACAGCAAGGGGGAGGATTGGGAAGA
1494 CAATAGCAGGCATGCTGGGGATGCGGTGGGCTCTATGGGTACCCAGGTGCTGAAGAATTGACCCGGTTCCTCCTG
1569 GGCCAGAAAGAAGCAGGCACATCCCCTTCTCTGTGACACACCCTGTCCACGCCCTGGTTCTTAGTTCCAGCCCC
1644 ACTCATAGGACACTCATAGCTCAGGAGGGCTCCGCCTTCAATCCCACCCGCTAAAGTACTTGGAGCGGTCTCTCC
1719 CTCCCTCATCAGCCCACCAAACCAAACCTAGCCTCCAAGAGTGGGAAGAAATTAAAGCAAGATAGGCTATTAAGT
1794 GCAGAGGGAGAGAAAATGCCTCCAACATGTGAGGAAGTAATGAGAGAAATCATA
```

Fig. 4D

AG59 CMV huIL15tPA6

```
CCTGGCCATTGCATACGTTGTATCCATATCATAATATGTACATTTATATTGGCTCATGTCCA
ACATTACCGCCATGTTGACATTGATTATTGACTAGTTATTAATAGTAATCAATTACGGGTC
ATTAGTTCATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCATAGTAACG
CCAATAGGGACTTTCCATTGACGTCAATGGGTGGAGTATTTACGGTAAACTGCCCACTTGGC
AGTACATCAAGTGTATCATATGCCAAGTACGCCCCCTATTGACGTCAATGATGGTAAATGGC
CCGCCTGGCATTATGCCCAGTACATGACCTTATGGGACTTTCCTACTTGGCAGTACATCTAC
GTATTAGTCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATG
GGCGGTAGGCGTGTACGGTGGGAGGTCTATATAAGCAGAGCTCGTTTAGTGAACCGTCAGAT
CGCCTGGAGACGCCATCCACGCTGTTTTGACCTCCATAGAAGACACCGGGACCGATCCAGCC
TCCGCGGgcgcgtcgacaagaaATGGATGCAATGAAGAGAGGGCTCTGCTGTGTGCTGCT
GCTGTGTGGAGCAGTCTTCGTTTCGCCCAGCCAGGAAATCCATGCCCGATTCAGAAGAGGAG
CCAGAAACTGGGTGAACGTGATCTCGGACCTGAAGAAGATCGAGGACCTCATCCAGTCGATG
CACATCGACGCGACGCTGTACACGGAGTCGGACGTCCACCCGTCGTGCAAGGTCACGGCGAT
GAAGTGCTTCCTCCTGGAGCTCCAAGTCATCTCGCTCGAGTCGGGGGACGCGTCGATCCACG
ACACGGTGGAGAACCTGATCATCCTGGCGAACAACTCGCTGTCGTCGAACGGGAACGTCACG
GAGTCGGGCTGCAAGGAGTGCGAGGAGCTGGAGGAGAAGAACATCAAGGAGTTCCTGCAGTC
GTTCGTGCACATCGTCCAGATGTTCATCAACACGTCGTGAgggcccggcgcgccgaattcgc
ggatatcggttaacggatccaGATCTGCTGTGCCTTCTAGTTGCCAGCCATCTGTTGTTTGC
CCCTCCCCCGTGCCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGGGTGGGGTGGGGC
AGGACAGCAAGGGGGAGGATTGGGAAGACAATAGCAGGCATGCTGGGGATGCGGTGGGCTCT
ATGGGTACCCAGGTGCTGAAGAATTGACCCGGTTCCTCCTGGGCCAGAAAGAAGCAGGCACA
TCCCCTTCTCTGTGACACACCCTGTCCACGCCCTGGTTCTTAGTTCCAGCCCCACTCATAG
GACACTCATAGCTCAGGAGGGCTCCGCCTTCAATCCCACCCGCTAAAGTACTTGGAGCGGTC
TCTCCCTCCCTCATCAGCCCACCAAACCAAACCTAGCCTCCAAGAGTGGGAAGAAATTAAAG
CAAGATAGGCTATTAAGTGCAGAGGGAGAGAAAATGCCTCCAACATGTGAGGAAGTAATGAG
AGAAATCATA
```

AG59 CMV huIL15tPA6
(1808 bp)

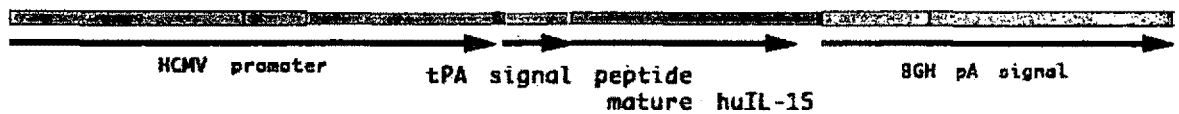

HCMV promoter    tPA signal peptide    BGH pA signal
                 mature huIL-15

Fig. 5C

```
   1 CCTGGCCATTGCATACGTTGTATCCATATCATAATATGTACATTTATATTGGCTCATGTCCAACATTACCGCCATGTTGACATTGATTATTGACTAGTTA
 101 TTAATAGTAATCAATTACGGGGTCATTAGTTCATAGCCCATATATGGAGTTCCGCGTTACATAACTTACGGTAAATGGCCCGCCTGGCTGACCGCCCAAC
 201 GACCCCCGCCCATTGACGTCAATAATGACGTATGTTCCCATAGTAACGCCAATAGGGACTTTCCATTGACGTCAATGGGTGGAGTATTTACGGTAAACTG
 301 CCCACTTGGCAGTACATCAAGTGTATCATATGCCAAGTACGCCCCCTATTGACGTCAATGATGGTAAATGGCCCGCCTGGCATTATGCCCAGTACATGAC
 401 CTTATGGGACTTTCCTACTTGGCAGTACATCTACGTATTAGTCATCGCTATTACCATGGTGATGCGGTTTTGGCAGTACATCAATGGGCGTGGATAGCGG
 501 TTTGACTCACGGGGATTTCCAAGTCTCCACCCCATTGACGTCAATGGGAGTTTGTTTTGGCACCAAAATCAACGGGACTTTCCAAAATGTCGTAACAACT
 601 CCGCCCCATTGACGCAAATGGGCGGTAGGCGTGTACGGTGGGAGGTCTATATAAGCAGAGCTCGTTTAGTGAACCGTCAGATCGCCTGGAGACGCCATCC
 701 ACGCTGTTTTGACCTCCATAGAAGACACCGGGACCGATCCAGCCTCCGCGGgcgcgcgtcgacaagaa ATG GAT GCA ATG AAG AGA GGG CTC
                                                                         1▸ M   D   A   M   K   R   G   L
 793 TGC TGT GTG CTG CTG CTG TGT GGA GCA GTC TTC GTT TCG CCC AGC CAG GAA ATC CAT GCC CGA TTC AGA AGA GGA
   9▸ C   C   V   L   L   L   C   G   A   V   F   V   S   P   S   Q   E   I   H   A   R   F   R   R   G
 868 GCC AGA AAC TGG GTG AAC GTG ATC TCG GAC CTG AAG AAG ATC GAG GAC CTC ATC CAG TCG ATG CAC ATC GAC GCG
  34▸ A   R   ━━━━━━━━━━━━━━━━━━━━━━━━━━━━━━━━━━━━━━━━━━━━━━━━━━━━━━━━━━━━━━━━━━━━━━━━━━━━━━━━━━━━━━━━━━
           ▶ N   W   V   N   V   I   S   D   L   K   K   I   E   D   L   I   Q   S   M   H   I   D   A
 943 ACG CTG TAC ACG GAG TCG GAC GTC CAC CCG TCG TGC AAG GTC ACG GCG ATG AAG TGC TTC CTC CTG GAG CTC CAA
  24▸ T   L   Y   T   E   S   D   V   H   P   S   C   K   V   T   A   M   K   C   F   L   L   E   L   Q
1018 GTC ATC TCG CTC GAG TCG GGG GAC GCG TCG ATC CAC GAC ACG GTG GAG AAC CTG ATC ATC CTG GCG AAC AAC TCG
  49▸ V   I   S   L   E   S   G   D   A   S   I   H   D   T   V   E   N   L   I   I   L   A   N   N   S
1093 CTG TCG TCG AAC GGG AAC GTC ACG GAG TCG GGC TGC AAG GAG TGC GAG GAG CTG GAG GAG AAG AAC ATC AAG GAG
  74▸ L   S   S   N   G   N   V   T   E   S   G   C   K   E   C   E   E   L   E   E   K   N   I   K   E
1168 TTC CTG CAG TCG TTC GTG CAC ATC GTC CAG ATG TTC ATC AAC ACG TCG TGA gggcccggcgcgccgaattcgcggatatcggt
  99▸ F   L   Q   S   F   V   H   I   V   Q   M   F   I   N   T   S   *
1251 taacggatccaGATCTGCTGTGCCTTCTAGTTGCCAGCCATCTGTTGTTTGCCCCTCCCCCGTGCCTTCCTTGACCCTGGAAGGTGCCACTCCCACTGTC
1351 CTTTCCTAATAAAATGAGGAAATTGCATCGCATTGTCTGAGTAGGTGTCATTCTATTCTGGGGGGTGGGGTGGGGCAGGACAGCAAGGGGGAGGATTGGG
1451 AAGACAATAGCAGGCATGCTGGGGATGCGGTGGGCTCTATGGGTACCCAGGTGCTGAAGAATTGACCCGGTTCCTCCTGGGCCAGAAAGAAGCAGGCACA
1551 TCCCCTTCTCTGTGACACACCCTGTCCACGCCCCTGGTTCTTAGTTCCAGCCCCACTCATAGGACACTCATAGCTCAGGAGGGCTCCGCCTTCAATCCCA
1651 CCCGCTAAAGTACTTGGAGCGGTCTCTCCCTCCCTCATCAGCCCACCAAACCAAACCTAGCCTCCAAGAGTGGGAAGAAATTAAAGCAAGATAGGCTATT
1751 AAGTGCAGAGGGAGAGAAAATGCCTCCAACATGTGAGGAAGTAATGAGAGAAATCATA
```

Fig. 5D

AG79 huIL15Ra

CCTGGCCATTGCATACGTTGTATCCATATCATAATATGTACATTTATATTGGCTCATGTCCA
ACATTACCGCCATGTTGACATTGATTATTGACTAGTTATTAATAGTAATCAATTACGGGGTC
ATTAGTTCATAGCCCATATATGGAGTTCCGCGTTACATAACTTACGGTAAATGGCCCGCCTG
GCTGACCGCCCAACGACCCCGCCCATTGACGTCAATAATGACGTATGTTCCCATAGTAACG
CCAATAGGGACTTTCCATTGACGTCAATGGGTGGAGTATTTACGGTAAACTGCCCACTTGGC
AGTACATCAAGTGTATCATATGCCAAGTACGCCCCTATTGACGTCAATGATGGTAAATGGC
CCGCCTGGCATTATGCCCAGTACATGACCTTATGGGACTTTCCTACTTGGCAGTACATCTAC
GTATTAGTCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATG
GGCGGTAGGCGTGTACGGTGGAGGTCTATATAAGCAGAGCTCGTTTAGTGAACCGTCAGAT
CGCCTGGAGACGCCATCCACGCTGTTTGACCTCCATAGAAGACACCGGGACCGATCCAGCC
TCCGCGGgcgcgtcgacgctagcaagaaATGGCCCCGAGGCGGGCGCGAGGCTGCCGGAC
CCTCGGTCTCCGGCGCTGCTACTGCTCCTGCTGCTCCGGCCGCCGGCGACGCGGGGCATCA
CGTGCCCGCCCCCATGTCCGTGGAGCACGCAGACATCTGGGTCAAGAGCTACAGCTTGTAC
TCCCGGGAGCGGTACATCTGCAACTCGGGTTTCAAGCGGAAGGCCGGCACGTCCAGCCTGAC
GGAGTGCGTGTTGAACAAGGCCACGAATGTCGCCCACTGGACGACCCCCTCGCTCAAGTGCA
TCCGCGACCCGGCCCTGGTTCACCAGCGGCCCGCGCCACCCTCCACCGTAACGACGGCGGGG
GTGACCCCGCAGCCGGAGAGCCTCTCCCCGTCGGGAAAGGAGCCCGCCGCGTCGTCGCCCAG
CTCAACAACACGGCGGCCACAACTGCAGCGATCGTCCCGGGCTCCCAGCTGATGCCGTCGA
AGTCGCCGTCCACGGGAACCACGGAGATCAGCAGTCATGAGTCCTCCCACGGCACCCCTCG
CAAACGACGGCCAAGAACTGGGAACTCACGGCGTCCGCCTCCCACCAGCCGCCGGGGGTGTA
TCCGCAAGGCCACAGCGACACCACGGTGGCGATCTCCACGTCCACGGTCCTGCTGTGTGGGC
TGAGCGCGGTGTCGCTCCTGGCGTGCTACCTCAAGTCGAGGCAGACTCCCCCGCTGGCCAGC
GTTGAGATGGAGGCCATGGAGGCTCTGCCGGTGACGTGGGGACCAGCAGCAGGGATGAGGA
CTTGGAGAACTGCTCGCACCACCTATAATGAgaattcgatccaGATCTGCTGTGCCTTCTAG
TTGCCAGCCATCTGTTGTTTGCCCCTCCCCGTGCCTTCCTTGACCCTGGAAGGTGCCACTC
CCACTGTCCTTTCCTAATAAAATGAGGAAATTGCATCGCATTGTCTGAGTAGGTGTCATTCT
ATTCTGGGGGGTGGGGTGGGGCAGGACAGCAAGGGGGAGGATTGGGAAGACAATAGCAGGCA
TGCTGGGGATGCGGTGGGCTCTATGGGTACCCAGGTGCTGAAGAATTGACCCGGTTCCTCCT
GGGCCAGAAAGAAGCAGGCACATCCCCTTCTCTGTGACACACCCTGTCCACGCCCTGGTTC
TTAGTTCCAGCCCCACTCATAGGACACTCATAGCTCAGGAGGGCTCCGCCTTCAATCCCACC
CGCTAAAGTACTTGGAGCGGTCTCTCCCTCCCTCATCAGCCCACCAAACCAAACCTAGCCTC
CAAGAGTGGGAAGAAATTAAAGCAAGATAGGCTATTAAGTGCAGAGGGAGAGAAAATGCCTC
CAACATGTGAGGAAGTAATGAGAGAAATCATA

```
   1 CCTGGCCATTGCATACGTTGTATCCATATCATAATATGTACATTTATATTGGCTCATGTCCAACATTACCGCCATGT
  78 TGACATTGATTATTGACTAGTTATTAATAGTAATCAATTACGGGGTCATTAGTTCATAGCCCATATATGGAGTTCCG
 155 CGTTACATAACTTACGGTAAATGGCCCGCCTGGCTGACCGCCCAACGACCCCCGCCCATTGACGTCAATAATGACGT
 232 ATGTTCCCATAGTAACGCCAATAGGGACTTTCCATTGACGTCAATGGGTGGAGTATTTACGGTAAACTGCCCACTTG
 309 GCAGTACATCAAGTGTATCATATGCCAAGTACGCCCCCTATTGACGTCAATGATGGTAAATGGCCCGCCTGGCATTA
 386 TGCCCAGTACATGACCTTATGGGACTTTCCTACTTGGCAGTACATCTACGTATTAGTCATCGCTATTACCATGGTGA
 463 TGCGGTTTTGGCAGTACATCAATGGGCGTGGATAGCGGTTTGACTCACGGGGATTTCCAAGTCTCCACCCCATTGAC
 540 GTCAATGGGAGTTTGTTTTGGCACCAAAATCAACGGGACTTTCCAAAATGTCGTAACAACTCCGCCCCATTGACGCA
 617 AATGGGCGGTAGGCGTGTACGGTGGGAGGTCTATATAAGCAGAGCTCGTTTAGTGAACCGTCAGATCGCCTGGAGAC
 694 GCCATCCACGCTGTTTTGACCTCCATAGAAGACACCGGGACCGATCCAGCCTCCGCGGgcgcgcgtcgacgctagca
 771 agaa ATG GCC CCG AGG CGG GCG CGA GGC TGC CGG ACC CTC GGT CTC CCG GCG CTG CTA
   1▶  M   A   P   R   R   A   R   G   C   R   T   L   G   L   P   A   L   L
 829 CTG CTC CTG CTG CTC CGG CCG CCG GCG ACG CGG GGC ATC ACG TGC CCG CCC CCC ATG
  19▶ L   L   L   L   L   R   P   P   A   T   R   G   I   T   C   P   P   P   M
 886 TCC GTG GAG CAC GCA GAC ATC TGG GTC AAG AGC TAC AGC TTG TAC TCC CGG GAG CGG
  38▶ S   V   E   H   A   D   I   W   V   K   S   Y   S   L   Y   S   R   E   R
 943 TAC ATC TGC AAC TCG GGT TTC AAG CGG AAG GCC GGC ACG TCC AGC CTG ACG GAG TGC
  57▶ Y   I   C   N   S   G   F   K   R   K   A   G   T   S   S   L   T   E   C
1000 GTG TTG AAC AAG GCC ACG AAT GTC GCC CAC TGG ACG ACC CCC TCG CTC AAG TGC ATC
  76▶ V   L   N   K   A   T   N   V   A   H   W   T   T   P   S   L   K   C   I
1057 CGC GAC CCG GCC GCC CTG GTT CAC CAG CGG CCA CCC TCC ACC GTA ACG ACG GCG
  95▶ R   D   P   A   L   V   H   Q   R   P   A   P   P   S   T   V   T   T   A
1114 GGG GTG ACC CCG CAG CCG GAG AGC CTC TCC CCG TCG GGA AAG GAG CCC GCC GCG TCG
 114▶ G   V   T   P   Q   P   E   S   L   S   P   S   G   K   E   P   A   A   S
1171 TCG CCC AGC TCG AAC AAC ACG GCG GCC ACA ACT GCA GCG ATC GTC CCG GGC TCC CAG
 133▶ S   P   S   S   N   N   T   A   A   T   T   A   A   I   V   P   G   S   Q
1228 CTG ATG CCG TCG AAG TCG CCG TCG GGA ACC ACG GAG ATC AGC AGT CAT GAG TCC
 152▶ L   M   P   S   K   S   P   S   G   T   T   E   I   S   S   H   E   S
1285 TCC CAC GGC ACC CCC TCG CAA ACG ACG GCC AAG AAC TGG GAA CTC ACG GCG TCC GCC
 171▶ S   H   G   T   P   S   Q   T   T   A   K   N   W   E   L   T   A   S   A
1342 TCC CAC CAG CCG CCG GGG GTG TAT CCG CAA GGC CAC AGC GAC ACC ACG GTG GCG ATC
 190▶ S   H   Q   P   P   G   V   Y   P   Q   G   H   S   D   T   T   V   A   I
1399 TCC ACG TCC ACG GTC CTG CTG TGT GGG CTG AGC GCG GTG TCG CTC CTG GCG TGC TAC
 209▶ S   T   S   T   V   L   L   C   G   L   S   A   V   S   L   L   A   C   Y
1456 CTC AAG TCG AGG CAG ACT CCC CCG CTG GCC AGC GTT GAG ATG GAG GCC ATG GAG GCT
 228▶ L   K   S   R   Q   T   P   P   L   A   S   V   E   M   E   A   M   E   A
1513 CTG CCG GTG ACG TGG GGG ACC AGC AGC AGG GAT GAG GAC TTG GAG AAC TGC TCG CAC
 247▶ L   P   V   T   W   G   T   S   S   R   D   E   D   L   E   N   C   S   H
1570 CAC CTA TAA TGA gaattcgatcca GAT CTG CTG TGC CTT CTA GTT GCC AGC CAT CTG TTG
 266▶ H   L   *   *
1630 TTT GCC CCT CCC CCG TGC CTT CCT TGA CCC TGG AAG TGG CCA CTC CCA CTG TCC TTT
1687 CCT AAT AAA ATG AGG AAA TTG C ATCGCATTGTCTGAGTAGGTGTCATTCTATTCTGGGGGGTGGGGTGG
1756 GGCAGGACAGCAAGGGGGAGGATTGGGAAGACAATAGCAGGCATGCTGGGGATGCGGTGGGCTCTATGGGTACCCAG
1833 GTGCTGAAGAATTGACCCGGTTCCTCCTGGGCCAGAAAGAAGCAGGCACATCCCCTTCTCTGTGACACACCCTGTCC
1910 ACGCCCCTGGTTCTTAGTTCCAGCCCCACTCATAGGACACTCATAGCTCAGGAGGGCTCGGCCTTCAATCCCACCCG
1987 CTAAAGTACTTGGAGCGGTCTCTCCCTCCCTCATCAGCCCACCAAACCAAACCTAGCCTCCAAGAGTGGGAAGAAAT
2064 TAAAGCAAGATAGGCTATTAAGTGCAGAGGGAGAGAAAATGCCTCCAACATGTGAGGAAGTAATGAGAGAAATCATA
```

Fig. 6D

AG98 CMV hu sIL15Ra

CCTGGCCATTGCATACGTTGTATCCATATCATAATATGTACATTTATATTGGCTCATGTCCA
ACATTACCGCCATGTTGACATTGATTATTGACTAGTTATTAATAGTAATCAATTACGGGGTC
ATTAGTTCATAGCCCATATATGGAGTTCCGCGTTACATAACTTACGGTAAATGGCCCGCCTG
GCTGACCGCCCAACGACCCCGCCCATTGACGTCAATAATGACGTATGTTCCCATAGTAACG
CCAATAGGGACTTTCCATTGACGTCAATGGGTGGAGTATTTACGGTAAACTGCCCACTTGGC
AGTACATCAAGTGTATCATATGCCAAGTACGCCCCTATTGACGTCAATGATGGTAAATGGC
CCGCCTGGCATTATGCCCAGTACATGACCTTATGGGACTTTCCTACTTGGCAGTACATCTAC
GTATTAGTCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATG
GGCGGTAGGCGTGTACGGTGGAGGTCTATATAAGCAGAGCTCGTTTAGTGAACCGTCAGAT
CGCCTGGAGACGCCATCCACGCTGTTTGACCTCCATAGAAGACACCGGGACCGATCCAGCC
TCCGCGGgcgcgcgtcgacgctagcaagaaATGGCCCCGAGGCGGGCGCGAGGCTGCCGGAC
CCTCGGTCTCCCGGCGCTGCTACTGCTCCTGCTGCTCCGGCCGCCGGCGACGCGGGGCATCA
CGTGCCCGCCCCCATGTCCGTGGAGCACGCAGACATCTGGGTCAAGAGCTACAGCTTGTAC
TCCCGGGAGCGGTACATCTGCAACTCGGGTTTCAAGCGGAAGGCCGGCACGTCCAGCCTGAC
GGAGTGCGTGTTGAACAAGGCCACGAATGTCGCCCACTGGACGACCCCCTCGCTCAAGTGCA
TCCGCGACCCGGCCCTGGTTCACCAGCGGCCCGCGCCACCTCCACCGTAACGACGGCGGGG
GTGACCCCGCAGCCGGAGAGCCTCTCCCCGTCGGGAAGGAGCCCGCCGCGTCGTCGCCCAG
CTCGAACAACACGGCGGCCACAACTGCAGCGATCGTCCCGGGCTCCCAGCTGATGCCGTCGA
AGTCGCCGTCCACGGGAACCACGGAGATCAGCAGTCATGAGTCCTCCCACGGCACCCCTCG
CAAACGACGGCCAAGAACTGGGAACTCACGGCGTCCGCCTCCACCAGCCGCCGGGGGTGTA
TCCGCAAGGCCACAGCGACACCACGTAATGAgaattcgcggatatcggttaacggatccGA
TCTGCTGTGCCTTCTAGTTGCCAGCCATCTGTTGTTTGCCCCTCCCCGTGCCTTCCTTGAC
CCTGGAAGGTGCCACTCCCACTGTCCTTTCCTAATAAAATGAGGAAATTGCATCGCATTGTC
TGAGTAGGTGTCATTCTATTCTGGGGGGTGGGGTGGGCAGGACAGCAAGGGGGAGGATTGG
GAAGACAATAGCAGGCATGCTGGGGATGCGGTGGCTCTATGGGTACCCAGGTGCTGAAGAA
TTGACCCGGTTCCTCCTGGGCCAGAAAGAAGCAGGCACATCCCCTTCTCTGTGACACACCCT
GTCCACGCCCTGGTTCTTAGTTCCAGCCCCACTCATAGGACACTCATAGCTCAGGAGGGCT
CCGCCTTCAATCCCACCCGCTAAAGTACTTGGAGCGGTCTCTCCCTCCCTCATCAGCCCACC
AAACCAAACCTAGCCTCCAAGAGTGGGAAGAAATTAAAGCAAGATAGGCTATTAAGTGCAGA
GGGAGAGAAAATGCCTCCAACATGTGAGGAAGTAATGAGAGAAATCATA

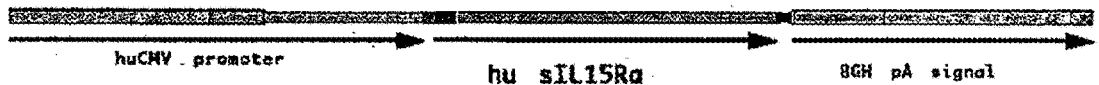

Fig. 7C

```
   1 CCTGGCCATTGCATACGTTGTATCCATATCATAATATGTACATTTATATTGGCTCATGTCCAACATTACCGCCATGTTGACATTGATTATTGACTAGTTA
 101 TTAATAGTAATCAATTACGGGGTCATTAGTTCATAGCCCATATATGGAGTTCCGCGTTACATAACTTACGGTAAATGGCCCGCCTGGCTGACCGCCCAAC
 201 GACCCCCGCCCATTGACGTCAATAATGACGTATGTTCCCATAGTAACGCCAATAGGGACTTTCCATTGACGTCAATGGGTGGAGTATTTACGGTAAACTG
 301 CCCACTTGGCAGTACATCAAGTGTATCATATGCCAAGTACGCCCCCTATTGACGTCAATGATGGTAAATGGCCCGCCTGGCATTATGCCCAGTACATGAC
 401 CTTATGGGACTTTCCTACTTGGCAGTACATCTACGTATTAGTCATCGCTATTACCATGGTGATGCGGTTTTGGCAGTACATCAATGGGCGTGGATAGCGG
 501 TTTGACTCACGGGGATTTCCAAGTCTCCACCCCATTGACGTCAATGGGAGTTTGTTTTGGCACCAAAATCAACGGGACTTTCCAAAATGTCGTAACAACT
 601 CCGCCCCATTGACGCAAATGGGCGGTAGGCGTGTACGGTGGGAGGTCTATATAAGCAGAGCTCGTTTAGTGAACCGTCAGATCGCCTGGAGACGCCATCC
 701 ACGCTGTTTTGACCTCCATAGAAGACACCGGGACCGATCCAGCCTCCGCGGgcgcgcgtcgacgctagcaagaa ATG GCC CCG AGG CGG GCG
                                                                               1> M   A   P   R   R   A
 793 CGA GGC TGC CGG ACC CTC GGT CTC CCG GCG CTG CTA CTG CTC CTG CTG CTC CGG CCG CCG GCG ACG CGG GGC ATC
  7> R   G   C   R   T   L   G   L   P   A   L   L   L   L   L   L   L   R   P   P   A   T   R   G   I
 868 ACG TGC CCG CCC CCC ATG TCC GTG GAG CAC GCA GAC ATC TGG GTC AAG AGC TAC AGC TTG TAC TCC CGG GAG CGG
 32> T   C   P   P   P   M   S   V   E   H   A   D   I   W   V   K   S   Y   S   L   Y   S   R   E   R
 943 TAC ATC TGC AAC TCG GGT TTC AAG CGG AAG GCC GGC ACG TCC AGC CTG ACG GAG TGC GTG TTG AAC AAG GCC ACG
 57> Y   I   C   N   S   G   F   K   R   K   A   G   T   S   S   L   T   E   C   V   L   N   K   A   T
1018 AAT GTC GCC CAC TGG ACC ACC CCC TCG CTC AAG TGC ATC CGC GAC CCG GCC CTG GTT CAC CAG CGG CCC GCG CCA
 82> N   V   A   H   W   T   T   P   S   L   K   C   I   R   D   P   A   L   V   H   Q   R   P   A   P
1093 CCC TCC ACC GTA ACG ACG GCG GGG GTG ACC CCG CAG CCG GAG AGC CTC TCC CCG TCG GGA AAG GAG CCC GCC GCG
107> P   S   T   V   T   T   A   G   V   T   P   Q   P   E   S   L   S   P   S   G   K   E   P   A   A
1168 TCG TCG CCC AGC TCG AAC AAC ACG GCG GCC ACA ACT GCA GCG ATC GTC CCG GGC TCC CAG CTG ATG CCG TCG AAG
132> S   S   P   S   S   N   N   T   A   A   T   T   A   A   I   V   P   G   S   Q   L   M   P   S   K
1243 TCG CCG TCC ACG GGA ACC ACG GAG ATC AGC AGT CAT GAG TCC TCC CAC GGC ACC CCC TCG CAA ACG ACG GCC AAG
157> S   P   S   T   G   T   T   E   I   S   S   H   E   S   S   H   G   T   P   S   Q   T   T   A   K
1318 AAC TGG GAA CTC ACG GCG TCC GCC TCC CAC CAG CCG CCG GGG GTG TAT CCG CAA GGC CAC AGC GAC ACC ACG TAA
182> N   W   E   L   T   A   S   A   S   H   Q   P   P   G   V   Y   P   Q   G   H   S   D   T   T   *
1393 TGA gaattcgcggatatcggttaacggatccaGATCTGCTGTGCCTTCTAGTTGCCAGCCATCTGTTGTTTGCCCCTCCCCCGTGCCTTCCTTGACCCT
207> *
1492 GGAAGGTGCCACTCCCACTGTCCTTTCCTAATAAAATGAGGAAATTGCATCGCATTGTCTGAGTAGGTGTCATTCTATTCTGGGGGGTGGGGTGGGGCAG
1592 GACAGCAAGGGGGAGGATTGGGAAGACAATAGCAGGCATGCTGGGGATGCGGTGGGCTCTATGGGTACCCAGGTGCTGAAGAATTGACCCGGTTCCTCCT
1692 GGGCCAGAAAGAAGCAGGCACATCCCCTTCTCTGTGACACACCCTGTCCACGCCCCTGGTTCTTAGTTCCAGCCCCACTCATAGGACACTCATAGCTCAG
1792 GAGGGCTCCGCCTTCAATCCCACCCGCTAAAGTACTTGGAGCGGTCTCTCCCTCCCTCATCAGCCCACCAAACCAAACCTAGCGTCCAAGAGTGGGAAGA
1892 AATTAAAGCAAGATAGGCTATTAAGTGCAGAGGGAGAGAAAATGCCTCCAACATGTGAGGAAGTAATGAGAGAAATCATA
```

Fig. 7D

AG151 huIL-15 huGM-CSF

```
CCTGGCCATTGCATACGTTGTATCCATATCATAATATGTACATTTATATTGGCTCATGTCCA
ACATTACCGCCATGTTGACATTGATTATTGACTAGTTATTAATAGTAATCAATTACGGGGTC
ATTAGTTCATAGCCCATATATGGAGTTCCGCGTTACATAACTTACGGTAAATGGCCCGCCTG
GCTGACCGCCCAACGACCCCGCCCATTGACGTCAATAATGACGTATGTTCCCATAGTAACG
CCAATAGGGACTTTCCATTGACGTCAATGGGTGGAGTATTTACGGTAAACTGCCCACTTGGC
AGTACATCAAGTGTATCATATGCCAAGTACGCCCCCTATTGACGTCAATGATGGTAAATGGC
CCGCCTGGCATTATGCCCAGTACATGACCTTATGGGACTTTCCTACTTGGCAGTACATCTAC
GTATTAGTCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATG
GGCGGTAGGCGTGTACGGTGGAGGTCTATATAAGCAGAGCTCGTTTAGTGAACCGTCAGAT
CGCCTGGAGACGCCATCCACGCTGTTTTGACCTCCATAGAAGACACCGGGACCGATCCAGCC
TCCGCGGGcgcgcgtcgacaagaaATGTGGCTCCAGAGCCTGCTACTCCTGGGGACGGTGGC
CTGCAGCATCTCGAACTGGGTGAACGTGATCTCGGACCTGAAGAAGATCGAGGACCTCATCC
AGTCGATGCACATCGACGCGACGCTGTACACGGAGTCGGACGTCCACCCGTCGTGCAAGGTC
ACGGCGATGAAGTGCTTCCTCCTGGAGCTCCAAGTCATCTCGCTCGAGTCGGGGGACGCGTC
GATCCACGACACGGTGGAGAACCTGATCATCCTGGCGAACAACTCGCTGTCGTCGAACGGGA
ACGTCACGGAGTCGGGCTGCAAGGAGTGCGAGGAGCTGGAGGAGAAGAACATCAAGGAGTTC
CTGCAGTCGTTCGTGCACATCGTCCAGATGTTCATCAACACGTCGTGAgggcccggcgcgcc
gaattcgcggatatcggttaacggatccaGATCTGCTGTGCCTTCTAGTTGCCAGCCATCTG
TTGTTTGCCCCTCCCCGTGCCTTCCTTGACCCTGGAAGGTGCCACTCCCACTGTCCTTTCC
TAATAAAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCTGGGGATGCGG
TGGGCTCTATGGGTACCCAGGTGCTGAAGAATTGACCCGGTTCCTCCTGGGCCAGAAGAAG
CAGGCACATCCCCTTCTCTGTGACACACCCTGTCCACGCCCTGGTTCTTAGTTCCAGCCCC
ACTCATAGGACACTCATAGCTCAGGAGGGCTCCGCCTTCAATCCCACCCGCTAAAGTACTTG
GAGCGGTCTCTCCCTCCCTCATCAGCCCACCAAACCAAACCTAGCCTCCAAGAGTGGGAAGA
AATTAAAGCAAGATAGGCTATTAAGTGCAGAGGGAGAGAAAATGCCTCCAACATGTGAGGAA
GTAATGAGAGAAATCATA
```

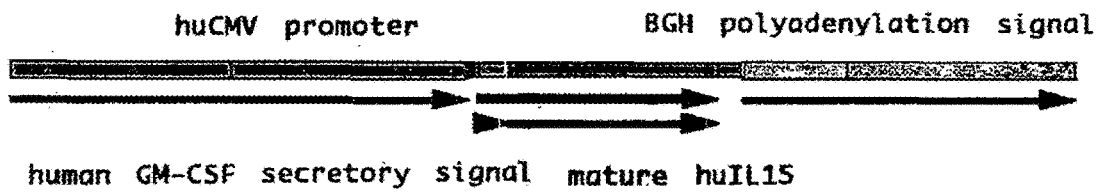

Fig. 8C

```
   1 CCTGGCCATTGCATACGTTGTATCCATATCATAATATGTACATTTATATTGGCTCATGTCCAACATTACCGCCATGTTGACATTGATTATTGACTAGTTA
 101 TTAATAGTAATCAATTACGGGGTCATTAGTTCATAGCCCATATATGGAGTTCCGCGTTACATAACTTACGGTAAATGGCCCGCCTGGCTGACCGCCCAAC
 201 GACCCCCGCCCATTGACGTCAATAATGACGTATGTTCCCATAGTAACGCCAATAGGGACTTTCCATTGACGTCAATGGGTGGAGTATTTACGGTAAACTG
 301 CCCACTTGGCAGTACATCAAGTGTATCATATGCCAAGTACGCCCCCTATTGACGTCAATGATGGTAAATGGCCCGCCTGGCATTATGCCCAGTACATGAC
 401 CTTATGGGACTTTCCTACTTGGCAGTACATCTACGTATTAGTCATCGCTATTACCATGGTGATGCGGTTTTGGCAGTACATCAATGGGCGTGGATAGCGG
 501 TTTGACTCACGGGGATTTCCAAGTCTCCACCCCATTGACGTCAATGGGAGTTTGTTTTGGCACCAAAATCAACGGGACTTTCCAAAATGTCGTAACAACT
 601 CCGCCCCATTGACGCAAATGGGCGGTAGGCGTGTACGGTGGGAGGTCTATATAAGCAGAGCTCGTTTAGTGAACCGTCAGATCGCCTGGAGACGCCATCC
 701 ACGCTGTTTTGACCTCCATAGAAGACACCGGGACCGATCCAGCCTCCGCGGGcgcgcgtcgacaagaa ATG TGG CTC CAG AGC CTG CTA
                                                                          1▶ M   W   L   Q   S   L   L
 790 CTC CTG GGG ACG GTG GCC TGC AGC ATC TCG AAC TGG GTG AAC GTG ATC TCG GAC CTG AAG AAG ATC GAG GAC CTC
  8▶ L   L   G   T   V   A   C   S   I   S   N   W   V   N   V   I   S   D   L   K   K   I   E   D   L
 865 ATC CAG TCG ATG CAC ATC GAC GCG ACG CTG TAC ACG GAG TCG GAC GTC CAC CCG TCG TGC AAG GTC ACG GCG ATG
 33▶ I   Q   S   M   H   I   D   A   T   L   Y   T   E   S   D   V   H   P   S   C   K   V   T   A   M
 940 AAG TGC TTC CTC CTG GAG CTC CAA GTC ATC TCG CTC GAG TCG GGG GAC GCG TCG ATC CAC GAC ACG GTG GAG AAC
 58▶ K   C   F   L   L   E   L   Q   V   I   S   L   E   S   G   D   A   S   I   H   D   T   V   E   N
1015 CTG ATC ATC CTG GCG AAC AAC TCG CTG TCG TCG AAC GGG AAC GTC ACG GAG TCG GGC TGC AAG GAG TGC GAG GAG
 83▶ L   I   I   L   A   N   N   S   L   S   S   N   G   N   V   T   E   S   G   C   K   E   C   E   E
1090 CTG GAG GAG AAG AAC ATC AAG GAG TTC CTG CAG TCG TTC GTG CAC ATC GTC CAG ATG TTC ATC AAC ACG TCG TGA
108▶ L   E   E   K   N   I   K   E   F   L   Q   S   F   V   H   I   V   Q   M   F   I   N   T   S   *
1165 gggcccggcgcgccgaattcgcggatatcggttaacggatccaGATCTGCTGTGCCTTCTAGTTGCCAGCCATCTGTTGTTTGCCCCTCCCCCGTGCCTT
1265 CCTTGACCCTGGAAGGTGCCACTCCCACTGTCCTTTCCTAATAAAATGAGGAAATTGCATCGCATTGTCTGAGTAGGTGTCATTCTATTCTGGGGGGTGG
1365 GGTGGGGCAGGACAGCAAGGGGGAGGATTGGGAAGACAATAGCAGGCATGCTGGGGATGCGGTGGGCTCTATGGGTACCCAGGTGCTGAAGAATTGACCC
1465 GGTTCCTCCTGGGCCAGAAAGAAGCAGGCACATCCCCTTCTCTGTGACACACCCTGTCCACGCCCTGGTTCTTAGTTCCAGCCCCACTCATAGGACACT
1565 CATAGCTCAGGAGGGCTCCGCCTTCAATCCCACCCGCTAAAGTACTTGGAGCGGTCTCTCCCTCCCTCATCAGCCCACCAAACCAAACCTAGCCTCCAAG
1665 AGTGGGAAGAAATTAAAGCAAGATAGGCTATTAAGTGCAGAGGGAGAGAAAATGCCTCCAACATGTGAGGAAGTAATGAGAGAAATCATA
```

Fig. 8D ized IL-15 signal transduction.

```
                               SEQUENCE LISTING

<160> NUMBER OF SEQ ID NOS: 18

<210> SEQ ID NO 1
<211> LENGTH: 162
<212> TYPE: PRT
<213> ORGANISM: Homo sapiens
<220> FEATURE:
<221> NAME/KEY: SIGNAL
<222> LOCATION: (1)...(48)
<220> FEATURE:
<223> OTHER INFORMATION: immature/precursor form of native human IL-15

<400> SEQUENCE: 1

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 2
<211> LENGTH: 489
<212> TYPE: DNA
<213> ORGANISM: Homo sapiens
<220> FEATURE:
<221> NAME/KEY: sig_peptide
<222> LOCATION: (1)...(145)
<220> FEATURE:
<223> OTHER INFORMATION: coding sequence of immature/precursor form of
      native human IL-15

<400> SEQUENCE: 2
atgagaattt cgaaaccaca tttgagaagt atttccatcc agtgctactt gtgtttactt     60
ctaaacagtc attttctaac tgaagctggc attcatgtct tcattttggg ctgtttcagt    120
gcagggcttc ctaaaacaga agccaactgg gtgaatgtaa taagtgattt gaaaaaaatt    180
gaagatctta ttcaatctat gcatattgat gctacttat atacggaaag tgatgttcac    240
cccagttgca agtaacagc aatgaagtgc tttctcttgg agttacaagt tatttcactt    300
gagtccggag atgcaagtat tcatgataca gtagaaaatc tgatcatcct agcaaacaac    360
```

```
agtttgtctt ctaatgggaa tgtaacagaa tctggatgca agaatgtgaa ggaactggag    420
gaaaaaaata ttaaagaatt tttgcagagt tttgtacata ttgtccaaat gttcatcaac    480
acttcttga                                                            489
```

<210> SEQ ID NO 3
<211> LENGTH: 267
<212> TYPE: PRT
<213> ORGANISM: Homo sapiens
<220> FEATURE:
<221> NAME/KEY: SIGNAL
<222> LOCATION: (1)...(30)
<220> FEATURE:
<223> OTHER INFORMATION: immature form of the native full length human
      IL-15 receptor alpha

<400> SEQUENCE: 3

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

<210> SEQ ID NO 4
<211> LENGTH: 205
<212> TYPE: PRT
<213> ORGANISM: Homo sapines
<220> FEATURE:
<221> NAME/KEY: SIGNAL
<222> LOCATION: (1)...(30)

<220> FEATURE:
<223> OTHER INFORMATION: immature form of the native soluble human IL-15
      receptor alpha

<400> SEQUENCE: 4

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr
        195                 200                 205
```

<210> SEQ ID NO 5
<211> LENGTH: 804
<212> TYPE: DNA
<213> ORGANISM: Homo sapiens
<220> FEATURE:
<221> NAME/KEY: sig_peptide
<222> LOCATION: (1)...(90)
<220> FEATURE:
<223> OTHER INFORMATION: coding sequence of immature form of the native
      full length human IL-15 receptor alpha

<400> SEQUENCE: 5

```
atggccccgc ggcgggcgcg cggctgccgg accctcggtc tcccggcgct gctactgctg      60
ctgctgctcc ggccgccggc gacgcggggc atcacgtgcc ctcccccat gtccgtggaa     120
cacgcagaca tctgggtcaa gagctacagc ttgtactcca gggagcggta catttgtaac    180
tctggtttca gcgtaaagc cggcacgtcc agcctgacgg agtgcgtgtt gaacaaggcc    240
acgaatgtcg cccactggac aaccccagt ctcaaatgca ttagagaccc tgccctggtt    300
caccaaaggc cagcgccacc ctccacagta cgacggcag gggtgacccc acagccagag    360
agcctctccc cttctggaaa agagcccgca gcttcatctc ccagctcaaa caacacagcg    420
gccacaacag cagctattgt cccgggctcc cagctgatgc cttcaaaatc accttccaca    480
ggaaccacag agataagcag tcatgagtcc tccacaggca ccccctctca gacaacagcc    540
aagaactggg aactcacagc atccgcctcc accagccgc aggtgtgtat ccacagggc     600
```

```
cacagcgaca ccactgtggc tatctccacg tccactgtcc tgctgtgtgg gctgagcgct    660
gtgtctctcc tggcatgcta cctcaagtca aggcaaactc ccccgctggc cagcgttgaa    720
atggaagcca tggaggctct gccggtgact tggggggacca gcagcagaga tgaagacttg    780
gaaaactgct ctcaccacct atga                                           804

<210> SEQ ID NO 6
<211> LENGTH: 615
<212> TYPE: DNA
<213> ORGANISM: Homo sapiens
<220> FEATURE:
<221> NAME/KEY: sig_peptide
<222> LOCATION: (1)...(90)
<220> FEATURE:
<223> OTHER INFORMATION: coding sequence of immature form of the native
      soluble human IL-15 receptor alpha

<400> SEQUENCE: 6
atggccccgc ggcgggcgcg cggctgccgg accctcggtc tcccggcgct gctactgctg     60
ctgctgctcc ggccgccggc gacgcggggc atcacgtgcc ctcccccccat gtccgtggaa   120 cacgcagaca tctgggtcaa gagctacagc ttgtactcca gggagcggta catttgtaac   180 tctggttca agcgtaaagc cggcacgtcc agcctgacgg agtgcgtgtt gaacaaggcc    240
acgaatgtcg cccactggac aaccccccagt ctcaaatgca ttagagaccc tgccctggtt   300
caccaaaggc cagcgccacc ctccacagta acgacgcgca gggtgacccc acagccagag   360
agcctctccc cttctggaaa agagcccgca gcttcatctc ccagctcaaa caacacagcg   420
gccacaacag cagctattgt cccgggctcc cagctgatgc cttcaaaatc accttccaca   480
ggaaccacag agataagcag tcatgagtcc tcccacggca cccctctca gacaacagcc   540 aagaactggg aactcacagc atccgcctcc accagccgc caggtgtgta tccacagggc   600
cacagcgaca ccact                                                    615

<210> SEQ ID NO 7
<211> LENGTH: 4
<212> TYPE: PRT
<213> ORGANISM: Artificial Sequence
<220> FEATURE:
<223> OTHER INFORMATION: heterologous protease cleavage sites recognized
      by furin protease
<220> FEATURE:
<221> NAME/KEY: VARIANT
<222> LOCATION: 2,3
<223> OTHER INFORMATION: Xaa = any amino acid

<400> SEQUENCE: 7

Arg Xaa Xaa Arg
1

<210> SEQ ID NO 8
<211> LENGTH: 6
<212> TYPE: PRT
<213> ORGANISM: Artificial Sequence
<220> FEATURE:
<223> OTHER INFORMATION: heterologous protease cleavage sites recognized
      by thrombin protease
<220> FEATURE:
<221> NAME/KEY: VARIANT
<222> LOCATION: 1,2
<223> OTHER INFORMATION: Xaa = hydrophobic amino acids
<220> FEATURE:
<221> NAME/KEY: VARIANT
<222> LOCATION: 5,6
<223> OTHER INFORMATION: Xaa = nonacidic amino acids
```

<400> SEQUENCE: 8

Xaa Xaa Pro Arg Xaa Xaa
1               5

<210> SEQ ID NO 9
<211> LENGTH: 1847
<212> TYPE: DNA
<213> ORGANISM: Artificial Sequence
<220> FEATURE:
<223> OTHER INFORMATION: AG32 huIL15opt - nucleic acid construct
      encoding optimized human IL-15

<400> SEQUENCE: 9

| | | | | | | |
|---|---|---|---|---|---|---|
| cctggccatt | gcatacgttg | tatccatatc | ataatatgta | catttatatt | ggctcatgtc | 60 |
| caacattacc | gccatgttga | cattgattat | tgactagtta | ttaatagtaa | tcaattacgg | 120 |
| ggtcattagt | tcatagccca | tatatggagt | tccgcgttac | ataacttacg | gtaaatggcc | 180 |
| cgcctggctg | accgcccaac | gacccccgcc | cattgacgtc | aataatgacg | tatgttccca | 240 |
| tagtaacgcc | aatagggact | ttccattgac | gtcaatgggt | ggagtattta | cggtaaactg | 300 |
| cccacttggc | agtacatcaa | gtgtatcata | tgccaagtac | gccccctatt | gacgtcaatg | 360 |
| atggtaaatg | gcccgcctgg | cattatgccc | agtacatgac | cttatgggac | tttcctactt | 420 |
| ggcagtacat | ctacgtatta | gtcatcgcta | ttaccatggt | gatgcggttt | tggcagtaca | 480 |
| tcaatgggcg | tggatagcgg | tttgactcac | ggggatttcc | aagtctccac | cccattgacg | 540 |
| tcaatgggag | tttgttttgg | caccaaaatc | aacgggactt | tccaaaatgt | cgtaacaact | 600 |
| ccgccccatt | gacgcaaatg | ggcggtaggc | gtgtacggtg | ggaggtctat | ataagcagag | 660 |
| ctcgtttagt | gaaccgtcag | atcgcctgga | gacgccatcc | acgctgtttt | gacctccata | 720 |
| gaagacaccg | ggaccgatcc | agcctccgcg | ggcgcgcgtc | gacaagaaat | gcggatctcg | 780 |
| aagccgcacc | tgcggtcgat | atcgatccag | tgctacctgt | gcctgctcct | gaactcgcac | 840 |
| ttcctcacgg | aggccggtat | acacgtcttc | atcctgggct | gcttctcggc | ggggctgccg | 900 |
| aagacggagg | cgaactgggt | gaacgtgatc | tcggacctga | agaagatcga | ggacctcatc | 960 |
| cagtcgatgc | acatcgacgc | gacgctgtac | acggagtcgg | acgtccaccc | gtcgtgcaag | 1020 |
| gtcacggcga | tgaagtgctt | cctcctggag | ctccaagtca | tctcgctcga | gtcgggggac | 1080 |
| gcgtcgatcc | acgacacggt | ggagaacctg | atcatcctgg | cgaacaactc | gctgtcgtcg | 1140 |
| aacgggaacg | tcacggagtc | gggctgcaag | gagtgcgagg | agctggagga | agaagaacatc | 1200 |
| aaggagttcc | tgcagtcgtt | cgtgcacatc | gtccagatgt | tcatcaacac | gtcgtgaggg | 1260 |
| cccggcgcgc | cgaattcgcg | gatatcggtt | aacggatcca | gatctgctgt | gccttctagt | 1320 |
| tgccagccat | ctgttgtttg | cccctccccc | gtgccttcct | tgaccctgga | aggtgccact | 1380 |
| cccactgtcc | tttcctaata | aaatgaggaa | attgcatcgc | attgtctgag | taggtgtcat | 1440 |
| tctattctgg | ggggtggggt | ggggcaggac | agcaagggg | aggattggga | agacaatagc | 1500 |
| aggcatgctg | gggatgcggt | gggctctatg | gtacccagg | tgctgaagaa | ttgacccggt | 1560 |
| tcctcctggg | ccagaaagaa | gcaggcacat | ccccttctct | gtgacacacc | ctgtccacgc | 1620 |
| ccctggttct | tagttccagc | cccactcata | ggacactcat | agctcaggag | gctccgcct | 1680 |
| tcaatcccac | ccgctaaagt | acttggagcg | gtctctccct | ccctcatcag | cccaccaaac | 1740 |
| caaacctagc | ctccaagagt | gggaagaaat | taaagcaaga | taggctatta | agtgcagagg | 1800 |
| gagagaaaat | gcctccaaca | tgtgaggaag | taatgagaga | aatcata | | 1847 |

-continued

<210> SEQ ID NO 10
<211> LENGTH: 162
<212> TYPE: PRT
<213> ORGANISM: Artificial Sequence
<220> FEATURE:
<223> OTHER INFORMATION: AG32 huIL15opt - amino acid sequence of
      optimized human IL-15

<400> SEQUENCE: 10

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 11
<211> LENGTH: 1808
<212> TYPE: DNA
<213> ORGANISM: Artificial Sequence
<220> FEATURE:
<223> OTHER INFORMATION: AG59  CMV huIL15tPA6 - nucleic acid construct
      encoding optimized human IL-15

<400> SEQUENCE: 11

```
cctggccatt gcatacgttg tatccatatc ataatatgta catttatatt ggctcatgtc     60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
atggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccgtcag atcgcctgga gacgccatcc acgctgtttt gacctccata    720
gaagacaccg ggaccgatcc agcctccgcg gccgcgcgtc gacaagaaat ggatgcaatg    780
```

```
aagagagggc tctgctgtgt gctgctgctg tgtggagcag tcttcgtttc gcccagccag    840
gaaatccatg cccgattcag aagaggagcc agaaactggg tgaacgtgat ctcggacctg    900
aagaagatcg aggacctcat ccagtcgatg cacatcgacg cgacgctgta cacggagtcg    960
gacgtccacc cgtcgtgcaa ggtcacggcg atgaagtgct tcctcctgga gctccaagtc   1020
atctcgctcg agtcggggga cgcgtcgatc cacgacacgg tggagaacct gatcatcctg   1080
gcgaacaact cgctgtcgtc gaacgggaac gtcacggagt cgggctgcaa ggagtgcgag   1140
gagctggagg agaagaacat caaggagttc ctgcagtcgt tcgtgcacat cgtccagatg   1200
ttcatcaaca cgtcgtgagg gcccggcgcg ccgaattcgc ggatatcggt taacggatcc   1260
agatctgctg tgccttctag ttgccagcca tctgttgttt gcccctcccc cgtgccttcc   1320
ttgaccctgg aaggtgccac tcccactgtc ctttcctaat aaaatgagga aattgcatcg   1380
cattgtctga gtaggtgtca ttctattctg ggggtgggg  tggggcagga cagcaagggg   1440
gaggattggg aagacaatag caggcatgct ggggatgcgg tgggctctat gggtacccag   1500
gtgctgaaga attgacccgg ttcctcctgg gccagaaaga agcaggcaca tccccttctc   1560
tgtgacacac cctgtccacg cccctggttc ttagttccag ccccactcat aggacactca   1620
tagctcagga gggctccgcc ttcaatccca cccgctaaag tacttggagc ggtctctccc   1680
tccctcatca gcccaccaaa ccaaacctag cctccaagag tgggaagaaa ttaaagcaag   1740
ataggctatt aagtgcagag ggagagaaaa tgcctccaac atgtgaggaa gtaatgagag   1800
aaatcata                                                            1808
```

<210> SEQ ID NO 12
<211> LENGTH: 149
<212> TYPE: PRT
<213> ORGANISM: Artificial Sequence
<220> FEATURE:
<223> OTHER INFORMATION: AG59 CMV huIL15tPA6 - amino acid sequence of optimized human IL-15

<400> SEQUENCE: 12

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Asn Trp Val Asn Val Ile Ser Asp Leu Lys Lys Ile Glu
        35                  40                  45

Asp Leu Ile Gln Ser Met His Ile Asp Ala Thr Leu Tyr Thr Glu Ser
    50                  55                  60

Asp Val His Pro Ser Cys Lys Val Thr Ala Met Lys Cys Phe Leu Leu
65                  70                  75                  80

Glu Leu Gln Val Ile Ser Leu Glu Ser Gly Asp Ala Ser Ile His Asp
                85                  90                  95

Thr Val Glu Asn Leu Ile Ile Leu Ala Asn Asn Ser Leu Ser Ser Asn
            100                 105                 110

Gly Asn Val Thr Glu Ser Gly Cys Lys Glu Cys Glu Glu Leu Glu Glu
        115                 120                 125

Lys Asn Ile Lys Glu Phe Leu Gln Ser Phe Val His Ile Val Gln Met
    130                 135                 140

Phe Ile Asn Thr Ser
145
```

<210> SEQ ID NO 13

<211> LENGTH: 2140
<212> TYPE: DNA
<213> ORGANISM: Artificial Sequence
<220> FEATURE:
<223> OTHER INFORMATION: AG79 huIL15Ra - nucleic acid construct encoding
      optimized human IL-15Ra

<400> SEQUENCE: 13

| | | | | | | |
|---|---|---|---|---|---|---|
| cctggccatt | gcatacgttg | tatccatatc | ataatatgta | catttatatt | ggctcatgtc | 60 |
| caacattacc | gccatgttga | cattgattat | tgactagtta | ttaatagtaa | tcaattacgg | 120 |
| ggtcattagt | tcatagccca | tatatggagt | tccgcgttac | ataacttacg | gtaaatggcc | 180 |
| cgcctggctg | accgcccaac | gacccccgcc | cattgacgtc | aataatgacg | tatgttccca | 240 |
| tagtaacgcc | aatagggact | ttccattgac | gtcaatgggt | ggagtattta | cggtaaactg | 300 |
| cccacttggc | agtacatcaa | gtgtatcata | tgccaagtac | gccccctatt | gacgtcaatg | 360 |
| atggtaaatg | gcccgcctgg | cattatgccc | agtacatgac | cttatgggac | tttcctactt | 420 |
| ggcagtacat | ctacgtatta | gtcatcgcta | ttaccatggt | gatgcggttt | tggcagtaca | 480 |
| tcaatgggcg | tggatagcgg | tttgactcac | ggggatttcc | aagtctccac | cccattgacg | 540 |
| tcaatggag | tttgttttgg | caccaaaatc | aacgggactt | tccaaaatgt | cgtaacaact | 600 |
| ccgccccatt | gacgcaaatg | gcggtaggc | gtgtacggtg | ggaggtctat | ataagcagag | 660 |
| ctcgtttagt | gaaccgtcag | atcgcctgga | gacgccatcc | acgctgtttt | gacctccata | 720 |
| gaagacaccg | ggaccgatcc | agcctccgcg | gcgcgcgtc | gacgctagca | agaaatggcc | 780 |
| ccgaggcggg | cgcgaggctg | ccggacccctc | ggtctcccgg | cgctgctact | gctcctgctg | 840 |
| ctccggccgc | cggcgacgcg | gggcatcacg | tgcccgcccc | ccatgtccgt | ggagcacgca | 900 |
| gacatctggg | tcaagagcta | cagcttgtac | tcccgggagc | ggtacatctg | caactcgggt | 960 |
| ttcaagcgga | aggccggcac | gtccagcctg | acggagtgcg | tgttgaacaa | ggccacgaat | 1020 |
| gtcgcccact | ggacgacccc | ctcgctcaag | tgcatccgcg | acccggccct | ggttcaccag | 1080 |
| cggcccgcgc | caccctccac | cgtaacgacg | gcggggtga | ccccgcagcc | ggagagcctc | 1140 |
| tcccgtcgg | gaaaggagcc | cgccgcgtcg | tcgcccagct | cgaacaacac | ggcggccaca | 1200 |
| actgcagcga | tcgtcccggg | ctcccagctg | atgccgtcga | agtcgccgtc | cacgggaacc | 1260 |
| acggagatca | gcagtcatga | gtcctcccac | ggcacccccct | cgcaaacgac | ggccaagaac | 1320 |
| tgggaactca | cggcgtccgc | ctcccaccag | ccgccggggg | tgtatccgca | aggccacagc | 1380 |
| gacaccacgg | tggcgatctc | cacgtccacg | gtcctgctgt | gtgggctgag | cgcggtgtcg | 1440 |
| ctcctggcgt | gctacctcaa | gtcgaggcag | actccccgc | tggccagcgt | tgagatggag | 1500 |
| gccatggagg | ctctgccggt | gacgtggggg | accagcagca | gggatgagga | cttggagaac | 1560 |
| tgctcgcacc | acctataatg | agaattcgat | ccagatctgc | tgtgccttct | agttgccagc | 1620 |
| catctgttgt | ttgcccctcc | cccgtgcctt | ccttgaccct | ggaaggtgcc | actcccactg | 1680 |
| tcctttccta | ataaaatgag | gaaattgcat | cgcattgtct | gagtaggtgt | cattctattc | 1740 |
| tggggggtgg | ggtggggcag | gacagcaagg | gggaggattg | ggaagacaat | agcaggcatg | 1800 |
| ctggggatgc | ggtgggctct | atgggtaccc | aggtgctgaa | gaattgaccc | ggttcctcct | 1860 |
| gggccagaaa | gaagcaggca | catccccttc | tctgtgacac | accctgtcca | cgcccctggt | 1920 |
| tcttagttcc | agccccactc | ataggacact | catagctcag | gagggctccg | ccttcaatcc | 1980 |
| cacccgctaa | agtacttgga | gcggtctctc | cctccctcat | cagcccacca | aaccaaacct | 2040 |
| agcctccaag | agtgggaaga | aattaaagca | agataggcta | ttaagtgcag | agggagagaa | 2100 | aatgcctcca acatgtgagg aagtaatgag agaaatcata                                2140

<210> SEQ ID NO 14
<211> LENGTH: 267
<212> TYPE: PRT
<213> ORGANISM: Artificial Sequence
<220> FEATURE:
<223> OTHER INFORMATION: AG79 huIL15Ra - amino acid sequence of
      optimized human IL-15Ra

<400> SEQUENCE: 14

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265

<210> SEQ ID NO 15
<211> LENGTH: 1971
<212> TYPE: DNA
<213> ORGANISM: Artificial Sequence
<220> FEATURE:
<223> OTHER INFORMATION: AG98 CMV hu sIL15Ra - nucleic acid construct
      encoding optimized human IL-15Ra

<400> SEQUENCE: 15
cctggccatt gcatacgttg tatccatatc ataatatgta catttatatt ggctcatgtc     60
caacattacc gccatgttga cattgattat tgactagtta ttaatagtaa tcaattacgg    120

| ggtcattagt tcatagccca tatatggagt tccgcgttac ataacttacg gtaaatggcc | 180 |
| cgcctggctg accgcccaac gaccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| atggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg gcggtaggc gtgtacggtg ggaggtctat ataagcagag | 660 |
| ctcgtttagt gaaccgtcag atcgcctgga gacgccatcc acgctgtttt gacctccata | 720 |
| gaagacaccg ggaccgatcc agcctccgcg ggcgcgtc gacgctagca agaaatggcc | 780 |
| ccgaggcggg cgcgaggctg ccggaccctc ggtctcccgg cgctgctact gctcctgctg | 840 |
| ctccggccgc cggcgacgcg gggcatcacg tgcccgcccc ccatgtccgt ggagcacgca | 900 |
| gacatctggg tcaagagcta cagcttgtac tcccgggagc ggtacatctg caactcgggt | 960 |
| ttcaagcgga aggccggcac gtccagcctg acggagtgcg tgttgaacaa ggccacgaat | 1020 |
| gtcgcccact ggacgacccc ctcgctcaag tgcatccgcg acccggccct ggttcaccag | 1080 |
| cggcccgcgc accctccac cgtaacgacg gcggggtga ccccgcagcc ggagagcctc | 1140 |
| tccccgtcgg gaaaggagcc cgccgcgtcg tcgcccagct cgaacaacac ggcggccaca | 1200 |
| actgcagcga tcgtcccggg ctcccagctg atgccgtcga gtcgccgtc cacgggaacc | 1260 |
| acggagatca gcagtcatga gtcctcccac ggcaccccct cgcaaacgac ggccaagaac | 1320 |
| tgggaactca cggcgtccgc ctcccaccag ccgccggggg tgtatccgca aggccacagc | 1380 |
| gacaccacgt aatgagaatt cgcggatatc ggttaacgga tccagatctg ctgtgccttc | 1440 |
| tagttgccag ccatctgttg tttgcccctc cccgtgcct tccttgaccc tggaaggtgc | 1500 |
| cactcccact gtcctttcct aataaaatga ggaaattgca tcgcattgtc tgagtaggtg | 1560 |
| tcattctatt ctggggggtg gggtggggca ggacagcaag ggggaggatt gggaagacaa | 1620 |
| tagcaggcat gctggggatg cggtgggctc tatgggtacc caggtgctga agaattgacc | 1680 |
| cggttcctcc tgggccagaa agaagcaggc acatcccctt ctctgtgaca cccctgtcc | 1740 |
| acgcccctgg ttcttagttc cagccccact cataggacac tcatagctca ggagggctcc | 1800 |
| gccttcaatc ccaccgcta aagtacttgg agcggtctct ccctcctca tcagcccacc | 1860 |
| aaaccaaacc tagcctccaa gagtgggaag aaattaaagc aagataggct attaagtgca | 1920 |
| gagggagaga aaatgcctcc aacatgtgag gaagtaatga gagaaatcat a | 1971 |

<210> SEQ ID NO 16
<211> LENGTH: 205
<212> TYPE: PRT
<213> ORGANISM: Artificial Sequence
<220> FEATURE:
<223> OTHER INFORMATION: AG98 CMV hu sIL15Ra - amino acid sequence of optimized human IL-15Ra

<400> SEQUENCE: 16

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

```
Cys Pro Pro Met Ser Val Glu His Ala Asp Ile Trp Val Lys Ser
         35                  40                  45

Tyr Ser Leu Tyr Ser Arg Glu Arg Tyr Ile Cys Asn Ser Gly Phe Lys
 50                  55                  60

Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys Ile Arg Asp
                 85                  90                  95

Pro Ala Leu Val His Gln Arg Pro Ala Pro Pro Ser Thr Val Thr Thr
                100                 105                 110

Ala Gly Val Thr Pro Gln Pro Glu Ser Leu Ser Pro Ser Gly Lys Glu
            115                 120                 125

Pro Ala Ala Ser Ser Pro Ser Ser Asn Asn Thr Ala Ala Thr Thr Ala
        130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
                180                 185                 190

Pro Pro Gly Val Tyr Pro Gln Gly His Ser Asp Thr Thr
            195                 200                 205

<210> SEQ ID NO 17
<211> LENGTH: 1754
<212> TYPE: DNA
<213> ORGANISM: Artificial Sequence
<220> FEATURE:
<223> OTHER INFORMATION: AG151 huIL-15 huGM-CSF - nucleic acid construct
      encoding optimized human IL-15 with a signal peptide of human
      GM-CSF

<400> SEQUENCE: 17
cctggccatt gcatacgttg tatccatatc ataatatgta catttatatt ggctcatgtc       60
caacattacc gccatgttga cattgattat tgactagtta ttaatagtaa tcaattacgg      120
ggtcattagt tcatagccca tatatggagt tccgcgttac ataacttacg gtaaatggcc      180
cgcctggctg accgcccaac gacccccgcc cattgacgtc aataatgacg tatgttccca      240
tagtaacgcc aatagggact ttccattgac gtcaatgggt ggagtattta cggtaaactg      300
cccacttggc agtacatcaa gtgtatcata tgccaagtac gccccctatt gacgtcaatg      360
atggtaaatg gcccgcctgg cattatgccc agtacatgac cttatgggac tttcctactt      420
ggcagtacat ctacgtatta gtcatcgcta ttaccatggt gatgcggttt tggcagtaca      480
tcaatgggcg tggatagcgg tttgactcac ggggatttcc aagtctccac cccattgacg      540
tcaatgggag tttgttttgg caccaaaatc aacgggactt tccaaaatgt cgtaacaact      600
ccgccccatt gacgcaaatg gcggtaggc gtgtacggtg gaggtctat ataagcagag       660 ctcgtttagt gaaccgtcag atcgcctgga gacgccatcc acgctgtttt gacctccata      720
gaagacaccg ggaccgatcc agcctccgcg ggcgcgcgtc gacaagaaat gtggctccag      780
agcctgctac tcctggggac ggtggcctgc agcatctcga actgggtgaa cgtgatctcg      840
gacctgaaga gatcgagga cctcatccag tcgatgcaca tcgacgcgac gctgtacacg      900
gagtcggacg tccacccgtc gtgcaaggtc acgcgcgatga agtgcttcct cctggagctc      960
caagtcatct cgctcgagtc gggggacgcg tcgatccacg acacggtgga gaacctgatc     1020
```

```
atcctggcga caaactcgct gtcgtcgaac gggaacgtca cggagtcggg ctgcaaggag    1080
tgcgaggagc tggaggagaa gaacatcaag gagttcctgc agtcgttcgt gcacatcgtc    1140
cagatgttca tcaacacgtc gtgagggccc ggcgcgccga attcgcggat atcggttaac    1200
ggatccagat ctgctgtgcc ttctagttgc cagccatctg ttgtttgccc ctcccccgtg    1260
ccttccttga ccctggaagg tgccactccc actgtccttt cctaataaaa tgaggaaatt    1320
gcatcgcatt gtctgagtag gtgtcattct attctggggg gtggggtggg gcaggacagc    1380
aagggggagg attgggaaga caatagcagg catgctgggg atgcggtggg ctctatgggt    1440
acccaggtgc tgaagaattg acccggttcc tcctgggcca gaaagaagca ggcacatccc    1500
cttctctgtg acacaccctg tccacgcccc tggttcttag ttccagcccc actcatagga    1560
cactcatagc tcaggagggc tccgccttca atcccacccg ctaaagtact tggagcggtc    1620
tctccctccc tcatcagccc accaaaccaa acctagcctc caagagtggg aagaaattaa    1680
agcaagatag gctattaagt gcagagggag agaaaatgcc tccaacatgt gaggaagtaa    1740
tgagagaaat cata                                                      1754

<210> SEQ ID NO 18
<211> LENGTH: 131
<212> TYPE: PRT
<213> ORGANISM: Artificial Sequence
<220> FEATURE:
<223> OTHER INFORMATION: AG151 huIL-15 huGM-CSF - amino acid sequence of
      optimized human IL-15 with a signal peptide of human GM-CSF

<400> SEQUENCE: 18

Met Trp Leu Gln Ser Leu Leu Leu Leu Gly Thr Val Ala Cys Ser Ile
1               5                   10                  15

Ser Asn Trp Val Asn Val Ile Ser Asp Leu Lys Lys Ile Glu Asp Leu
            20                  25                  30

Ile Gln Ser Met His Ile Asp Ala Thr Leu Tyr Thr Glu Ser Asp Val
        35                  40                  45

His Pro Ser Cys Lys Val Thr Ala Met Lys Cys Phe Leu Leu Glu Leu
    50                  55                  60

Gln Val Ile Ser Leu Glu Ser Gly Asp Ala Ser Ile His Asp Thr Val
65                  70                  75                  80

Glu Asn Leu Ile Ile Leu Ala Asn Asn Ser Leu Ser Ser Asn Gly Asn
                85                  90                  95

Val Thr Glu Ser Gly Cys Lys Glu Cys Glu Glu Leu Glu Glu Lys Asn
            100                 105                 110

Ile Lys Glu Phe Leu Gln Ser Phe Val His Ile Val Gln Met Phe Ile
        115                 120                 125

Asn Thr Ser
    130
```

COMPLEXES OF IL-15 AND IL-15RALPHA AND USES THEREOF

RELATED APPLICATIONS

This application claims the benefit of U.S. Provisional Application No. 60/937,471 filed Jun. 27, 2007, which is incorporated by reference herein in its entirety.

GOVERNMENTAL INTERESTS

This invention was created in the performance of a Cooperative Research and Development Agreement with the National Institutes of Health, an Agency of the Department of Health and Human Services. The Government of the United States has certain rights in this invention.

1. FIELD OF THE INVENTION

The present invention relates to Therapeutic Agents that modulate IL-15-mediated function for the prevention, treatment and/or management of diseases involving IL-15-mediated signaling, including, but not limited to cancer, infectious disease, autoimmune disease, and transplantation rejection.

2. BACKGROUND OF THE INVENTION

The cytokine, interleukin-15 (IL-15), is a member of the four alpha-helix bundle family of lymphokines produced by many cells in the body. IL-15 plays a pivotal role in modulating the activity of both the innate and adaptive immune system, e.g., maintenance of the memory T-cell response to invading pathogens, inhibition of apoptosis, activation of dendritic cells, and induction of Natural Killer (NK) cell proliferation and cytotoxic activity.

The IL-15 receptor consists of three polypeptides, the type-specific IL-15 receptor alpha ("IL-15Ra"), the IL-2/IL-15 receptor beta (or CD122) ("β"), and the common gamma chain (or CD132) ("γ") that is shared by multiple cytokine receptors. The IL-15Ra is thought to be expressed by a wide variety of cell types, but not necessarily in conjunction with β and γ. IL-15 signaling has been shown to occur through the heterodimeric complex of IL-15Ra, β, and γ; through the heterodimeric complex of β and γ, or through a subunit, IL-15RX, found on mast cells.

IL-15 is a soluble protein, but endogenous IL-15 is not readily detectable in serum or body fluids—instead, it occurs predominantly as a membrane-bound form that is expressed or acquired by several types of accessory cells. For instance, although IL-15 mRNA is detected in cells of both hematopoietic and non-hemaptopoietic lineage, T cells do not produce IL-15. Instead, IL-15 binds to the IL-15Ra, forming cell-surface complexes on T cells. IL-15 specifically binds to the IL-15Ra with high affinity via the "sushi domain" in exon 2 of the extracellular domain of the receptor. After trans-endosomal recycling and migration back to the cell surface, these IL-15 complexes acquire the property to activate bystander cells expressing the IL-15R βγ low-affinity receptor complex, inducing IL-15-mediated signaling via the Jak/Stat pathway. A naturally occurring soluble form of IL-15Ra ("sIL-15Ra"), which is cleaved at a cleavage site in the extracellular domain immediately distal to the transmembrane domain of the receptor has been observed. Tumor necrosis factor-alpha-converting enzyme (TACE/ADAM17) has been implicated as a protease involved in this process.

Based on its multifaceted role in the immune system, various therapies designed to modulate IL-15-mediated function have been explored. For example, the administration of exogenous IL-15 can enhance the immune function of patients infected with human inmmunodeficiency virus (HIV). In keeping with its immune enhancing activity, increased expression of endogenous IL-15 is observed in patients with autoimmune diseases, e.g., rheumatoid arthritis, multiple sclerosis, ulcerative colitis, and psoriasis. Because some studies reported that the soluble form of the IL-15Ra (sIL-15Ra) is an antagonist of IL-15-mediated signaling, the sIL-15Ra has been explored for treating autoimmune inflammatory diseases. Nevertheless, recent reports suggest that IL-15, when complexed with the sIL-15Ra, or the sushi domain, maintains its immune enhancing function.

Despite the amount of progress made in understanding the function of IL-15, it is unclear how various forms of the IL-15Ra, alone or when complexed to IL-15, can be used to modulate IL-15 function as part of a therapeutic regimen.

3. SUMMARY OF THE INVENTION

The present invention relates to agents that modulate interleukin-15 ("IL-15") signal transduction or function ("Therapeutic Agents") and the use of those agents to modulate immune function. The Therapeutic Agents target the interaction between IL-15 and its receptor and modulate IL-15-induced signal transduction. The Therapeutic Agents may be formulated with polymers, such as poly-β-1→4-N-acetylglucosamine, for administration to a human subject to modulate IL-15-mediated immune function.

The present invention provides Therapeutic Agents that induce IL-15 signal transduction and enhance IL-15-mediated immune function (i.e., Agonistic Therapeutic Agents). The Agonistic Therapeutic Agents are useful for enhancing IL-15-mediated immune function in a subject in need of such therapy. In particular, the Agonistic Therapeutic Agents are useful for the prevention, treatment and/or management of disorders in which it is beneficial to enhance IL-15-mediated immune function. Non-limiting examples of such disorders include cancer and infectious diseases. In a specific embodiment, the invention provides a method for treating a cancer or an infectious disease in a human subject, comprising administering to a human subject in need thereof an effective amount of an Agonistic Therapeutic Agent.

The Agonistic Therapeutic Agents include complexes that bind to the βγ subunits of the IL-15 receptor and comprise IL-15 covalently or noncovalently bound to interleukin-15 receptor alpha ("IL-15Ra") ("IL-S/IL-15Ra complexes"). The IL-15/IL-15Ra complex may comprise native IL-15 or an IL-15 derivative covalently or noncovalently bound to native IL-15Ra or an IL-15Ra derivative. In one embodiment, the IL-15/IL-15Ra complex comprises an IL-15Ra derivative and the IL-15Ra derivative is a soluble form of the native IL-15Ra. In another embodiment, the IL-15/IL-15Ra complex comprises an IL-15Ra derivative and the IL-15Ra derivative comprises mutations that inhibits cleavage by an endogenous protease. In a specific embodiment, the extracellular domain cleavage site of IL-15Ra is replaced with a cleavage site that is specifically recognized by a heterologous protease. In a specific embodiment, the extracellular domain cleavage site of IL-15Ra that is cleaved by an endogenous processing enzyme is replaced with a heterologous domain (e.g., heterologous transmembrane domain) or a synthetic amino acid sequence that does not allow cleavage and generation of soluble IL-15Ra. In certain embodiments, the extracellular domain cleavage site of IL-15Ra that is cleaved by an endogenous processing enzyme is mutated to inhibit cleavage and generation of soluble IL-15Ra. In one embodiment, the extracellular domain cleavage site of IL-15Ra is replaced with a heterologous extracellular domain cleavage site (e.g., heterologous transmembrane domain that is recognized and cleaved by another enzyme unrelated to the endogenous processing enzyme that cleaves the IL-15Ra).

In addition to IL-15 and IL-15Ra, the IL-15/IL-15Ra complexes may comprise a heterologous molecule. The heterologous molecule may be conjugated to IL-15 and/or IL-15Ra. The heterologous molecule is conjugated to IL-15 or IL-15Ra in a manner that does not interfere or prevent IL-15 and IL-15Ra from binding to one another and does not interfere or prevent the interaction between the IL-15/IL-15Ra complex and the βγ subunits of the IL-15 receptor. In some embodiments, the heterologous molecule is an antigen associated with a disease that one intends to prevent, treat and/or manage. Non-limiting examples of such antigens include viral antigens, bacterial antigens, parasitic antigens, and tumor antigens. In other embodiments, the heterologous molecule is an antibody that specifically binds to an antigen associated with a disease that one intends to prevent, treat and/or manage. In some embodiments, the antibody specifically binds to a cellular antigen (e.g., a receptor) expressed by a cell that one desires to target. In some embodiments, the heterologous molecule increases protein stability. In certain embodiments, the heterologous molecule is an Fc domain of an immunoglobulin or a fragment thereof. In other embodiments, the heterologous molecules is not an Fc domain of an immunoglobulin molecule or a fragment thereof.

The IL-15/IL-15Ra complexes may be formulated for administration to a human subject to enhance an IL-15-mediated immune function. In a specific embodiment, the IL-15/IL-15Ra complexes are formulated with a polymer, such as poly-β1-→4-N-acetylglucosamine, for administration to a subject (preferably, a human subject). The IL-15/IL-15Ra complexes may also be administered to a non-human subject for veterinary uses and/or to produce antibodies that specifically bind to IL-15/IL-15Ra complexes.

In specific embodiments, the present invention encompasses a method for enhancing an IL-15-mediated immune function in a human subject, comprising administering to a human subject in need thereof a composition comprising an effective amount of an IL-15/IL-15Ra complex formulated with a poly-β-1→4-N-acetylglucosamine polymer, wherein the IL-15/IL-15Ra complex comprises human IL-15 or a derivative thereof covalently or noncovalently linked to human IL-15Ra or a derivative thereof. In a further embodiment, the IL-15/IL-15Ra complex comprises human IL-15 and human IL-15Ra. In another embodiment, the IL-15/IL-15Ra complex comprises human IL-15 and a human IL-15Ra derivative. In yet another embodiment, the human IL-15Ra or human IL-15Ra derivative is soluble. In a particular embodiment, the method further comprises administering to the human subject one or more other therapeutic polypeptides (e.g., cytokines or growthfactors) or therapy.

The Agonistic Therapeutic Agents also include nucleic acids encoding IL-15 and IL-15Ra that when expressed produce IL-15/IL-15Ra complexes, and cells engineered to recombinantly express IL-15/IL-15Ra complexes by introducing nucleic acids encoding IL-15 and IL-15Ra into the cells. The nucleic acids may be administered to a subject (preferably, a human subject) as part of a gene therapy protocol. In a specific embodiment, the nucleic acids are formulated with a polymer, such as poly-β-1→4-N-acetylglucosamine, for administration to a subject (preferably, a human subject). Alternatively, the nucleic acids may be transfected (in a specific embodiment, stably transfected) into cells to produce large quantities of IL-15/IL-15Ra complex suitable for in vitro and/or in vivo uses. In one embodiment, the cells engineered to express the nucleic acids are cell lines. In another embodiment, the cells engineered to express the nucleic acids are primary cells from a subject (preferably, a human subject). In a specific embodiment, the cells engineered to express the nucleic acids are cancer cells or cells infected with a pathogen.

Cells engineered to express IL-15 and IL-15Ra may be used to generate large quantities of IL-15/IL-15Ra complex suitable for in vitro and in vivo uses. Cells engineered to express IL-15 and IL-15Ra may also be administered to a subject (preferably, a human subject) as part of a gene therapy protocol. In a specific embodiment, irradiated cancer cells engineered to express IL-15 and IL-15Ra are administered to a cancer patient. In a particular embodiment, cells engineered to express IL-15/IL-15Ra complexes are formulated for administration to a human subject to enhance an IL-15-mediated immune function. In another embodiment, the cells engineered to express IL-15/IL-15Ra complexes are formulated with a polymer, such as poly-β-1β4-N-acetylglucosamine, for administration to a subject (preferably, a human subject). The present invention also relates to an irradiated cancer cell recombinantly expressing human IL-15 and human IL-15Ra produced by a method described herein, and a pharmaceutical composition comprising an irradiated cancer cell described herein. In a particular embodiment, the pharmaceutical composition comprises an irradiated cancer cell formulated with a poly-β-1→4-N-acetylglucosamine polymer.

One aspect of the present invention relates to a method for making irradiated cancer cells recombinantly expressing human IL-15 and human IL-15Ra, said method comprises the steps of: (i) isolating cancer cells from a subject diagnosed with cancer; (ii) introducing a nucleic acid construct(s) encoding recombinant human IL-15 or a derivative thereof and human IL-15Ra or a derivative thereof; and (iii) irradiating said cancer cells. In a particular embodiment, the human IL-15Ra or human IL-15 Ra derivative is soluble.

In specific embodiments, the present invention provides for a cell that recombinantly expresses a mammalian IL-15 or a derivative thereof and a mammalian IL-15Ra or a derivative thereof, wherein the cell expresses at least 0.6 pg of mammalian IL-15 or a derivative thereof. In particular embodiments, the cell expressing at least 0.6 pg of mammalian IL-15 or a derivative thereof grows in serum-free media.

The present invention relates to a method for treating cancer in a human subject, comprising administering to a human subject in need thereof a composition comprising irradiated cancer cells engineered to recombinantly co-express (i) human IL-15 or a derivative thereof, and (ii) human IL-15Ra or a derivative thereof. In a particular embodiment, the cancer cells are obtained by isolating cancer cells from the subject. In a further embodiment, the irradiated cancer cells are obtained by engineering cancer cells to recombinantly co-express human IL-15 or a derivative thereof and human IL-15Ra or a derivative thereof (prior to irradiation). In another embodiment, the irradiated cancer cells are obtained by engineering cancer cells to recombinantly co-express human IL-15 and a human IL-15Ra derivative (prior to irradiation). In yet another embodiment, the human IL-15Ra or human IL-15Ra derivative is soluble. In a certain embodiment, the irradiated cancer cells further recombinantly express one or more other therapeutic polypeptides (e.g., cytokines or growthfactors).

The present invention also provides Therapeutic Agents that reduce or inhibit IL-15 signal transduction and suppress IL-15-mediated immune function (i.e., Antagonistic Therapeutic Agents"). The Antagonistic Therapeutic Agents include antibodies that specifically bind to an IL-15/IL-15Ra complex and prevent endogenous IL-15/IL-15Ra complexes from binding to the βγ subunits of the IL-15 receptor, and cells engineered to express such antibodies. The Antagonistic Therapeutic Agents are useful for suppressing IL-15-mediated immune function in a subject in need of such therapy. In particular, the Antagonistic Therapeutic Agents are useful for the prevention, treatment and/or management of disorders in which it is beneficial to suppress IL-15-mediated immune function. Non-limiting examples of such disorders include autoimmune disorders, graft versus host disease, transplantation rejection, and inflammatory disorders. In a specific embodiment, the invention provides a method for treating an autoimmune disorder or inflammatory disorder in a human subject, comprising administering to a human subject in need thereof an effective amount of an antibody that specifically binds to endogenous IL-15/IL-15Ra complexes. In a further embodiment, the antibody specifically binds to endogenous IL-15/IL-15Ra complexes and does not specifically bind to IL-15 alone or IL-15Ra alone when not complexed to each other. In specific embodiments, the present invention relates to a method for treating an autoimmune disorder or inflammatory disorder in a human subject, comprising administering to a human subject in need thereof an effective amount of an antibody that specifically binds to IL-15/IL-15Ra complexes and reduces the binding of the IL-15/IL-15Ra complexes to the beta-gamma receptor complex as determined in cell culture or in vitro. In a further embodiment of the method, the antibody is a monoclonal humanized antibody.

3.1. Terminology

As used herein, the terms "about" and "approximately," when used to a modify numeric value or numeric range, indicate that reasonable deviations from the value or range, typically 5% or 10% above and 5% or 10% below the value or range, remain within the intended meaning of the recited value or range.

As used herein, the terms "antibody" and "antibodies" refer to molecules that contain an antigen binding site, e.g., immunoglobulins. Antibodies include, but are not limited to, monoclonal antibodies, multispecific antibodies, human antibodies, humanized antibodies, synthetic antibodies, chimeric antibodies, polyclonal antibodies, single domain antibodies, camelized antibodies, single-chain Fvs (scFv), single chain antibodies, Fab fragments, F(ab') fragments, disulfide-linked bispecific Fvs (sdFv), intrabodies, and anti-idiotypic (anti-Id) antibodies (including, e.g., anti-Id and anti-anti-Id antibodies to antibodies), and epitope-binding fragments of any of the above. In particular, antibodies include immunoglobulin molecules and immunologically active fragments of immunoglobulin molecules. Immunoglobulin molecules can be of any type (e.g., IgG, IgE, IgM, IgD, IgA and IgY), class (e.g., IgG1, IgG2, IgG3, IgG4, IgA1 and TgA2) or subclass.

As used herein, the terms "disease" and "disorder" are used interchangeably to refer to a condition, in particular, a pathological condition, and more particularly a disease affected by IL-15 signal transduction.

As used herein, the terms "immunospecifically binds," "immunospecifically recognizes," "specifically binds," "specifically recognizes" and analogous terms in the context of antibodies refer to molecules that specifically bind to an antigen (e.g., epitope or immune complex) and do not specifically bind to another molecule. A molecule that specifically binds to an antigen may bind to other peptides or polypeptides with lower affinity as determined by, e.g., immunoassays, BIAcore, or other assays known in the art. Preferably, molecules that specifically bind an antigen do not cross react with other proteins. Molecules that specifically bind an antigen can be identified, for example, by immunoassays, BIAcore, or other techniques known to those of skill in the art.

As used herein, the terms "specifically binds," "specifically recognizes" and analogous terms in the context of receptor (e.g., native IL-15Ra) and ligand (e.g., native IL-15) interaction refer to the specific binding or association between the ligand and receptor. Preferably, the ligand has higher affinity for the receptor than for other molecules. In a specific embodiment, the ligand is native IL-15 and the native receptor is IL-15Ra. In another specific embodiment, the ligand is the native IL-15/IL-15Ra complex and the native receptor is the βγ receptor complex. In a further embodiment, the IL-15/IL-15Ra complex binds to the βγ receptor complex and activates IL-15 mediated signal transduction. Ligands that specifically bind a receptor can be identified, for example, by immunoassays, BIAcore, or other techniques known to those of skill in the art.

As used herein, the terms "native IL-15" and "native interleukin-15" in the context of proteins or polypeptides refer to any naturally occurring mammalian interleukin-15 amino acid sequences, including immature or precursor and mature forms. Non-limiting examples of GeneBank Accession Nos. for the amino acid sequence of various species of native mammalian interleukin-15 include NP_000576 (human, immature form), CAA62616 (human, immature form), NP_001009207 (*Felis catus*, immature form), AAB94536 (*rattus*, immature form), AAB41697 (*rattus*, immature form), NP_032383 (*Mus musculus*, immature form), AAR19080 (canine), AAB60398 (*macaca mulatta*, immature form), AAI00964 (human, immature form), AAH23698 (*Mus musculus*, immature form), and AAH18149 (human). The amino acid sequence of the immature/precursor form of native human IL-15, which comprises the long signal peptide (underlined) and the mature human native IL-15 (italicized), is provided:
MRISKPHLRSISIQCYLCLLLNSHFLTEAGIHVFILGC FSAGLPKTEANWNVDLKKIE DLIQSMHIDATLFT-ESDVHPSCKVTAMKCFLLELQVISLESG- DASIHDTVENLIILANNSLSS NGNVTESGCKE-CEELEEKNIKEFLQSFVHIVQMFINTS (SEQ ID NO: 1). In some embodiments, native IL-15 is the immature or prescursor form of a naturally occurring mammalian IL-15. In other embodiments, native IL-15 is the mature form of a naturally occurring mammalian IL-15. In a specific embodiment, native IL-15 is the precursor form of naturally occurring human IL-15. In another embodiment, native IL-15 is the mature form of naturally occurring human IL-15. In one embodiment, the native IL-15 protein/polypeptide is isolated or purified.

As used herein, the terms "native IL-15" and "native "interleukin-15" in the context of nucleic acids refer to any naturally occurring nucleic acid sequences encoding mammalian interleukin-15, including the immature or precursor and mature forms. Non-limiting examples of GeneBank Accession Nos. for the nucleotide sequence of various species of native mammalian IL-15 include NM 000585

(human), NM_008357 (*Mus musculus*), and RNU69272 (*Rattus norvegicus*). The nucleotide sequence encoding the immature/precursor form of native human IL-15, which comprises the nucleotide sequence encoding the long signal peptide (underlined) and the nucleotide sequence encoding the mature human native IL-15 (italicized), is provided: atgagaatttcgaaacaacatttgagaagtatttccatccagtgctacttgtgtttact tctaaacagtcattttctaactgaagctggcattcatgtcttcattttgggcctgtttca *gtgcagggcttcctaaaacagaagccaact gggtgaatgt aataagtgat ttgaaaaaa ttgaagatct tattcaatct atgcatattg atgctactttatatacgaa aglgatgttc accccagttg caaagtaaca gcaatgaagt gctrtctott ggagt- tacaa gltatttcac ttgagtccgg agatgcaagt attcatgata caglagaaaa tctgatcatc ctagcaaaca acagtttgtc ttctaatggg aatgtaacag aatctg- gatg caaagaatgt gaggaactgg aggaaaaaaa tattaaagaa tttttgcaga gtttgtaca tattgtccaa atgttcatca acacttcttg a* (SEQ ID NO: 2). In a specific embodiment, the nucleic acid is an isolated or purified nucleic acid. In some embodiments, nucleic acids encode the immature or precursor form of a naturally occurring mammalian IL-15. In other embodiments, nucleic acids encode the mature form of a naturally occurring mammalian IL-15. In a specific embodiment, nucleic acids encoding native IL-15 encode the precursor form of naturally occurring human IL-15. In another embodiment, nucleic acids encoding native IL-15 encode the mature of naturally occurring human IL-15.

As used herein, the terms "IL-15 derivative" and "interleukin-15 derivative" in the context of proteins or polypeptides refer to: (a) a polypeptide that is at least 40%, 45%, 50%, 55%, 60%, 65%, 70%, 75%, 80%, 85%, 90%, 95%, 98% or 99% identical to a native mammalian IL-15 polypeptide; (b) a polypeptide encoded by a nucleic acid sequence that is at least 40%, 45%, 50%, 55%, 60%, 65%, 70%, 75%, 80%, 85%, 90%, 95%, 98% or 99% identical a nucleic acid sequence encoding a native mammalian IL-15 polypeptide; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to a native mammalian IL-15 polypeptide; (d) a polypeptide encoded by nucleic acids can hybridize under high, moderate or typical stringency hybridization conditions to nucleic acids encoding a native mammalian IL-15 polypeptide; (e) a polypeptide encoded by a nucleic acid sequence that can hybridize under high, moderate or typical stringency hybridization conditions to a nucleic acid sequence encoding a fragment of a native mammalian IL-15 polypeptide of at least 20 contiguous amino acids, at least 30 contiguous amino acids, at least 40 contiguous amino acids, at least 50 contiguous amino acids, at least 100 contiguous amino acids, or at least 150 contiguous amino acids; or (f) a fragment of a native mammalian IL-15 polypeptide. IL-15 derivatives also include a polypeptide that comprises the amino acid sequence of a naturally occurring mature form of a mammalian IL-15 polypeptide and a heterologous signal peptide amino acid sequence. In a specific embodiment, an IL-15 derivative is a derivative of a native human IL-15 polypeptide. In another embodiment, an IL-15 derivative is a derivative of an immature or precursor form of naturally occurring human IL-15 polypeptide. In another embodiment, an IL-15 derivative is a derivative of a mature form of naturally occurring human IL-15 polypeptide. In one embodiment, an IL-15 derivative is isolated or purified.

In a preferred embodiment, IL-15 derivatives retain at least 50%, 55%, 60%, 65%, 70%, 75%, 80%, 85%, 90%, 95%, 98% or 99% of the function of native mammalian IL-15 polypeptide to bind IL-15Ra polypeptide, as measured by assays well known in the art, e.g., ELISA, Biacore, co-immunoprecipitation. In another preferred embodiment, IL-15 derivatives retain at least 50%, 55%, 60%, 65%, 70%, 75%, 80%, 85%, 90%, 95%, 98% or 99% of the function of native mammalian IL-15 polypeptide to induce IL-15-mediated signal transduction, as measured by assays well-known in the art, e.g., electromobility shift assays, ELISAs and other immunoassays.

Percent identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wis.). Information regarding hybridization conditions (e.g., high, moderate, and typical stringency conditions) have been described, see, e.g., U.S. Patent Application Publication No. US 2005/0048549 (e.g., paragraphs 72-73).

As used herein, the terms "IL-15 derivative" and "interleukin-15 derivative" in the context of nucleic acids refer to: (a) a nucleic acid sequence that is at least 40%, 45%, 50%, 55%, 60%, 65%, 70%, 75%, 80%, 85%, 90%, 95%, 98% or 99% identical to the naturally occurring nucleic acid sequence encoding a mammalian IL-15 polypeptide; (b) a nucleic acid sequence encoding a polypeptide that is at least 40%, 45%, 50%, 55%, 60%, 65%, 70%, 75%, 80%, 85%, 90%, 95%, 98% or 99% identical the amino acid sequence of a native mammalian IL-15 polypeptide; (c) a nucleic acid sequence that contains 1, 2, 3, 4, 5, 6, 7, 8, 9, 10, 11, 12, 13, 14, 15, 16, 17, 18, 19, 20 or more nucleic acid base mutations (i.e., additions, deletions and/or substitutions) relative to the naturally occurring nucleic acid sequence encoding a mammalian IL-15 polypeptide; (d) a nucleic acid sequence that hybridizes under high, moderate or typical stringency hybridization conditions to a naturally occurring nucleic acid sequence encoding a mammalian IL-15 polypeptide; (e) a nucleic acid sequence that hybridizes under high, moderate or typical stringency hybridization conditions to a fragment of a naturally occurring nucleic acid sequence encoding a mammalian IL-15 polypeptide; and (f) a nucleic acid sequence encoding a fragment of a naturally occurring nucleic acid sequence encoding a mammalian IL-15 polypeptide. In a specific embodiment, an IL-15 derivative in the context of nucleic acids is a derivative of a naturally occurring nucleic acid sequence encoding a human IL-15 polypeptide. In another embodiment, an IL-15 derivative in the context of nucleic acids is a derivative of a naturally occurring nucleic acid sequence encoding an immature or precursor form of a human IL-15 polypeptide. In another embodiment, an IL-15 derivative in the context of nucleic acids is a derivative of a naturally occurring nucleic acid sequence encoding a mature form of a human IL-15 polypeptide.

IL-15 derivative nucleic acid sequences include codon-optimized nucleic acid sequences that encode native mammalian IL-15 polypeptide, including mature and immature forms of IL-15 polypeptide. In other embodiments, IL-15 derivative nucleic acids include nucleic acids that encode mammalian IL-15 RNA transcripts containing mutations that eliminate potential splice sites and instability elements (e.g., A/T or A/U rich elements) without affecting the amino acid sequence to increase the stability of the mammalian IL-15 RNA transcripts.

In a preferred embodiment, IL-15 derivative nucleic acid sequences encode proteins or polypeptides that retain at least 50%, 55%, 60%, 65%, 70%, 75%, 80%, 85%, 90%, 95%, 98% or 99% of the function of a native mammalian IL-15 polypeptide to bind IL-15Ra polypeptide as measured by assays well known in the art, e.g., ELISA, Biacore, co-immunoprecipitation. In another preferred embodiment, IL-15 derivative nucleic acid sequences encode proteins or polypeptides that retain at least 50%, 55%, 60%, 65%, 70%, 75%, 80%, 85%, 90%, 95%, 98% or 99% of the function of a native mammalian IL-15 polypeptide to induce IL-15-mediated signal transduction, as measured by assays well-known in the art, e.g., electromobility shift assays, ELISAs and other immunoassays.

As used herein, the terms "IL-15" and "interleukin-15" refer to a native IL-15, an IL-15 derivative, or a native IL-15 and an IL-15 derivative.

As used herein, the terms "native IL-15Ra" and "native interleukin-15 receptor alpha" in the context of proteins or polypeptides refer to any naturally occurring mammalian interleukin-15 receptor alpha ("IL-15Ra") amino acid sequence, including immature or precursor and mature forms and naturally occurring isoforms. Non-limiting examples of GeneBank Accession Nos. for the amino acid sequence of various native mammalian IL-15Ra include NP_002180 (human), ABK41438 (*Macaea mulatta*), NP_032384 (*Mus musculus*), Q60819 (*Mus musculus*), CAI41082 (human). The amino acid sequence of the immature form of the native full length human IL-15Ra, which comprises the signal peptide (underlined) and the mature human native IL-15Ra (italicized), is provided: MAPRRARGCRTLGLPALLLLLLLRPPATRG ITCPPPMSVE HADIWVKSYS LYSRERYICN SGFKRK- AGTS SLTECVLNKA TNVAHIWITPS LKCIRDPALV HQRPAPPSTV TTAGVTPQPE SLSPSGKEPA ASSPSSNNTA ATTAAIVPGS QLMPSKSPST GTTEIS- SHES SHGTPSQTTA KNWELTASAS HQPPGVYPQG HSDTTVAIST STVLLCGLSA VSLLACYLKS RQTP- PLASVE MEAMEALPVT WGTSRDEDL ENCSHHL (SEQ ID NO: 3). The amino acid sequence of the immature form of the native soluble human IL-15Ra, which comprises the signal peptide (underlined) and the mature human native IL-15Ra (italicized), is provided: MAPRRARGCRTLGLPALLLLLLLRPPATRG ITCPPPMSVE HADIWVKSYS LYSRERYICN SGFKRK- AGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEIS- SHES SHGTPSQTTA KNWELTASAS HQPPGVYPQG HSDTT (SEQ ID NO: 4). In some embodiments, native IL-15Ra is the immature form of a naturally occurring mammalian IL-15Ra polypeptide. In other embodiments, native IL-15Ra is the mature form of a naturally occurring mammalian IL-15Ra polypeptide. In certain embodiments, native IL-15Ra is a soluble form of a naturally occurring mammalian IL-15Ra polypeptide. In other embodiments, native IL-15Ra is the full-length form of a naturally occurring mammalian IL-15Ra polypeptide. In a specific embodiment, native IL-15Ra is the immature form of a naturally occurring human IL-15Ra polypeptide. In another embodiment, native IL-15Ra is the mature form of a naturally occurring human IL-15Ra polypeptide. In certain embodiments, native IL-15Ra is the soluble form of a naturally occurring human IL-15Ra polypeptide. In other embodiments, native IL-15Ra is the full-length form of a naturally occurring human IL-15Ra polypeptide. In one embodiment, a native IL-15Ra protein or polypeptide is isolated or purified.

As used herein, the terms "native IL-15Ra" and "native interleukin-15 receptor alpha" in the context of nucleic acids refer to any naturally occurring nucleic acid sequences encoding mammalian interleukin-15 receptor alpha, including the immature or precursor and mature forms. Non-limiting examples of GeneBank Accession Nos. for the nucleotide sequence of various species of native mammalian IL-15Ra include NM_002189 (human), EF033114 (*Macaca mulatta*), and NM_008358 (*Mus musculus*). The nucleotide sequence encoding the immature form of native human IL-15Ra, which comprises the nucleotide sequence encoding the signal peptide (underlined) and the nucleotide sequence encoding the mature human native IL-15Ra (italicized), is provided: atggccccgcggcngcgcgcggctgccggaccctctctcccggcgctctactct gctgctgctccgccgccggcgacgcggggcatcacgtg ccctcccccc atgtccgtgg aacacgcaga catctgggtc aagagctaca gctgtactc cagggagcgg tacatttgla actctagtt caagcgtaaa gccggcacgt ccagcctgac ggagtgcgtg ttgaacaagg ccacgaatgt cgcccactgg acaacccca gtctcaaatg cattagagac cctgccctgg ttcac- caaaggccagcgcca ccctccacag taacgacggc aggggtgacc ccacagccag agagcctctc cccttctgga aaagagcccg cagcttcatc tcccagctca aacaacacag cggccacaac agcagctatt gtcccgggct cccagctgat gccttcaaaa tcaccttcca caggaaccac agagataagc agt- catgagt cctcccacgg cacccctct cagacaacag ccaagaactg ggaactcaca gcatccgcct cccaccagcc gccaggtgtg tatccacagg gccacagcga caccactgtg gctatctcca cgtccactgt cctgctgtgt gggctgagcg ctgtglctct cctggcatgc tacctcaagt caaggcaaac tccccgctg gccagcgttg aaatggaagc catggaggct ctgccggtga cttgggggac cagcagcaga gatgaagact tggaaaactg ctctcaccac ctatga (SEQ ID NO: 5). The nucleotide sequence encoding the immature form of native soluble human IL-15Ra protein or polypeptide, which comprises the nucleotide sequence encoding the signal peptide (underlined) and the nucleotide sequence encoding the mature human soluble native IL-15Ra (italicized), is provided: atggccccgcggcgggcgcgcgctgccggaccctcggtctcccggcgctgcta ctgctgctgcttccggccccggcgacgcggggcatcacgtg ccctcccccc atgtccgtgg aacacgcaga catctgggtc aagagctaca gcttgtactc cagggagcgg tacatttgta actctggttt caagcgtaaa gccggcacgt ccagcctgac ggagtgcgtg ttgaacaagg ccacgaatgt cgcccactgg acaacccca gtctcaaatg cattagagac cctgccctgg ttcaccaaag gccagcgcca ccctccacag taacgacggc aggggtgacc ccacagccag agagcctctc cccttctgga aaagagcccg cagcttcatc tcccagctca aacaacacag cggccacaac agcagctatt gtcccgggct cccagctgat gccttcaaaa tcaccttcca caggaaccac agagataagc agtcatgagt cctcccacgg cacccctct cagacaacag ccaagaactg ggaactcaca gcatccgcct cccaccagcc gccaggtgtg tatccacagg gccacagcga caccact (SEQ ID NO: 6). In a specific embodiment, the nucleic acid is an isolated or purified nucleic acid. In some embodiments, naturally occurring nucleic acids encode the immature form of a naturally occurring mammalian IL-15Ra polypeptide. In other embodiments, naturally occurring nucleic acids encode the mature form of a naturally occurring mammalian IL-15Ra polypeptide. In certain embodiments, naturally occurring nucleic acids encode the soluble form of a naturally occurring mammalian IL-15Ra polypeptide. In other embodiments, naturally occurring nucleic acids encode the full-length form of a naturally occurring mammalian IL-15Ra polypeptide. In a specific embodiment, naturally occurring nucleic acids encode the precursor form of naturally occurring human IL-15 polypeptide. In another embodiment, naturally occurring nucleic acids encode the mature of naturally occurring human IL-15 polypeptide. In certain embodiments, naturally occurring nucleic acids encode the soluble form of a naturally occurring human IL-15Ra polypeptide. In other embodiments, naturally occurring nucleic acids encode the full-length form of a naturally occurring human IL-15Ra polypeptide.

As used herein, the terms "IL-15Ra derivative" and "interleukin-15 receptor alpha derivative" in the context of a protein or polypeptide refer to: (a) a polypeptide that is at least 40%, 45%, 50%, 55%, 60%, 65%, 70%, 75%, 80%, 85%, 90%, 95%, 98% or 99% identical to a native mammalian IL-15 polypeptide; (b) a polypeptide encoded by a nucleic acid sequence that is at least 40%, 45%, 50%, 55%, 60%, 65%, 70%, 75%, 80%, 85%, 90%, 95%, 98% or 99% identical a nucleic acid sequence encoding a native mammalian IL-15Ra polypeptide; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to a native mammalian IL-15Ra polypeptide; (d) a polypeptide encoded by a nucleic acid sequence that can hybridize under high, moderate or typical stringency hybridization conditions to a nucleic acid sequence encoding a native mammalian IL-15Ra polypeptide; (e) a polypeptide encoded by a nucleic acid sequence that can hybridize under high, moderate or typical stringency hybridization conditions to nucleic acid sequences encoding a fragment of a native mammalian IL-15 polypeptide of at least 20 contiguous amino acids, at least 30 contiguous amino acids, at least 40 contiguous amino acids, at least 50 contiguous amino acids, at least 100 contiguous amino acids, or at least 150 contiguous amino acids; or (f) a fragment of a native mammalian IL-15Ra polypeptide. IL-15Ra derivatives also include a polypeptide that comprises the amino acid sequence of a naturally occurring mature form of mammalian IL-15Ra polypeptide and a heterologous signal peptide amino acid sequence. In a specific embodiment, an IL-15Ra derivative is a derivative of a native human IL-15Ra polypeptide. In another embodiment, an IL-15Ra derivative is a derivative of an immature form of naturally occurring human IL-15 polypeptide. In another embodiment, an IL-15Ra derivative is a derivative of a mature form of naturally occurring human IL-15 polypeptide. In one embodiment, an IL-15Ra derivative is the soluble form of a native mammalian IL-15Ra polypeptide. In a specific embodiment, an IL-15Ra derivative is purified or isolated.

In a preferred embodiment, IL-15Ra derivatives retain at least 50%, 55%, 60%, 65%, 70%, 75%, 80%, 85%, 90%, 95%, 98% or 99% of the function of a native mammalian IL-15Ra polypeptide to bind an IL-15 polypeptide, as measured by assays well known in the art, e.g., ELISA, Biacore, co-immunoprecipitation. In another preferred embodiment, IL-15Ra derivatives retain at least 50%, 55%, 60%, 65%, 70%, 75%, 80%, 85%, 90%, 95%, 98% or 99% of the function of a native mammalian IL-15Ra polypeptide to induce IL-15-mediated signal transduction, as measured by assays well-known in the art, e.g., electromobility shift assays, ELISAs and other immunoassays.

As used herein, the terms "IL-15Ra derivative" and "interleukin-15 receptor alpha derivative" in the context of nucleic acids refer to: (a) a nucleic acid sequence that is at least 40%, 45%, 50%, 55%, 60%, 65%, 70%, 75%, 80%, 85%, 90%, 95%, 98% or 99% identical to the naturally occurring nucleic acid sequence encoding a mammalian IL-15Ra polypeptide; (b) a nucleic acid sequence encoding a polypeptide that is at least 40%, 45%, 50%, 55%, 60%, 65%, 70%, 75%, 80%, 85%, 90%, 95%, 98% or 99% identical the amino acid sequence of a native mammalian IL-15Ra polypeptide; (c) a nucleic acid sequence that contains 1, 2, 3, 4, 5, 6, 7, 8, 9, 10, 11, 12, 13, 14, 15, 16, 17, 18, 19, 20 or more nucleic acid mutations (i.e., additions, deletions and/or substitutions) relative to the naturally occurring nucleic acid sequence encoding a mammalian IL-15Ra polypeptide; (d) a nucleic acid sequence that hybridizes under high, moderate or typical stringency hybridization conditions to a naturally occurring nucleic acid sequence encoding a mammalian IL-15Ra polypeptide; (e) a nucleic acid sequence that hybridizes under high, moderate or typical stringency hybridization conditions to a fragment of a naturally occurring nucleic acid sequence encoding a mammalian IL-15Ra polypeptide; and (f) a nucleic acid sequence encoding a fragment of a naturally occurring nucleic acid sequence encoding a mammalian IL-15Ra polypeptide. In a specific embodiment, an IL-15Ra derivative in the context of nucleic acids is a derivative of a naturally occurring nucleic acid sequence encoding a human IL-15Ra polypeptide. In another embodiment, an IL-15Ra derivative in the context of nucleic acids is a derivative of a naturally occurring nucleic acid sequence encoding an immature form of a human IL-15Ra polypeptide. In another embodiment, an IL-15Ra derivative in the context of nucleic acids is a derivative of a naturally occurring nucleic acid sequence encoding a mature form of a human IL-15Ra polypeptide. In one embodiment, an IL-15Ra derivative refers to a nucleic acid sequence encoding a mammalian IL-15Ra polypeptide that is soluble.

IL-15Ra derivative nucleic acid sequences include codon-optimized nucleic acid sequences that encode native IL-15Ra polypeptide, including mature and immature forms of IL-15Ra polypeptide. In other embodiments, IL-15Ra derivative nucleic acids include nucleic acids that encode IL-15Ra RNA transcripts containing mutations that eliminate potential splice sites and instability elements (e.g., A/T or A/U rich elements) without affecting the amino acid sequence to increase the stability of the IL-15Ra RNA transcripts.

In a preferred embodiment, IL-15Ra derivative nucleic acid sequences encode proteins or polypeptides that retain at least 50%, 55%, 60%, 65%, 70%, 75%, 80%, 85%, 90%, 95%, 98% or 99% of the function of a native mammalian IL-15Ra polypeptide to bind IL-15, as measured by assays well known in the art, e.g., ELISA, Biacore, co-immunoprecipitation. In another preferred embodiment, IL-15Ra derivative nucleic acid sequences encode proteins or polypeptides that retain at least 50%, 55%, 60%, 65%, 70%, 75%, 80%, 85%, 90%, 95%, 98% or 99% of the function of a native mammalian IL-15Ra to induce IL-15-mediated signal transduction, as measured by assays well-known in the art, e.g., electromobility shift assays, ELISAs and other immunoassays.

As used herein, the terms "IL-15Ra" and "interleukin-15 receptor alpha" refer to a native IL-15Ra, an IL-15Ra derivative, or a native IL-15Ra and an IL-15Ra derivative.

As used herein, the term "IL-15/IL-15Ra complex" refers to a complex comprising IL-15 and IL-15Ra covalently or noncovalently bound to each other. In a preferred embodiment, the IL-15Ra has a relatively high affinity for IL-15, e.g., $K_d$ of 10 to 50 pM as measured by a technique known in the art, e.g., KinEx A assay, plasma surface resonance (e.g., BIAcore assay). In another preferred embodiment, the IL-15/IL-15Ra complex induces IL-15-mediated signal transduction, as measured by assays well-known in the art, e.g., electromobility shift assays, ELISAs and other immunoassays. In some embodiments, the IL-15/IL-15Ra complex retains the ability to specifically bind to the 07 chain.

As used herein, the terms "subject" and "patient" are used interchangeably and refer to a mammal such as a non-primate (e.g., cows, pigs, horses, cats, dogs, rats etc.) and a primate (e.g., monkey and human), most preferably a human.

As used herein, the terms "purified" and "isolated" in the context of a compound or agent (including, e.g., proteinaceous agents such as antibodies) that is chemically synthesized refers to a compound or agent that is substantially free of chemical precursors or other chemicals when chemically synthesized. In a specific embodiment, the compound or agent is 60%, 65%, 75%, 80%, 85%, 90%, 95%, or 99% free (by dry weight) of other, different compounds or agents.

As used herein, the terms "purified" and "isolated" when used in the context of a compound or agent (including proteinaceous agents such as antibodies and polypeptides) that can be obtained from a natural source, e.g., cells, refers to a compound or agent which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. The phrase "substantially free of natural source materials" refers to preparations of a compound or agent that has been separated from the material (e.g., cellular components of the cells) from which it is isolated. Thus, a compound or agent that is isolated includes preparations of a compound or agent having less than about 30%, 20%, 10%, 5%, 2%, or 1% (by dry weight) of cellular materials and/or contaminating materials.

An "isolated" nucleic acid sequence or nucleotide sequence is one which is separated from other nucleic acid molecules which are present in a natural source of the nucleic acid sequence or nucleotide sequence. Moreover, an "isolated", nucleic acid sequence or nucleotide sequence, such as a cDNA molecule, can be substantially free of other cellular material or culture medium when produced by recombinant techniques, or substantially free of chemical precursors when chemically synthesized. In certain embodiments, an "isolated" nucleic acid sequence or nucleotide sequence is a nucleic acid sequence or nucleotide sequence that is recombinantly expressed in a heterologous cell.

In some embodiments, the terms "nucleic acid", "nucleotide" and "polynucleotide" refer to deoxyribonucleotides, deoxyribonucleic acids, ribonucleotides, and ribonucleic acids, and polymeric forms thereof, and include either single- or double-stranded forms. In certain embodiments, such terms include known analogues of natural nucleotides, for example, peptide nucleic acids ("PNA"s), that have similar binding properties as the reference nucleic acid. In some embodiments, such terms refer to deoxyribonucleic acids (e.g., cDNA or DNA). In other embodiments, such terms refer to ribonucleic acid (e.g., mRNA or RNA).

As used herein, the terms "therapies" and "therapy" can refer to any protocol(s), method(s), compositions, formulations, and/or agent(s) that can be used in the prevention, treatment, management, or amelioration of a disease, e.g., cancer, infectious disease, autoimmune disease, graft versus host disease, and transplantation rejection, or a symptom associated therewith. In certain embodiments, the terms "therapies" and "therapy" refer to biological therapy, supportive therapy, and/or other therapies useful in treatment, management, prevention, or amelioration of a disease or a symptom associated therewith known to one of skill in the art. In one embodiment, a therapy includes an Agonistic Therapeutic Agent. In one embodiment, a therapy includes an Antagonistic Therapeutic Agent. In one embodiment, a therapy is not an Agonistic Therapeutic Agent. In one embodiment, a therapy is not an Antagonistic Therapeutic Agent.

As used herein, the terms "protein(s)" and "polypeptide(s)" interchangeably to refer to a chain of amino acids linked together by peptide bonds. In some embodiments, the terms "protein(s)" and "polypeptide(s)" refer to a macromolecule which comprises amino acids that are linked together by peptide bonds.

As used herein, the term "fragment" in the context of a nucleotide sequence refers to a nucleotide sequence comprising an nucleic acid sequence of at least 5 contiguous nucleic acid bases, at least 10 contiguous nucleic acid bases, at least 15 contiguous nucleic acid bases, at least 20 contiguous nucleic acid bases, at least 25 contiguous nucleic acid bases, at least 40 contiguous nucleic acid bases, at least 50 contiguous nucleic acid bases, at least 60 contiguous nucleic acid bases, at least 70 contiguous nucleic acid bases, at least 80 contiguous nucleic acid bases, at least 90 contiguous nucleic acid bases, at least 100 contiguous nucleic acid bases, at least 125 contiguous nucleic acid bases, at least 150 contiguous nucleic acid bases, at least 175 contiguous nucleic acid bases, at least 200 contiguous nucleic acid bases, or at least 250 contiguous nucleic acid bases of the nucleotide sequence of the gene of interest, e.g., IL-15, IL-15Ra. The nucleic acid may be RNA, DNA, or a chemically modified variant thereof. In a specific embodiment, the fragment is a fragment of IL-15 or IL-15Ra.

As used herein, the term "fragment" is the context of a fragment of a proteinaceous agent (e.g., a protein or polypeptide) refers to a fragment that is composed of 8 or more contiguous amino acids, 10 or more contiguous amino acids, 15 or more contiguous amino acids, 20 or more contiguous amino acids, 25 or more contiguous amino acids, 50 or more contiguous amino acids, 75 or more contiguous amino acids, 100 or more contiguous amino acids, 150 or more contiguous amino acids, 200 or more contiguous amino acids, 10 to 150 contiguous amino acids, 10 to 200 contiguous amino acids, 10 to 250 contiguous amino acids, 10 to 300 contiguous amino acids, 50 to 100 contiguous amino acids, 50 to 150 contiguous amino acids, 50 to 200 contiguous amino acids, 50 to 250 contiguous amino acids or 50 to 300 contiguous amino acids of a proteinaceous agent, e.g., IL-15 and IL-15Ra polypeptides.

As used herein, the term "in combination" refers to the use of more than one therapies (e.g., one or more prophylactic and/or therapeutic agents). The use of the term "in combination" does not restrict the order in which therapies are administered to a subject with a disease or disorder. A first therapy (e.g., a prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disease or disorder or a symptom thereof.

As used herein, the term "premature human infant" refers to a human infant born at less than 37 weeks of gestational age.

As used herein, the term "human infant" refers to a newborn to 1 year old year human.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the terms "treat", "treating" and "treatment" in the context of the administration of a therapy to a subject refer to the beneficial effects that a subject derives from a therapy, such as, but not limited to, the reduction or inhibition of the progression, spread and/or duration of a disease or disorder, the reduction or amelioration of the severity of a disease or disorder, amelioration of one or more symptoms of a disease or disorder, and/or the reduction in the duration of one or more symptom of a disease or disorder resulting from the administration of one or more therapies. In specific embodiments, such terms in the context of cancer include, but are not limited to, one, two, or three or more results following the administration of a therapy to a subject: (1) a reduction in the growth of a tumor or neoplasm; (2) a reduction in the formation of a tumor; (3) an eradication, removal, or control of primary, regional and/or metastatic cancer; (4) a reduction in metastatic spread; (5) a reduction in mortality; (6) an increase in survival rate; (7) an increase in length of survival; (8) an increase in the number of patients in remission; (9) a decrease in hospitalization rate; (10) a decrease in hospitalization lengths; and (11) the maintenance in the size of the tumor so that it does not increase by more than 10%, or by more than 8%, or by more than 6%, or by more than 4%; preferably the size of the tumor does not increase by more than 2%.

As used herein, the terms "prevent," "preventing" and "prevention" in the context of the administration of a therapy to a subject refer to the inhibition of the onset or recurrence of a disease or disorder in a subject.

As used herein, the terms "manage," "managing," and "management," in the context of the administration of a therapy to a subject, refer to the beneficial effects that a subject derives from a therapy, which does not result in a cure of a disease or disorder. In certain embodiments, a subject is administered one or more therapies to "manage" a disease or disorder so as to prevent the progression or worsening of symptoms associated with a disease or disorder.

4. BRIEF DESCRIPTION OF THE DRAWINGS

FIGS. 1A-B: Nucleic acid and amino acid sequences of native human IL-15. The nucleic acid sequence (FIG. 1A) (SEQ ID NO: 2) and amino acid sequence (FIG. 1B) (SEQ ID NO: 1) are shown. The amino acid sequence and nucleic acid sequence of the long signal peptide (underlined) and mature form (italicized) are indicated.

FIGS. 2A-B: Nucleic acid and amino acid sequences of full length native human IL-15Ra. The nucleic acid sequence (FIG. 2A) (SEQ ID NO: 5) and amino acid sequence (FIG. 2B) (SEQ ID NO: 3) are shown. The amino acid sequence and nucleic acid sequence of the signal peptide (underlined) and mature form (italicized) are indicated.

FIGS. 3A-B: Nucleic acid and amino acid sequences of soluble native human IL-15. The nucleic acid sequence (FIG. 3A) (SEQ ID NO: 6) and amino acid sequence (FIG. 3B) (SEQ ID NO: 4) are shown. The amino acid sequence and nucleic acid sequence of the signal peptide (underlined) and mature form (italicized) are indicated.

FIGS. 4A-D: AG32 nucleic acid construct encoding optimized human IL-15. The nucleic acid sequence (FIG. 4A) (SEQ ID NO: 9) and the amino acid sequence (FIG. 4B) (SEQ ID NO: 10) are shown. FIG. 4C shows a schematic of the nucleic acid construct comprising the CMV promoter. FIG. 4D shows an alignment of the amino acid sequence translated from the open reading frame of the nucleic acid sequence encoding optimized human IL-15 (AG32 huIL15opt).

FIGS. 5A-D: AG59 nucleic acid construct encoding optimized human IL-15 with a signal peptide and pro-peptide of tPA. The nucleic acid sequence (FIG. 5A) (SEQ ID NO: 11) and the amino acid sequence (FIG. 5B) (SEQ ID NO: 12) are shown. FIG. 5C shows a schematic of the nucleic acid expression construct comprising the CMV promoter. FIG. 5D shows an alignment of the amino acid sequence translated from the open reading frame of the nucleic acid sequence encoding optimized human IL-15 (AG59 CMV huIL15tPA6).

Figure 6C:
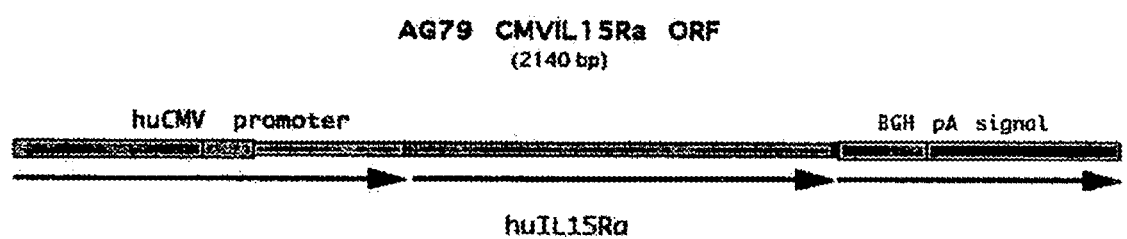

FIGS. 6A-D: AG79 nucleic acid construct encoding optimized human IL-15Ra. The nucleic acid sequence (FIG. 6A) (SEQ ID NO: 13) and the amino acid sequence (FIG. 6B) (SEQ ID NO: 14) are shown. FIG. 6C shows a schematic of the nucleic acid expression construct comprising the CMV promoter. FIG. 6D shows an alignment of the amino acid sequence translated from the open reading frame of the nucleic acid sequence encoding human IL-15Ra (AG79 huIL15Ra).

FIGS. 7A-D: AG98 nucleic acid construct encoding optimized soluble human IL-15Ra. The nucleic acid sequence (FIG. 7A) (SEQ ID NO: 15) and the amino acid sequence (FIG. 7B) (SEQ ID NO: 16) are shown. FIG. 7C shows a schematic of the nucleic acid expression construct comprising the CMV promoter. FIG. 7D shows an alignment of the amino acid sequence translated from the open reading frame of the nucleic acid sequence encoding soluble human IL-15Ra (AG98 CMV hu sIL15Ra).

FIGS. 8A-D: AG151 nucleic acid construct encoding optimized human IL-15 with a signal peptide of human GM-CSF. The nucleic acid sequence (FIG. 8A) (SEQ ID NO: 17) and the amino acid sequence (FIG. 8B) (SEQ ID NO: 18) are shown. FIG. 8C shows a schematic of the nucleic acid expression construct comprising the CMV promoter. FIG. 8D shows an alignment of the amino acid sequence translated from the open reading frame of the nucleic acid sequence encoding human IL-5 with a signal peptide of human GM-CSF (AG151 CMVhuIL15huGMCSF).

5. DETAILED DESCRIPTION OF THE INVENTION

The present invention relates to agents that modulate IL-15 signal transduction or function ("Therapeutic Agents") and the use of those agents to modulate immune function. The Therapeutic Agents target the interaction between IL-15 and its receptor and modulate IL-15-induced signal transduction. In a specific embodiment, the Therapeutic Agents modulate the interaction between the IL-15 receptor beta and gamma complex and complexes composed of IL-15 and IL-15Ra.

The present invention provides Therapeutic Agents that induce IL-15 signal transduction and enhance the immune function (i.e., Agonistic Therapeutic Agents). Such Agonistic Therapeutic Agents include (i) IL-15/IL-15Ra complexes that bind to the beta/gamma receptor complex and induce IL-15-mediated signal transduction, (ii) nucleic acid sequences encoding IL-15 and IL-15Ra to form such complexes, and (iii) cells expressing such complexes in high amounts. In one embodiment, high amounts of IL-15/IL-15Ra complexes refer to amounts of IL-15/IL-15Ra complexes expressed by cells that are at least 1 fold, 2 fold, 3 fold, 4 fold, 5 fold, 6 fold, 7 fold, 8 fold, 9 fold, 10 fold, 20 fold, or more than 20 fold higher than amounts of IL-15/IL-15Ra complexes expressed endogenously by control cells (e.g., cells that have not been genetically engineered to recombinantly express IL-15, IL-15Ra, or both IL-15 and IL-15Ra, or cells comprising an empty vector). The Agonistic Therapeutic Agents are useful for the prevention, treatment and/or management of disorders in which it is beneficial to enhance certain aspects of the immune system function, in particular, immune system functions that are mediated by IL-15 signaling. Non-limiting examples of such disorders include cancer and infectious diseases.

The present invention also provides Therapeutic Agents that reduce or inhibit IL-15 signal transduction and suppress the immune system function (i.e., Antagonistic Therapeutic Agents"). Such Antagonistic Therapeutic Agents include antibodies that immunospecifically bind to an IL-15/IL-15Ra complex and prevent endogenous IL-15/IL-15Ra from binding to the beta/gamma receptor complex and from inducing IL-15-mediated signal transduction. The Antagonistic Therapeutic Agents are useful for the prevention, treatment and/or management of disorders in which it is beneficial to suppress certain aspects of the immune function, in particular, immune system functions that are mediated by IL-15 signaling. Non-limiting examples of such disorders include autoimmune diseases, inflammatory conditions, graft versus host disease, and transplant rejection.

In other aspects, the invention provides an Agonistic Therapeutic Agent or an Antagonistic Therapeutic Agent formulated with any natural polymer fiber suitable for biomedical use, including, but not limited to, chitin and chitosan, derived from shellfish, fungal, or microalgal sources. In a preferred embodiment, the polymer fiber is poly-$\beta$-1→4-N-acetylglucosamine (p-GlcNAc), including deacetylated forms of pGlcNAc. In a specific embodiment, the Agonistic Therapeutic Agent or Antagonistic Therapeutic Agent formulated with a natural polymer is administered to a subject. In one embodiment, the Agonistic Therapeutic Agent or Antagonistic Therapeutic Agent is purified.

The Therapeutic Agents may be advantageously used in combination therapy. Combination therapy includes concurrent and successive administration of a Therapeutic Agent and another therapy. As used herein, the Therapeutic Agent and another therapy are said to be administered concurrently if they are administered to the patient on the same day, for example, simultaneously, or 1, 2, 3, 4, 5, 6, 7 or 8 hours apart. In contrast, the Therapeutic Agent and the therapy are said to be administered successively if they are administered to the patient on the different days, for example, the Therapeutic Agent and the therapy can be administered at a 1-day, 2-day or 3-day intervals. In the methods of the present invention, administration of the Therapeutic Agent can precede or follow administration of the second therapy.

As a non-limiting example, the Therapeutic Agent and another therapy can be administered concurrently for a first period of time, followed by a second period of time in which the administration of the Therapeutic Agent and the other therapy is alternated.

When administered simultaneously, the Therapeutic Agent and the other therapy can be in the same pharmaceutical composition or in different pharmaceutical compositions.

The subsections below describe in more detail Therapeutic Agents, screening assays for identifying or validating Therapeutic Agents, methods for characterizing Therapeutic Agents, formulations comprising the Therapeutic Agents, and methods of using the Therapeutic Agents to modulate immune system function.

5.1. Therapeutic Agents

The invention provides for Therapeutic Agents that modulate IL-15-mediated function or signaling. In particular, the present invention provides Therapeutic Agents that enhance IL-15-mediated function or signaling (i.e., Agonistic Therapeutic Agents). The administration of an Agonistic Therapeutic Agent to a subject in need thereof enhances IL-15-mediated function or signaling, which in turn results in the enhancement of certain aspects of the immune function in the subject. The enhancement of the immune function can be in the form of, e.g., an antibody response (humoral response) or a cellular immune response, e.g., cytokine secretion (e.g., interferon-gamma), helper activity or cellular cytotoxicity. In one embodiment, the enhancement of the immune function is increased cytokine secretion, antibody production, effector function, T cell proliferation, and/or NK cell proliferation.

The present invention also provides Therapeutic Agents that suppress or reduce IL-15-mediated function or signaling (i.e., Antagonistic Therapeutic Agents). The administration of an Antagonistic Therapeutic Agent to a subject in need thereof suppresses or decreases IL-15-mediated function or signaling, which in turn results in the suppression of certain aspects of the immune function in the subject. The suppression of the immune function can be in the form of, e.g., a lower antibody response (humoral response) or a lower cellular immune response, e.g., cytokine secretion (e.g., interferon-gamma), helper activity or cellular cytotoxicity. In one embodiment, the suppression of the immune function is decreased cytokine secretion, antibody production, effector function, T cell proliferation, and/or NK cell proliferation.

5.1.1. Protein Complexes

The present invention provides Therapeutic Agents that are complexes comprising IL-15 covalently or noncovalently bound to IL-15Ra ("IL-15/IL-15Ra complexes"). The IL-15/IL-15Ra complex is able to bind to the $\beta\gamma$ receptor complex. In a specific embodiment, the Agonistic Therapeutic Agents are IL-15/IL-15Ra complexes that can induce IL-15-mediated signal transduction, e.g., IL-15-mediated Jak/Stat pathway signal transduction. Such induction in IL-15-mediated signaling results in enhancement of an immune function in a subject.

The IL-15/IL-15Ra complexes may be composed of native IL-15 or an IL-15 derivative and native IL-15Ra or an IL-15Ra derivative. In a specific embodiment, the IL-15/IL-15Ra complex is composed of an IL-15 derivative and an IL-15Ra derivative. In one embodiment, the IL-15Ra derivative is a soluble form of IL-15Ra. In a specific embodiment, the soluble form of IL-15Ra lacks the transmembrane domain of native IL-15Ra, and optionally, the intracellular domain of native IL-15Ra. In another embodiment, the IL-15Ra derivative is the extracellular domain of native IL-15Ra or a fragment thereof. In certain embodiments, the IL-15Ra derivative is a fragment of the extracellular domain comprising the sushi domain or exon 2 of native IL-15Ra. In some embodiments, the IL-15Ra derivative comprises a fragment of the extracellular domain comprising the sushi domain or exon 2 of native IL-15Ra and at least one amino acid that is encoded by exon 3. In certain embodiments, the IL-15Ra derivative comprises a fragment of the extracellular domain comprising the sushi domain or exon 2 of native IL-15Ra and an IL-15Ra hinge region or a fragment thereof. In a specific embodiment, the IL-15Ra derivative is encoded by a nucleic acid sequence optimized to enhance expression of IL-15Ra, e.g., using methods as described in U.S. Provisional Application No. 60/812,566, filed on Jun. 9, 2006; and U.S. Pat. Nos. 5,965,726; 6,174,666; 6,291,664; 6,414,132; and 6,794,498, which are incorporated by reference herein in their entireties. In another embodiment, the IL-15 derivative is encoded by a nucleic acid sequence optimized to enhance expression of IL-15, e.g., using methods as described in U.S. Provisional Application Nos. 60/812,566, filed on Jun. 9, 2006 and 60/758,819, filed on Jan. 13, 2006, and International Patent Application Publication No. WO 2007/084342; and U.S. Pat. Nos. 5,965,726; 6,174,666; 6,291,664; 6,414,132; and 6,794,498, which are incorporated by reference herein in their entireties.

In another embodiment, the IL-15Ra derivative comprises a mutation in the extracellular domain cleavage site that inhibits cleavage by an endogenous protease that cleaves native IL-15Ra. In a specific embodiment, the extracellular domain cleavage site of IL-15Ra is replaced with a cleavage site that is recognized and cleaved by a heterologous known protease. Non-limiting examples of such heterologous protease cleavage sites include Arg-X-X-Arg (SEQ ID NO: 7), which is recognized and cleaved by furin protease; and A-B-Pro-Arg-X-Y (SEQ ID NO: 8) (A and B are hydrophobic amino acids and X and Y are nonacidic amino acids) and Gly-Arg-Gly, which are recognized and cleaved by thrombin protease.

In addition to IL-15 and IL-15Ra, the IL-15/IL-15Ra complexes may comprise a heterologous molecule. In some embodiments, the heterologous molecule is an antigen associated with a disease that one intends to prevent, treat and/or manage (e.g., a viral antigen, bacterial antigen, parasitic antigen, or cancer antigen). Non-limiting examples of such antigens include antigens of the flavivirus, West Nile Virus (WNV) including structural proteins, e.g., C, M, and E, and non-structural proteins, e.g., NS1, NS2A, NS2B, NS3, NS4A, NS4B and NS5; human immunodeficiency virus (HIV) antigens gp41, gp120, gp160, Nef, Gag, and Rev, Tat, Vif, Vpu, Vpr, or vpx; influenza virus hemagglutinin; human respiratory syncytial virus G glycoprotein; core protein, matrix protein or other protein of Dengue virus; measles virus hemagglutinin; herpes simplex virus type 2 glycoprotein gB; poliovirus 1 VPI (Emini et al., 1983, Nature 304:699); an envelope glycoprotein of HIV I; hepatitis B surface antigen; diptheria toxin; streptococcus 24M epitope; gonococcal pilin; pseudorabies virus g50 (gpD); pseudorabies virus II (gpB); pseudorabies virus gIll (gpC); pseudorabies virus glycoprotein H; pseudorabies virus glycoprotein E; transmissible gastroenteritis glycoprotein 195; transmissible gastoenteritis matrix protein; swine rotavirus glycoprotein 38; swine parvovirus capsid protein; Serpulina hyodysenteriae protective antigen; bovine viral diarrhea glycoprotein 55; Newcastle disease virus hemagglutinin-neuraminidase; swine flu hemagglutinin; swine flu neuraminidase; antigens of foot and mouth disease virus; antigens of hog cholera virus; antigens of swine influenza virus; antigens of African swine fever virus; *Mycoplasma hyopneumoniae*; antigens of infectious bovine rhinotracheitis virus (e.g., infectious bovine rhinotracheitis virus glycoprotein E or glycoprotein G); antigens of infectious laryngotracheitis virus (e.g., infectious laryngotracheitis virus glycoprotein G or glycoprotein I); a glycoprotein of La Crosse virus; antigens of neonatal calf diarrhea virus; Venezuelan equine encephalomyelitis virus; punta toro virus; murine leukemia virus; mouse mammary tumor virus; hepatitis B virus core protein and/or hepatitis B virus surface antigen or a fragment or derivative thereof (see, e.g., U.K. Patent Publication No. GB 2034323A published Jun. 4, 1980; Ganem and Varmus, 1987, Ann. Rev. Biochem. 56:651-693; Tiollais et al., 1985, Nature 317:489-495); antigen of equine influenza virus or equine herpesvirus (e.g., equine influenza virus type A/Alaska 91 neuraminidase, equine influenza virus type A/Miami 63 neuraminidase; equine influenza virus type A/Kentucky 81 neuraminidase; equine herpes virus type 1 glycoprotein B; equine herpes virus type 1 glycoprotein D); antigen of bovine respiratory syncytial virus or bovine parainfluenza virus (e.g., bovine respiratory syncytial virus attachment protein (BRSV G); bovine respiratory syncytial virus fusion protein (BRSV F); bovine respiratory syncytial virus nucleocapsid protein (BRSV N); bovine parainfluenza virus type 3 fusion protein; the bovine parainfluenza virus type 3 hemagglutinin neuraminidase); bovine viral diarrhea virus glycoprotein 48 or glycoprotein 53.

Other non-limiting examples of antigens include KS 1/4 pan-carcinoma antigen, ovarian carcinoma antigen (CA 125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, Colorectal tumor-associated antigens such as: CEA, TAG-72, CO17-1A; GICA 19-9, CTA- and LEA, Burkitt's lymphoma antigen-38.13, CD19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA) such as virally-induced tumor antigens including T-antigen DNA tumor viruses and envelope antigens of RNA tumor viruses, oncofetal antigen-alpha-fetoprotein such as CEA of colon, bladder tumor oncofetal antigen, differentiation antigen such as human lung carcinoma antigen L6, L20, antigens of fibrosarcoma, human leukemia T cell antigen-Gp37, neoglycoprotein, sphingolipids, breast cancer antigen such as EGFR (Epidermal growth factor receptor), HER2 antigen (p185HER2), EphA2 receptor, polymorphic epithelial mucin (PEM), malignant human lymphocyte antigen-APO-1, differentiation antigen such as I antigen found in fetal erthrocytes and primary endoderm, I(Ma) found in gastric adenocarcinomas, M18 and M39 found in breast epithelium, SSEA-1 found in myeloid cells, VEP8, VEP9, Myl, VIM-D5, and D156-22 found in colorectal cancer, TRA-1-85 (blood group H), C14 found in colonic adenocarcinoma, F3 found in lung adenocarcinoma, AH6 found in gastric cancer, Y hapten, Ley found in embryonal carcinoma cells, TL5 (blood group A), EGF receptor, E1 series (blood group B) found in pancreatic cancer, FC10.2 found in embryonal carcinoma cells, gastric adenocarcinoma, CO-514 (blood group Lea) found in adenocarcinoma, NS-10 found in adenocarcinomas, CO-43 (blood group Leb), G49, 19.9 found in colon cancer, gastric cancer mucins, TSA7 found in myeloid cells, R24 found in melanoma, 42, GD3, D1.1, OFA-1, GM2, OFA-2, GD2, M1:22:25:8 found in embryonal carcinoma cells and SSEA-3, SSEA-4 found in 4-8-cell stage embryos.

In other embodiments, the heterologous molecule is an antibody that specifically binds to an antigen associated with a disease that one intends to prevent, treat and/or manage (e.g., an antibody that specifically binds to a viral antigen, bacterial antigen, parasitic antigen, or cancer antigen). Non-limiting examples of such antibodies include anti-CD34 antibody, anti-CD56 antibody, anti-CD8 antibody, anti-CD22 antibody, anti-CD20 antibody, anti-CD19 antibody, anti-CD3 antibody, anti-EGFR antibody, anti-HER2 antibody, anti-CD34 antibody, anti-ckit antibody, anti-flt3 antibody, anti-hemagglutinin antibody, anti-gp4 antibody, anti-gpl 20 antibody, and anti-HSV-II glycoprotein gB antibody. In other embodiments, the antibody immunospecifically binds to one of the antigens listed above. In some embodiments, the antibody specifically binds to a cellular antigen (e.g., a receptor or cell surface antigen) expressed by a cell that one desires to target. For example, the IL-15/IL-15Ra complex can be targeted to CD34+ progenitor cells with an anti-CD34 antibody to induce development of such cells into CD56+ NK cells. The IL-15/IL-15Ra complex can be targeted to CD56+NK cells with an anti-CD56 antibody to induce proliferation of such cells.

In some embodiments, the heterologous molecule increases protein stability. Non-limiting examples of such molecules include polyethylene glycol (PEG), Fc domain of an IgG immunoglobulin or a fragment thereof, or albumin that increase the half-life of IL-15 or IL-15Ra in vivo. In certain embodiments, the heterologous molecules is not an Fc domain of an immunoglobulin molecule or a fragment thereof.

In those IL-15/IL-15Ra complexes comprising a heterologous molecule, the heterologous molecule may be conjugated to IL-15 and/or IL-15Ra. In one embodiment, the heterologous molecule is conjugated to IL-15Ra. In another embodiment, the heterologous molecule is conjugated to IL-15.

The components of an IL-15/IL-15Ra complex may be directly fused, using either non-covalent bonds or covalent bonds (e.g., by combining amino acid sequences via peptide bonds), and/or may be combined using one or more linkers. In a specific embodiment, IL-15 and IL-15Ra are directly fused to each other using either non-covalent bonds or covalent bonds (e.g., by combining amino acid sequences via peptide bonds), and/or may be combined using one or more linkers. In specific embodiments, a polypeptide comprising IL-15 and IL-15Ra directly fused to each other using either non-covalent bonds or covalent bonds is functional (e.g., capable of specifically binding to the IL-15R βγ complex and inducing IL-15-mediated signal transduction and/or IL-15-mediated immune function). Linkers suitable for preparing the IL-15/IL-15Ra complexes comprise peptides, alkyl groups, chemically substituted alkyl groups, polymers, or any other covalently-bonded or non-covalently bonded chemical substance capable of binding together two or more components. Polymer linkers comprise any polymers known in the art, including polyethylene glycol ("PEG"). In some embodiments, the linker is a peptide that is 1, 2, 3, 4, 5, 6, 7, 8, 9, 10, 11, 12, 13, 14, 15, 16, 17, 18, 19, 20 or more amino acids long. In a specific embodiment, the linker is long enough to preserve the ability of IL-15 to bind to the IL-15Ra. In other embodiments, the linker is long enough to preserve the ability of the IL-15/IL-15Ra complex to bind to the βγ receptor complex and to act as an agonist to mediate IL-15 signal transduction.

The present invention relates to Therapeutic Agents comprising IL-15/IL-15Ra complexes for use in the methods described herein. In particular embodiments, IL-15/IL-15Ra complexes are pre-coupled prior to use in the methods described herein (e.g., prior to contacting cells with the IL-15/IL-15Ra complexes or prior to administering the IL-15/IL-15Ra complexes to a subject). In other embodiments, the IL-15/IL-15Ra complexes are not pre-coupled prior to use in the methods described herein. In specific embodiments, the IL-15/IL-15Ra complex is administered in combination with a vaccine composition to enhance the immune response elicited by the administration of the vaccine composition to a subject. In a specific embodiment, an Agonistic Therapeutic Agent comprising IL-15 and IL-15Ra directly fused to each other is administered in combination with a vaccine composition to enhance an immune response elicited by administration of the vaccine composition to a subject.

5.1.2. Nucleic Acids

The invention provides Therapeutic Agents that are nucleic acids that encode IL-15 and IL-15Ra. The nucleic acids encode IL-15 and IL-15Ra that are capable of covalently or noncovalently binding to each other to form the IL-15/IL-15Ra complexes described in Section 5.1.1, supra. Such IL-15/IL-15Ra complexes can bind to the βγ receptor complex, and induce IL-15-mediated signal transduction.

Nucleic acid sequences encoding native IL-15 are well known in the art and have been described, for a review, see, Fehniger and Caligiuri, Blood, 2001, 97:14-32, which is incorporated by reference herein in its entirety. For example, the nucleic acid sequences encoding native IL-15 can be readily found in publicly available publications and databases, e.g., National Center for Biotechnology Information website at ncbi.nlm.nih.gov. Nucleic acid sequences encoding native IL-15Ra have been described, e.g., see International Publication No. WO 95/30695, and can also be readily found in publicly available publications and databases, e.g., National Center for Biotechnology Information website at ncbi.nlm.nih.gov. Cloning techniques well known in the art can be used to generate nucleic acids encoding IL-15 and IL-15Ra. See, e.g., Ausubel et al., Current Protocols in Molecular Biology, John Wiley and Sons, Inc. (1995); Sambrook et al., Molecular Cloning, A Laboratory Manual (2d ed.), Cold Spring Harbor Press, Cold Spring Harbor, N.Y. (1989); Birren et al., Genome Analysis: A Laboratory Manual, volumes 1 through 4, Cold Spring Harbor Press, Cold Spring Harbor, N.Y. (1997-1999).

In one embodiment, the Therapeutic Agent comprises nucleic acids that encode native IL-15Ra. In another embodiment, the Therapeutic Agent comprises nucleic acids that encode an IL-15Ra derivative that is a soluble form of native IL-15Ra. In a specific embodiment, the Therapeutic Agent comprises nucleic acids that encode an IL-15Ra derivative that is a soluble form of IL-15Ra that lacks the transmembrane domain of native IL-15Ra, and optionally the intracellular domain of native IL-15Ra. In other embodiments, the Therapeutic Agents comprise nucleic acids that encode an IL-15Ra derivative that is the extracellular domain of native IL-15Ra or a fragment thereof. In certain embodiments, the Therapeutic Agents comprise nucleic acids that encode an IL-15Ra derivative that is a fragment of the extracellular domain comprising the sushi domain or exon 2 of native IL-15Ra. In some embodiments, Therapeutic Agents comprise nucleic acids that encode an IL-15Ra derivative comprising a fragment of the extracellular domain comprising the sushi domain or exon 2 of native IL-15Ra and at least one amino acid that is encoded by exon 3. In certain embodiments, the Therapeutic Agents comprise nucleic acids that encode an IL-15Ra derivative comprising a fragment of the extracellular domain comprising the sushi domain or exon 2 of native IL-15Ra and an IL-15Ra hinge region or a fragment thereof. In some embodiments, the Therapeutic Agents comprise nucleic acids that encode an IL-15Ra derivative that consists essentially of the sushi domain or exon 2 of the receptor. In a specific embodiment, Therapeutic Agents comprise nucleic acids comprising sequences encoding a chimeric polypeptide comprising IL-15 and IL-15Ra directly fused to each other. In another embodiment, the Therapeutic Agents comprise nucleic acids that encode an IL-15Ra derivative comprising a mutation in the extracellular domain cleavage site that inhibits cleavage by an endogenous protease that cleaves IL-15Ra. In a specific embodiment, Therapeutic Agents comprise nucleic acids that encode an IL-15Ra derivative comprising mutations (in the extracellular domain cleavage site) that inhibit cleavage by an endogenous protease. In a specific embodiment, Therapeutic Agents comprise nucleic acids comprising sequences that encode an IL-15Ra derivative, wherein an extracellular domain cleavage site of IL-15Ra is replaced with a heterologous domain (e.g., heterologous transmembrane domain) or a synthetic amino acid sequence that does not allow cleavage and generation of soluble IL-15Ra. In certain embodiments; the extracellular domain cleavage site of IL-15Ra that is cleaved by an endogenous processing enzyme is mutated to inhibit cleavage and generation of soluble IL-15Ra. In one embodiment, the extracellular domain cleavage site of IL-15Ra is replaced with a heterologous extracellular domain cleavage site (e.g., heterologous transmembrane domain that is recognized and cleaved by another enzyme unrelated to the endogenous processing enzyme that cleaves IL-15Ra).

In a specific embodiment, the Therapeutic Agents comprise nucleic acids that encode IL-15 and/or IL-15Ra that are optimized, e.g., by codon/RNA optimization, replacement with heterologous signal sequences, and elimination of mRNA instability elements. Methods to generate optimized nucleic acids encoding IL-15 and IL-15Ra for expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, for IL-15 and IL-15Ra. The contents of each of these references are incorporated by reference herein in its entirety. See also U.S. Provisional Application No. 60/812,566, filed on Jun. 9, 2006, and 60/758,819, filed on Jan. 13, 2007, and International Patent Application Publication No. WO 2007/084342, which are also incorporated by reference herein in their entireties. For example, potential splice sites and instability elements (e.g., A/T or A/U rich elements) within the RNA of IL-15 and IL-15Ra can be mutated without altering the amino acids encoded by the nucleic acid sequences to increase stability of the RNA for expression. The alterations utilize the degeneracy of the genetic code, e.g., using an alternative codon for an identical amino acid. In some embodiments, it may be desirable to alter one or more codons to encode a conservative mutation, e.g., a similar amino acid with similar chemical structure and properties and/or function as the original amino acid. Such methods can increase expression of IL-15 and/or IL-15Ra proteins by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of IL-15 and/or IL-15Ra proteins encoded by native nucleic acid sequences.

Further, the native signal peptide sequence of IL-15 and/or IL-15Ra can be replaced with a heterologous signal peptide, e.g., a signal peptide of human GM-CSF (see FIGS. 8A-D), tissue plasminogen activator (tPA) (see FIGS. 5A-D), preprolactin, growth hormone or an immunoglobulin protein (e.g., IgE). In a specific embodiment, the signal peptide of IL-15 is replaced with the signal sequence of tPA. In other specific embodiments, the signal peptide of IL-15 is replaced with the signal peptide of human GM-CSF. Such alternations can increase expression of IL-15 and/or IL-15Ra proteins/polypeptides by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of IL-15 and/or IL-15Ra proteins with the respective native signal peptide, as measured/detected by a technique known to one of skill in the art, e.g., ELISA.

In some embodiments, an optimized nucleotide sequence encoding IL-15 or IL-15Ra hybridizes to the nucleotide sequence encoding native IL-15 or IL-15Ra, respectively. In specific embodiments, an optimized nucleotide sequence encoding IL-15 or IL-15Ra hybridizes under high stringency conditions to a nucleotide sequence encoding native IL-15 or IL-15Ra, respectively, or a fragment thereof. In a specific embodiment, an optimized nucleotide sequence encoding IL-15 or IL-15Ra hybridizes under high stringency, intermediate or lower stringency hybridization conditions to a nucleotide sequence encoding native IL-15 or IL-15Ra, respectively, or a fragment thereof. Information regarding hybridization conditions have been described, see, e.g., U.S. Patent Application Publication No. US 2005/0048549 (e.g., paragraphs 72-73).

The present invention provides nucleic acids encoding IL-15, IL-15Ra, and a heterologous molecule in a form that allows IL-15 to covalently or noncovalently bind to the IL-15Ra to form IL-15/IL-15Ra complexes. In some embodiments, the heterologous molecule is an antigen associated with a disease that one intends to prevent, treat and/or manage. Non-limiting examples of such antigens include those listed above in Section 5.1.1. In other embodiments, the heterologous molecule is an antibody that specifically binds to an antigen associated with a disease that one intends to prevent, treat and/or manage. Non-limiting examples of such antibodies include those listed above in Section 5.1.1 and those known in the art. In some embodiments, the antibody specifically binds to a cellular surface antigen (e.g., a receptor) expressed by a cell that one desires to target. In some embodiments, the heterologous molecule increases protein stability. Non-limiting examples of such molecules include polyethylene glycol (PEG), Fe domain of an IgG immunoglobulin or a fragment thereof, or albumin that increase the half-life of IL-15 or IL-15Ra in vivo. In certain embodiments, the heterologous molecules is not an Fe domain of an immunoglobulin molecule or a fragment thereof.

In those IL-15/IL-15Ra complexes comprising a heterologous molecule, the heterologous molecule may be conjugated to IL-15 and/or IL-15Ra. In one embodiment, the heterologous molecule is conjugated to IL-15Ra. In another embodiment, the heterologous molecule is conjugated to IL-15.

In specific embodiments, IL-15 and IL-15Ra are encoded by one nucleic acid construct (e.g., bicistronic construct). In some embodiments, IL-15 and IL-15Ra are encoded by one nucleic acid construct comprising a single open reading frame (ORF) of IL-15 and IL-15Ra. In some embodiments, IL-15 or IL-15Ra encoded by a nucleic acid construct may be conjugated to a nucleic acid encoding a heterologous molecule, such as an antigen or an antibody of interest. In other embodiments, IL-15 and IL-15Ra are encoded by two nucleic acid constructs, wherein a first nucleic acid construct encodes IL-15 and a second nucleic acid construct encodes IL-15Ra. The IL-15 encoded by the first nucleic acid construct may be conjugated to a nucleic acid encoding a heterologous molecule, such as an antigen or an antibody of interest. Alternatively, or in addition, the IL-15Ra encoded by the second nucleic acid construct may be conjugated to a nucleic acid encoding a heterologous molecule, such as an antigen or an antibody of interest.

5.1.2.1. Constructs

The nucleic acids encoding IL-15 and/or IL-15Ra can be inserted into nucleic acid constructs for expression in mammalian cells, bacteria, yeast, and viruses. IL-15 and IL-15Ra can be recombinantly expressed from the same nucleic acid construct (e.g., using a bicistronic nucleic acid construct) or from different nucleic acid constructs (e.g., using monocistronic nucleic acid constructs). In one embodiment, IL-15 and IL-15Ra can be recombinantly expressed from a single nucleic acid construct comprising a single open reading frame (ORF) of IL-15 and IL-15Ra.

The nucleic acid constructs may comprise one or more transcriptional regulatory element(s) operably linked to the coding sequence of IL-15 and/or IL-15Ra. The transcriptional regulatory elements are typically 5' to the coding sequence and direct the transcription of the nucleic acids encoding IL-15 and/or IL-15Ra. In some embodiments, one or more of the transcriptional regulatory elements that are found in nature to regulate the transcription of the native IL-15 and/or native IL-15Ra gene are used to control transcription. In other embodiments, one or more transcriptional regulatory elements that are heterologous to the native IL-15 and/or native IL-15Ra gene are used to control transcription. Any transcriptional regulatory element(s) known to one of skill in the art may be used. Non-limiting examples of the types of transcriptional regulatory element(s) include a constitutive promoter, a tissue-specific promoter, and an inducible promoter. In a specific embodiment, transcription is controlled, at least in part, by a mammalian (in some embodiments, human) transcriptional regulatory element(s). In a specific embodiment, transcription is controlled, at least in part, by a strong promoter, e.g., CMV.

Specific examples of promoters which may be used to control transcription include, but are not limited to, the SV40 early promoter region (Bernoist & Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); adenovirus (ADV), cytomegaloviros (CMV), bovine papilloma virus (BPV), parovirus B19p6 promoter, prokaryotic expression vectors such as the .beta.-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Omite et al., 1986, Cold Spring Harbor Symp, Quant. Biol. 50:399-409; MacDonald, 1987, Hepatology 7:425-515); insulin gene control region which is active in pancreatic beta cells (Hanaban, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al, 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378). In other aspects, an inducible promoter can be used.

The nucleic acid constructs also may comprise one or more post-transcriptional regulatory element(s) operably linked to the coding sequence of IL-15 and/or IL-15Ra. The post-transcriptional regulatory elements can be 5' and/or 3' to the coding sequence and direct the post-transcriptional regulation of the translation of RNA transcripts encoding IL-15 and/or IL-15Ra.

In another aspect, the nucleic acid construct can be a gene targeting vector that replaces a gene's existing regulatory region with a regulatory sequence isolated from a different gene or a novel regulatory sequence as described, e.g., in International Publication Nos. WO 94/12650 and WO 01/68882, which are incorporated by reference herein in their entireties.

The nucleic acid construct chosen will depend upon a variety of factors, including, without limitation, the strength of the transcriptional regulatory elements and the host cell to be used to express IL-15 and/or IL-15Ra. The nucleic acid constructs can be a plasmid, phagemid, cosmid, viral vector, phage, artificial chromosome, and the like. In one aspect, the vectors can be episomal or non-/homologously integrating vectors, which can be introduced into the appropriate host cells by any suitable means (transformation, transfection, conjugation, protoplast fusion, electroporation, calcium phosphate-precipitation, direct microinjection, etc.) to transform them.

The nucleic acid constructs can be a plasmid or a stable integration vector for transient or stable expression of IL-15 and/or IL-15Ra in host cells. For stable expression, the vector can mediate chromosomal integration at a target site or a random chromosomal site. Non-limiting examples of host cell-vector systems that may be used to express IL-15 and/or IL-15Ra include mammalian cell systems infected with virus (e.g., vaccinia virus, adenovirus, retroviruses, lentiviruses, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker. In some embodiments, the nucleic acid constructs include a selectable marker gene including, but not limited to, neo, gpt, dhfr, ada, pac, hyg, CAD and hisD.

The nucleic acid constructs can be monocistronic or multicistronic. A multicistronic nucleic acid construct may encode 2, 3, 4, 5, 6, 7, 8, 9, 10 or more, or in the range of 2-5, 5-10 or 10-20 genes/nucleotide sequences. For example, a bicistronic nucleic acid construct may comprise in the following order a promoter, a first gene (e.g., IL-15), and a second gene and (e.g. IL-15Ra). In such a nucleic acid construct, the transcription of both genes is driven by the promoter, whereas the translation of the mRNA from the first gene is by a cap-dependent scanning mechanism and the translation of the mRNA from the second gene is by a cap-independent mechanism, e.g. by an IRES.

Techniques for practicing aspects of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning Volumes I and II (Glover, Ed. 1985):Oligonucleotide Synthesis (Gait, Ed. 1984): Nucleic Acid Hybridization (Hames & Higgins, Eds. 1984); Transcription and Translation (Hames & Higgins, Eds. 1984); Animal Cell Culture (Freshney, Ed. 1986; Immobilized Cells and Enzymes (IRL Press, 1986); Perbal, A Practical Guide to Molecular Cloning (1984); Gene Transfer Vectors for Mammalian Cells (Miller & Calos, Eds. 1987, Cold Spring Harbor Laboratory); Methods in Enzymology, Volumes 154 and 155 (Wu & Grossman, and Wu, Eds., respectively), (Mayer & Walker, Eds., 1987); Immunochemical Methods in Cell and Molecular Biology (Academic Press, London, Scopes, 1987), Expression of Proteins in Mammalian Cells Using Vaccinia Viral Vectors in Current Protocols in Molecular Biology, Volume 2 (Ausubel et al., Eds., 1991).

The nucleic acid construct comprising nucleic acids encoding IL-15 and/or IL-15Ra can be administered in vivo to a mammal or transfected into primary or immortalized cells in culture. In certain aspects, the nucleic acid constructs comprising nucleic acids encoding IL-15 and/or IL-15Ra are administered to a mammal for recombinant expression of IL-15 and IL-15Ra in vivo to enhance IL-15 mediated signal transduction and to enhance an immune function associated with IL-15 signaling in vivo. In other aspects, the nucleic acids encoding IL-15 and/or IL-15Ra are administered in combination with a vaccine composition to enhance the immune response elicited by the administration of the vaccine composition to a subject.

The nucleic acid constructs comprising nucleic acids encoding IL-15 and/or IL-15Ra can be used to generate cells that express IL-15 and IL-15Ra for enhancement of an immune function in a subject. In particular, such cells can transpresent the IL-15/-15Ra complex on the cell surface to adjacent cells that express the by receptor complex, thus inducing IL-15 signal transduction. In some embodiments, the cells are primary cells (e.g., tumor cells isolated from a patient). In other embodiments, the cells are mammalian cell lines.

In another aspect, the nucleic acids encoding IL-15 and/or IL-15Ra can be used to generate mammalian cells that recombinantly express IL-15 and IL-15Ra in high amounts for the isolation and purification of IL-15 and IL-15Ra, preferably IL-15 and the IL-15Ra are associated as complexes. In one embodiment, high amounts of IL-15/IL-15Ra complexes refer to amounts of IL-15/IL-15Ra complexes expressed by cells that are at least 1 fold, 2 fold, 3 fold, 4 fold, 5 fold, d fold, 7 fold, 8 fold, 9 fold, 10 fold, 20 fold, or more than 20 fold higher than amounts of IL-15/IL-15Ra complexes expressed endogenously by control cells (e.g., cells that have not been genetically engineered to recombinantly express IL-15, IL-15Ra, or both IL-15 and IL-15Ra, or cells comprising an empty vector). In a specific embodiment, the IL-15Ra is the soluble form of IL-15Ra. In a specific embodiment, the IL-15Ra is the soluble form of IL-15Ra associated with IL-15 in a stable heterodimer, which increases yields and simplifies production and purification of bioactive heterodimer IL-15/soluble IL-15Ra cytokine. Recombinant IL-15 and IL-15Ra can be purified using methods of recombinant protein production and purification are well known in the art, e.g., see International Publication No. WO 07/070488, which is incorporated by reference herein in its entirety. Briefly, the polypeptide can be produced intracellularly, in the periplasmic space, or directly secreted into the medium. Cell lysate or supernatant comprising the polypeptide can be purified using, for example, hydroxylapatite chromatography, gel electrophoresis, dialysis, and affinity chromatography, Other techniques for protein purification such as fractionation on an ion-exchange column, ethanol precipitation, Reverse Phase HPLC, chromatography on silica, chromatography on heparin SEPHAROSE™ (gel filtration substance; Pharmacia Inc., Piscataway, N.J.) chromatography on an anion or cation exchange resin (such as a polyaspartic acid column), chromatofocusing, SDS-PAGE, and ammonium sulfate precipitation are also available.

In some embodiments, IL-15 and IL-5Ra are synthesized or recombinantly expressed by different cells and subsequently isolated and combined to form an IL-15/IL-15Ra complex, in vitro, prior to administration to a subject in other embodiments, IL-15 and IL-15Ra are synthesized or recombinantly expressed by different cells and subsequently isolated and simultaneously administered to a subject an IL-15/IL-15Ra complex in situ or in vivo. In yet other embodiments, IL-15 and IL-15Ra are synthesized or expressed together by the same cell, and the IL-15/IL-15Ra complex formed is isolated.

5.1.3. Antibodies

The present invention provides antibodies that specifically bind to IL-15/IL-15Ra complexes. In a specific embodiment, the present invention provides antibodies that specifically bind to the complex formed when IL-15 and IL-15Ra bind to each other. In a more specific embodiment, the present invention provide antibodies that specifically bind to the complex formed between IL-15 and IL-15Ra and prevent or reduce IL-15-mediated signal transduction. Such antibodies, in accordance with this embodiment, may block (sterically or non-sterically) the binding of the complex of IL-15 and IL-15Ra with the βγ (or CD122/CD132) receptor complex of the IL-15 receptor. In a specific embodiment, the antibody reduces the binding of the IL-15/IL-15Ra complex to the βγ complex by at least 1 fold, 2 fold, 3 fold, 4 fold, 5 fold, 6 fold, 7 fold, 8 fold, 9 fold, 10 fold, 11 fold, 12 fold, 13 fold, 14 fold, 15 fold, 16 fold 17 fold, 18 fold, 19 fold 20 fold, 30 fold, 40 fold, 50 fold, 60 fold, 70 fold, 80 fold, 90 fold, 100 fold, 500 fold, or 1000 fold relative to a negative control (e.g., binding affinity of the IL-15/IL-15Ra complex to the fry receptor complex in the absence of the antibody) as determined by methods well known in the art, e.g., ELISA, cell-based assays including flow cytometry, KinEx A assay, and plasmon surface resonance assay (e.g., BIAcore assay).

Antibodies that specifically bind to the IL-15/IL-15Ra complex can be produced by any method well known in the art, e.g., as described in U.S. Pat. Nos. 5,807,715, 6,331,415, and 6,818,216; U.S. Patent Application Publication Nos. US 2002/0098189, US 2004/0028685, US 2005/0019330, and US 2007/0086943; International Publication No. WO 02/46237; and Harlow et al., Antibodies. A Laboratory Manual, (Cold Spring Harbor Laboratory Press, 2nd ed. 1988); Hammerling, et al, in: Monoclonal Antibodies and T-Cell Hybridomas 563-681 (Elsevier, N.Y., 1981) (said references are incorporated by reference herein in their entireties).

The antibodies that specifically bind to IL-15/IL-15Ra complexes can be administered to a subject to prevent IL-15/IL-15Ra complexes from binding to the βγ receptor complex and from inducing IL-15-mediated signal transduction. Thus, such antibodies can suppress an immune function that is associated with IL-15 signal transduction. In some embodiments, antibodies described herein are useful for detecting the presence of IL-15/IL-15Ra complexes.

5.1.4. Cells

Cells can be engineered to express the protein(s) encoded by the nucleic acid constructs described in Section 5.1.2, supra, in high amounts. In one embodiment, high amounts of IL-15/IL-15Ra complexes refer to amounts of IL-15/IL-15Ra complexes expressed by cells that are at least 1 fold, 2 fold, 3 fold, 4 fold, 5 fold, 6 fold, 7 fold, 8 fold, 9 fold, 10 fold, 20 fold, or more than 20 fold higher than amounts of IL-15/IL-15Ra complexes expressed endogenously by control cells (e.g., cells that have not been genetically engineered to recombinantly express IL-15, IL-15Ra, or both IL-15 and IL-15Ra, or cells comprising an empty vector). In addition, cells can be engineered to express the antibodies described in Section 5.1.3, supra, using techniques well-known to one of skill in the art, see, e.g., U.S. Pat. Nos. 5,807,715, 6,331,415, and 6,818,216; U.S. Patent Application Publication Nos. US 2002/0098189, US 2004/0028685, US 2005/0019330, and US 2007/0086943; International Publication No. WO 02/46237; and Harlow et al., Antibodies. A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references are incorporated by reference herein in their entireties). The host cells chosen for expression of nucleic acids will depend upon the intended use of the cells. Factors such as whether a cell glycosylates similar to cells that endogenously express, e.g., IL-15 and/or IL-15Ra, may be considered in selecting the host cells.

In one embodiment, the invention also provides for a method of increasing the yield and bioactivity of IL-15 by constructing cell lines expressing both IL-15 and soluble IL-15Ra, and purifying the stable heterodimer, which can be used in vitro or in vivo, e.g., can be administered to a human. In one embodiment, the stability of IL-15 is increased when produced from cell lines recombinantly expressing both IL-15 and IL-15Ra.

Non-limiting examples of hosts cells that can be used to express the protein(s) encoded by the nucleic acid constructs described in Section 5.1.2, supra, or the antibodies described in Section 5.1.3, supra, include mammalian cells, bacterial cells, yeast cells, primary cells, immortalized cells, and insect cells. In a specific embodiment, the host cells are a mammalian cell line. Examples of mammalian cell lines include, but are not limited to, COS, CHO, HeLa, NIH3T3, HepG2, MCF7, HEK, 293T, RD, PC12, hybridomas, pre-B cells, 293, 293H, K562, SkBr3, BT474, A204, M07Sb, TFβ1, Raji, Jurkat, MOLT-4, CTLL-2, MC-IXC, SK-N-MC, SK-N-MC, SK-N-DZ, SH-SY5Y, CI27, N0, and BE(2)-C cells. Other mammalian cell lines available as hosts for expression are known in the art and include many immortalized cell lines available from the American Type Culture Collection (ATCC). In another embodiment, the host cells are immortalized cell lines derived from a subject. In another embodiment, the host cells are primary or secondary cells from a subject. In a particular embodiment, the host cells are cancer cells. In another embodiment, the host cells are epithelial cells or endothelial cells. In another embodiment, the host cells are fetal/embryonic cells. In some embodiments, the host cells are progenitor cells. In some embodiments, the host cells are lymphocytes (e.g., T cells and B cells). In another embodiment, the host cells are stem cells.

In yet another embodiment, the host cells engineered to express the nucleic acid constructs of Section 5.1.2, supra, are from an adult.

In some embodiments, isolated cells are utilized herein. In a specific embodiment, the isolated cells are at least 80%, 90%, 95% or 98% free of a different cell type as measured by a technique known to one of skill in the art, such as flow cytometry. In other words, at least 80%, 90%, 95% or 98% of the isolated cells are of the same cell type.

In a specific embodiment, the nucleic acid constructs encoding IL-15 or IL-15Ra can be co-transfected or transfected into the same host cells or different host cells. Optionally, a nucleic acid construct comprising nucleic acids encoding a selectable marker gene can also be transfected into the same cells to select for transfected cells. If the nucleic acid constructs comprising nucleic acids encoding IL-15 and IL-15Ra are transfected into different cells, IL-15 and IL-15Ra expressed by the different cells can be isolated and contacted with each other under conditions suitable to form IL-15/IL-15Ra complexes described in Section 5.1.1, supra. Any techniques known to one of skill in the art can be used to transfect or transducer host cells with nucleic acids including, e.g., transformation, transfection, conjugation, protoplast fusion, electroporation, calcium phosphate-precipitation, direct microinjection, and infection with viruses, including but not limited to adenoviruses, lentiviruses, and retroviruses.

For long-term, high-yield production of a recombinant of IL-15 and IL-15Ra polypeptides, stable cell lines can be generated. For example, cell lines can be transformed using the nucleic acid constructs of Section 5.1.2 which may contain a selectable marker gene on the same or on a separate nucleic acid construct. The selectable marker gene can be introduced into the same cell by co-transfection. Following the introduction of the vector, cells are allowed to grow for 1-2 days in an enriched media before they are switched to selective media to allow growth and recovery of cells that successfully express the introduced nucleic acids. Resistant clones of stably transformed cells may be proliferated using tissue culture techniques well known in the art that are appropriate to the cell type. In a particular embodiment, the cell line has been adapted to grow in serum-free medium. In one embodiment, the cell line has been adapted to grow in serum-free medium in shaker flasks. In one embodiment, the cell line has been adapted to grow in stir or rotating flasks. In certain embodiments, the cell line is cultured in suspension. In particular embodiments, the cell line is not adherent or has been adapted to grow as nonadherent cells. In certain embodiments, the cell line has been adapted to grow in low calcium conditions. In some embodiments, the cell line is cultured or adapted to grow in low serum medium.

In a specific embodiment, the host cell recombinantly expresses IL-15 and the full length IL-15Ra. In another specific embodiment, the host cell recombinantly expresses IL-15 and the soluble form of IL-15Ra. In another specific embodiment, the host cell recombinantly expresses IL-15 and a membrane-bound form of IL-15Ra which is not cleaved from the surface of the cell and remains cell associated. In some embodiments, the host cell recombinantly expressing IL-15 and/or IL-15Ra (full-length or soluble form) also recombinantly expresses another polypeptide (e.g., a cytokine or fragment thereof).

In a specific embodiment, a particularly preferred method of high-yield production of a recombinant polypeptide of the present invention is through the use of dihydro folate reductase (DHFR) amplification in DHFR-deficient CHO cells, by the use of successively increasing levels of methotrexate as described in U.S. Pat. No. 4,889,803, which is incorporated by reference herein in its entirety. The polypeptide obtained from such cells may be in a glycosylated form.

In a specific embodiment, the nucleic acid constructs are suitable for introduction and expression in primary cells isolated from a subject. The primary cells are engineered to express IL-15 and IL-15Ra. In a specific embodiment, the primary cells express IL-15 and the full length IL-15Ra. In a particular embodiment the IL-15Ra contains a mutation that eliminated the extracellular domain cleavage site or that replaces the native extracellular domain cleavage site with a heterologous extracellular domain cleavage site. When administered to a subject, such cells can transpresent the IL-15/IL-15Ra complex to adjacent cells in vivo, thus mediating IL-15 signal transduction and enhancing an immune system function mediated by IL-15 signaling. In another specific embodiment, the primary cells express IL-15 and the soluble form of IL-15Ra.

In a particular embodiment, the primary cells are cancer cells: (i) isolated from a subject (diagnosed with cancer); (ii) engineered to recombinantly express either IL-15 or IL-15Ra (full-length or soluble form) or both; and (iii) irradiated prior to administration to a cancer patient for enhancing an immune response in the subject to antigens of the cancer cells. In a specific embodiment, the primary cells isolated from a subject are further engineered to recombinantly express another therapeutic polypeptide, e.g., a cytokine (e.g., IL-1, IL-2, IL-6, IL-11, IL-12, IL-13, TNF-alpha, GM-CSF, interferon-α, interferon-β, or interferon-γ), a growth factor or a fragment or derivative thereof. In a specific embodiment, the primary cells isolated from a subject are further engineered to recombinantly express an antigen of a cancer. In one embodiment, irradiated cells can be administered to the same subject or to a different subject from which the cells were obtained. In a particular embodiment, the primary cells are isolated from a tumor of the subject. In one embodiment, cells of a cancer cell line can be engineered to recombinantly express either IL-15 or IL-15Ra or both, wherein the cells are irradiated before administration to a subject.

In some embodiments, the present invention provides for methods for making cells described herein. In one embodiment, the present invention relates to a method for making irradiated cancer cells co-expressing IL-15 and IL-15Ra comprising the steps of: (i) isolating cancer cells from a subject (diagnosed with cancer); (ii) engineering said cancer cells to recombinantly express either IL-15, or IL-15Ra (full length or soluble form), or both; and (iii) irradiating said cancer cells. In some embodiment, the present invention relates to a method for making irradiated cancer cells co-expressing IL-15 and IL-15Ra comprising the steps of: (i) isolating cancer cells from a subject (diagnosed with cancer); (ii) introducing a nucleic acid construct(s) encoding recombinant IL-15 or a derivative thereof and human IL-15Ra or a derivative thereof; and (iii) irradiating said cancer cells. In particular embodiments, the irradiated cancer cells are administered to the subject from which the cancer cells were isolated (or obtained).

In one embodiment, the present invention relates to a method for making host cells capable of growing in serum-free medium comprising the steps of: (i) engineering host cells to recombinantly express IL-15 and/or IL-15Ra (full length or soluble form), (ii) culturing the host cells in medium comprising a 1:1 ratio of old medium (comprising 10% serum) to new medium; and (iii) repeating step (ii) until the host cells grow at a desired growth rate, wherein the new medium is serum-free, and wherein the desired growth rate is the desired growth rate is the growth rate the host cells grows when cultured in medium comprising 10% serum.

In some embodiments, the present invention encompasses a cell that recombinantly expresses a mammalian IL-15 or a derivative thereof and a mammalian IL-15Ra or a derivative thereof, wherein the cell expresses at least 0.6 pg of mammalian IL-15 or a derivative thereof. In certain embodiments, the cell expresses at least 0.1 pg, 0.5 pg, 1 pg, or 2 pg of mammalian IL-15 or a derivative thereof. In some embodiments, the cell expresses approximately 0.1 pg to 0.6 pg, 0.5 pg to 1 pg, 0.5 pg to 2 pg, or 0.1 pg to 2 pg of mammalian IL-15 or a derivative thereof. In particular embodiments, the cell recombinantly expresses a mammalian IL-15 or a derivative thereof that is more stable than endogenous IL-15 produced by a cell not recombinantly expressing both mammalian IL-15 and IL-15Ra. In specific embodiments, the protein stability of recombinant mammalian IL-15 produced by such a cell is at least 1 fold, 1.5 fold, 2 fold, 3 fold, 4 fold, 5 fold, 6 fold, 7 fold, 8 fold, 9 fold, 10 fold, 20 fold, 50 fold, or 100 fold more stable than endogenous IL-15 produced by a cell not recombinantly expressing both mammalian IL-15 and IL-15Ra as measured by a technique known to one of skill in the art, e.g., high performance size exclusion chromatography (HPSEC). In some embodiments, the mammalian IL-15 or derivative thereof is stable at 32° C. or 37° C. for 6 hours, 12 hours, 1 day, 2 days, 5 days, 7 days, 14 days, 1 month, 2 months or more. In particular embodiments, the cell recombinantly expresses a mammalian IL-15 or a derivative thereof that is degraded at a slower rate than endogenous IL-15 produced by a cell not recombinantly expressing both mammalian IL-15 and IL-15Ra. In specific embodiments, the protein degradation rate of recombinant mammalian IL-15 (in vitro or in vivo) produced by such a cell is at least 1 fold, 1.5 fold, 2 fold, 3 fold, 4 fold, 5 fold, 6 fold, 7 fold, 8 fold, 9 fold, 10 fold, 20 fold, 50 fold, or 100 fold smaller than the protein degradation rate of endogenous IL-15 produced by a cell not recombinantly expressing both mammalian IL-15 and IL-15Ra as measured by a technique known to one of skill in the art, e.g., ELISA, western blot or HPSEC.

In some embodiments, the present invention encompasses a cell that recombinantly expresses a mammalian IL-15 or a derivative thereof and a mammalian IL-15Ra or a derivative thereof, wherein the cell grows in serum-free media. In certain embodiments, the cell expresses at least 0.6 pg of mammalian IL-15 or a derivative thereof. In certain embodiments, the cell expresses at least 0.1 pg, 0.5 pg, 1 pg, or 2 pg of mammalian IL-15 or a derivative thereof. In some embodiments, the cell expresses approximately 0.1 pg to 0.6 pg, 0.5 pg to 1 pg, 0.5 pg to 2 pg, or 0.1 pg to 2 pg of mammalian IL-15 or a derivative thereof.

In some embodiments, the present invention relates to a population of cells that recombinantly expresses a mammalian IL-15 or a derivative thereof and a mammalian IL-15Ra or a derivative thereof, wherein the population of cells express at least 600 ng/million cells of mammalian IL-15 or a derivative thereof. In specific embodiments, the population of cells express at least 150 ng/million cells per day cells of mammalian IL-15 or a derivative thereof. In some embodiments, the population of cells express at least 50 ng/million cells per day, 100 ng/million cells per day, 200 ng/million cells per day, 250 ng/million cells per day, or 300 ng/million cells per day cells of mammalian IL-15 or a derivative thereof. In particular embodiments, the population of cells express approximately 50 ng/million cells per day to 200 ng/million cells per day, 100 ng/million cells per day to 250 ng/million cells per day, or 50 ng/million cells per day to 300 ng/million cells per day cells of mammalian IL-15 or a derivative thereof. In certain embodiments, the population of cells express approximately 100 ng/million cells to 1000 ng/million cells, 500 ng/million cells to 1000 ng/million cells, 500 ng/million cells to 2000 ng/million cells, or 100 ng/million cells to 2000 ng/million cells of mammalian IL-15 or a derivative thereof.

In particular embodiments, the population of cells recombinantly expresses a mammalian IL-15 or a derivative thereof that is more stable than endogenous IL-15 produced by a cell not recombinantly expressing both mammalian IL-15 and IL-15Ra. In specific embodiments, the protein stability of recombinant mammalian IL-15 produced by such a population of cells is at least 1 fold, 1.5 fold, 2 fold, 3 fold, 4 fold, 5 fold, 6 fold, 7 fold, 8 fold, 9 fold, 10 fold, 20 fold, 50 fold, or 100 fold more stable than endogenous IL-15 produced by a population of cells not recombinantly expressing both mammalian IL-15 and IL-15Ra as measured by a technique known to one of skill in the art, e.g., high performance size exclusion chromatography (HPSEC). In some embodiments, the mammalian IL-15 or derivative thereof is stable at 32° C. or 37° C. for 6 hours, 12 hours, 1 day, 2 days, 5 days, 7 days, 14 days, 1 month, 2 months or more. In particular embodiments, the population of cells recombinantly expresses a mammalian IL-15 or a derivative thereof that is degraded at a slower rate than endogenous IL-15 produced by a cell not recombinantly expressing both mammalian IL-15 and IL-15Ra. In specific embodiments, the protein degradation rate of recombinant mammalian IL-15 (in vitro or in vivo) produced by such a population of cells is at least 1 fold, 1.5 fold, 2 fold, 3 fold, 4 fold, 5 fold, 6 fold, 7 fold, 8 fold, 9 fold, 10 fold, 20 fold, 50 fold, or 100 fold smaller than the protein degradation rate of endogenous IL-15 produced by a population of cells not recombinantly expressing both mammalian IL-15 and IL-15Ra as measured by a technique known to one of skill in the art, e.g., ELISA, western blot or HPSEC.

In some embodiments, the present invention relates to a population of cells that recombinantly expresses a mammalian IL-15 or a derivative thereof and a mammalian IL-15Ra or a derivative thereof, wherein the population of cells grows in serum-free media. In particular embodiments, the population of cells express at least 600 ng/million cells of mammalian IL-15 or a derivative thereof. In specific embodiments, the population of cells express at least 150 ng/million cells per day cells of mammalian IL-15 or a derivative thereof. In some embodiments, the population of cells express at least 50 ng/million cells per day, 100 ng/million cells per day, 200 ng/million cells per day, 250 ng/million cells per day, or 300 ng/million cells per day cells of mammalian IL-15 or a derivative thereof. In particular embodiments, the population of cells express approximately 50 ng/million cells per day to 200 ng/million cells per day, 100 ng/million cells per day to 250 ng/million cells per day, or 50 ng/million cells per day to 300 ng/million cells per day cells of mammalian IL-15 or a derivative thereof. In certain embodiments, the population of cells express approximately 100 ng/million cells to 1000 ng/million cells, 500 ng/million cells to 1000 ng/million cells, 500 ng/million cells to 2000 ng/million cells, or 100 ng/million cells to 2000 ng/million cells of mammalian IL-15 or a derivative thereof.

5.2. Polymers

The invention provides for any of the Therapeutic Agents described in Section 5.1 to be formulated with any natural polymer suitable for biomedical use, including poly-β-1→4-N-acetylglucosamine ("p-GlcNAc"). p-GlcNAc can be found in chitin and chitosan derived from shellfish, fungi, or microalgal sources. In a preferred embodiment, the p-GlcNAc is purified as described in U.S. Patent Application Publication Nos. US 2004/0220140 and US 2001/0055807 and U.S. Pat. Nos. 5,622,834; 5,623,064; 5,624,679; 5,686,115; 5,858,350; 6,599,720; 6,686,342; and 7,115,588, which are incorporated by reference herein in their entireties. In a specific embodiment, the polymer is in the form of fibers. However, other forms, such as powder, may be used.

Examples of suitable polymers for practicing the invention include, but are not limited to, cellulose-based polymers, xanthan, polyaramides, polyamides, polyimides, polyamide/imides, polyamidehydrazides, polyhydrazides, polyimidazoles, polybenzoxazoles, polyester/amide, polyester/imide, polycarbonate/amides, polycarbonate/imides, polysulfone/amides, polysulfone imides, and the like, copolymers and blends thereof. Other suitable classes of polymers that may be used include polyvinyledene fluorides and polyacrylonitriles. Examples of these polymers include those described in U.S. Pat. Nos. 4,705,540; 4,717,393; 4,717,394; 4,912,197; 4,838,900; 4,935,490; 4,851,505; 4,880,442; 4,863,496; and 4,961,539; and European Patent Application No. 0 219 878, all of which are incorporated by reference herein in there entireties. The polymers can include at least one of either of cellulose-based polymers, polyamides, polyaramides, polyamide/imides or polyimides. In certain embodiments, the polymers include polyaramides, polyester, urethan and polytetrafluoroethylene.

In some embodiments, polymerized N-acetylglucosamine or derivatives thereof are used. In a preferred embodiment, the polymer is poly-N-acetylglucosamine or a derivative thereof. In certain embodiments, the poly-N-acetylglucosamine has a β-1→4 configuration. In other embodiments, the poly-N-acetylglucosamine has an α-1→4 configuration.

In specific embodiments, the polymer is chitin, chitosan, cellulose, nylon or PET (polyethylene terepthlate).

In other specific embodiments, the polymer is biocompatible and/or biodegradable. Biocompatibility may be determined by a variety of techniques, including, but not limited to such procedures as the elution test, intramuscular implantation, or intracutaneous or systemic injection into animal subjects. Such tests are described in U.S. Pat. No. 6,686,342, which is incorporated by reference herein in its entirety, or equivalent tests as set forth in ISO-10993 guidances. Biodegradable polymers preferably degrade within about 1 day, 2 day, 5 day, 8 day, 12 day, 17 day, 25 day, 30 day, 35 day, 40 day, 45 day, 50 day, 55 day, 60 day, 65 day, 70 day, 75 day, 80 day, 85 day, 90 day, 95 day, or 100 days after administration or implantation into a patient.

In certain aspects of the invention, the polymer is immunoneutral.

In one embodiment, Therapeutic Agents or compositions thereof are formulated with purified polymers, which may be about 100%, 99.9%, 99.8%, 99.5%, 99%, 98%, 95%, 90%, 80%, 70%, 60%, 50%, 40%, 30%, or 20% pure. In a specific embodiment, the polymers used to formulate the Therapeutic Agents or compositions thereof are 90-100% pure.

In certain embodiments, the polymer that is used to formulate the Therapeutic Agent is not one or more of the following: an ionic synthetic hydrogel such as, but not limited to, crosslinked poly(AAn-acrylic acid) and poly(AAm-dimethylaminoethyl methacrylate), poly(vinyl alcohol) (PVA), poly(ethylene glycol) (PEG), poly(N-vynl pyrrolidone), poly(methoxy-PEG methacrylate). In certain embodiments, the polymer is not one or more of: a poly-L- amino acid, such as poly L lysine, poly L arginine, poly L glutamic acid, poly L histidine, poly D glutamic acid or a mixture thereof. In certain embodiments, the polymer is not one or more of: an alginate polymer, such as sodium alginate, calcium alginate, strontium alginate, barium alginate, magnesium alginate or any other alginate or a mixture thereof. In certain embodiments, the polymer is not derived from one or more of: a shell fish, a crustacean, insect, fungi and/or or yeasts. In certain embodiments, the polymers do not comprise collagen fibers. In certain embodiments, the polymers do not comprise elastin fibers. In certain embodiments, the polymers do not comprise block polymer polaxamer 407. In certain embodiments, the polymers do not comprise nondegradable polymeric matrices. In certain embodiments, the polymers do not comprise degradable polymeric matrices. In other embodiments, any of the above-referenced polymers are included in the Therapeutic Agents or compositions thereof. For example, in certain embodiments, the polymer that is used to formulate a Therapeutic Agent is one or more of the following: an ionic synthetic hydrogel such as, but not limited to, crosslinked poly(AAn-acrylic acid) and poly(AAm-dimethylaminoethyl methacrylate), poly(vinyl alcohol) (PVA), poly(ethylene glycol) (PEG), poly(N-vynl pyrrolidone), poly(methoxy-PEG methacrylate). In certain embodiments, the polymer is not one or more of: a poly-L-amino acid, such as poly L lysine, poly L arginine, poly L glutaric acid, poly L histidine, poly D glutamic acid or a mixture thereof. In certain embodiments, the polymer is one or more of: an alginate polymer, such as sodium alginate, calcium alginate, strontium alginate, barium alginate, magnesium alginate or any other alginate or a mixture thereof. In certain embodiments, the polymer is derived from one or more of: a shell fish, a crustacean, insect, fungi and/or or yeasts. In certain embodiments, the polymers does comprise collagen fibers. In certain embodiments, the polymers do comprise elastin fibers. In certain embodiments, the polymers do comprise block polymer polaxamer 407. In certain embodiments, the polymers do comprise nondegradable polymeric matrices. In certain embodiments, the polymers do comprise degradable polymeric matrices.

The polymers can be in the form of fibers. Fibers may be about 0.20, 0.25, 0.30, 0.35, 0.40, 0.54, 0.50, 0.55, 0.60, or 0.65 microns in thickness and/or diameter as determined by electron microscopy. In preferred embodiments the fibers are about 0.50 microns in width and range in length from about 20 to 100 microns as determined by electron microscopy, particularly, scanning electron microscopy. In another preferred embodiments the fibers are about 0.50 microns in width and range in length from about 50 to 100 microns as determined by electron microscopy, particularly, scanning electron microscopy. In yet another preferred embodiments the fibers are about 0.50 microns in width and range in length from about 75 to 100 microns as determined by electron microscopy, particularly, scanning electron microscopy.

In certain embodiments, at least 75%, at least 85%, at least 90%, or at least 95% of a Therapeutic Agent is formulated with one or more of the polymers listed above.

In one embodiment, the Therapeutic Agents comprise more than one type of polymer (e.g., poly-β-1→4-N-acetylglucosamine and cellulose).

5.2.1 Poly-1→4-N-Acetylglucosamine

A preferred polymer for use in combination with a Therapeutic Agent is poly-N-acetylglucosamine or a derivative thereof.

As used herein, poly-N-acetylglucosamine includes any polymer of N-acetylglucosamine and/or glucosamine covalently linked in a β-1→4 or an α-1→4 conformation and in any degree or form of crystallinity. In specific embodiments, poly-N-acetylglucosamine is (1) a semi-crystalline form of poly-N-acetylglucosamine; (2) a poly-N-acetylglucosamine comprising about 50 to about 150,000 N-acetylglucosamine monosaccharides covalently attached in a β-1→4 conformation and having a molecular weight of about 10,000 daltons to about 30 million daltons; (3) a poly-β-1→4-acetylglucosamine comprising about 50 to about 50,000 N-acetylglucosamine monosaccharides covalently attached in α-1→4 conformation and having a molecular weight of about 10,006 daltons to about 10 million daltons; (4) a poly-β-1→4-acetylglucosamine comprising about 50 to about 10,000 N-acetylglucosamine monosaccharides covalently attached in a β-1-+4 conformation and having a molecular weight of about 10,000 daltons to about 2 million daltons; (5) a poly-β-1→4-N-acetylglucosamine comprising about 50 to about 4,000 N-acetylglucosamine monosaccharides covalently attached in a β-1→4 conformation and having a molecular weight of about 10,000 daltons to about 800,000 daltons; and (6) deacetylated counterparts of of (1)-(5) above in which the degree of deacetylation ranges from 1%-99%, In specific embodiments, the degree of deacetylation is at least 10%, at least 20%, at least 30%, at least 40° %, at least 50%, at least 60%, at least 70%, at least 80%, or at least 90%.

Derivatives, such as chemical derivatives, of poly-β-1→4 N-acetylglucosamine may also be used to formulate the Therapeutic Agents. For example, sulfated poly-β-1→4 N-acetylglucosamine derivatives, phosphorylated poly-β-1→4 N-acetylglucosamine derivatives, or nitrated poly-β-1→4 N-acetylglucosamine derivatives may be used. Additionally, one or more of the monosaccharide units of the poly-β-1→4 N-acetylglucosamine may contain one or more sulfonyl groups one or more O-acyl groups. In addition, one or more of the monosaccharides of the deacetylated poly-β-1→4 N-acetylglucosamine may contain an N-acyl group. One or more of the monosaccharides of the poly-β-1→4 N-acetylglucosamine or of its deacetylated derivative, may contain an O-alkyl group. One or more of the monosaccharide units of the poly-β-1→4 N-acetylglucosamine may be an alkali derivative. One or more of the monosaccharide units of the deacetylated derivative of poly-β-1→4 No acetylglucosamine may contain an N-alkyl group. One or more of the monosaccharide units of the deacetylated derivative of poly-β-1→4 N-acetylglucosamine may contain at least one deoxyhalogen derivative. One or more of the monosaccharide units of the deacetylated derivative of poly-β-1→4 N-acetyltucosamine may form a salt. One or more of the monosaccharide units of the deacetylated derivative of poly-β-1→4 N-acetylglucosamine may form a metal chelate. Preferably, the metal is zinc. One or more of the monosaccharide units of the deacetylated derivative of poly-β-1→4 N-acetylglucosamine may contain an N-alkylidene or an N-arylidene group. Methods of making such derivatives are described in U.S. Pat. No. 5,623,064, which is incorporated by reference herein in its entirety.

In specific embodiments, poly-N-acetylglucosamine is obtained by a process comprising a) treating a microalga comprising a cell body and a poly-N-acetylglucosamine fiber with a biological agent (such as hydrofluoric acid) capable of separating the N-acetylglucosamine fiber from the cell body for a sufficient time so that the poly-N-acetylglucosamine fiber is released from the cell body; b) segregating the poly-N-acetylglucosamine fiber from the cell body; and c) removing contaminants from the segregated poly-N-acetylglucosamine fiber. Detailed descriptions of making poly-N-acetylglucosamine according to such methods are described in U.S. Patent Application Publication Nos. US 2004/0220140 and US 2001/055807, and U.S. Pat. Nos. 5,622,834; 5,623,064; 5,624,679; 5,686,115; 5,858,350; 6,599,720; 6,686,342; and 7,115,588, the contents of which are incorporated herein in their entireties.

As an alternative source to microalgal p-GlcNAc, p-GlcNAc purified from crustacean or fungal chitin or chitosan may be use to formulate a Therapeutic Agent according to the present invention.

Optionally, the p-GlcNAc is used in fiber form, for example as described above.

5.3. Compositions

The invention provides compositions comprising the Therapeutic Agents, including Agonistic Therapeutic Agents and Antagonist Therapeutic Agents. The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. The compositions comprise an effective amount of a Therapeutic Agent or a combination of Therapeutic Agents and a pharmaceutically acceptable carrier. In specific embodiments, the compositions comprise an effective amount of one or more Therapeutic Agents and a pharmaceutically acceptable carrier. In some embodiments, the composition further comprises an additional therapeutic, e.g., anti-cancer agent, anti-viral agent, anti-inflammatory agent, adjuvant. Non-limiting examples of such therapeutics are provided in Section 5.4.5, infra.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete) or, more preferably, MF59C.1 adjuvant available from Chiron, Emeryville, Calif.), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In one embodiment, water is a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

5.3.1. Formulations with Polymers

The present invention provides for compositions (and pharmaceutical compositions) comprising a Therapeutic Agent that are formulated with a polymer, such as described in Section 5.2, supra. Various formulations comprising a Therapeutic Agent and a polymer are described herein.

The polymers can be formulated as a gel, solid, liquid, sponge, foam, spray, emulsion, suspension, solution, mat, string, gauze, suture, bead, microsphere, or microfibril.

In specific embodiments, the polymers are formulated as barriers, membranes, or films. Alternatively, the polymers are added to barriers, membranes, or films. A barrier, membrane, or film can be supplied in a variety of standard sizes, which can be further cut and sized to the area being treated. Alternatively, the polymer can be formulated as a barrier, membrane, or film made out of strings, microbeads, microspheres, or microfibrils, or the composition can be formulated as a barrier-forming mat. The pharmaceutical compositions comprising Therapeutic Agents and polymers can include a pharmaceutically acceptable carrier, a neutral liquid, neutral gel or neutral solid.

In addition, by varying the ratio of the components in said biodegradable matrices, the surgical handling properties of the cell matrix can be adjusted in a range from a dimensionally stable matrix, to a moldable putty-like consistency to a pliable gel or slurry, to a powder or to an injectable fluid.

In specific embodiments, the polymer is formulated as a gel. The gel can be of varying viscosity. For various embodiments, a gel with a low viscosity is desired. For injectable gels, higher viscosity may be desired if the Therapeutic Agents or compositions thereof are intended to remain in a location of the body rather than dissipate rapidly. Viscosity is the quantity that describes a fluid's resistance to flow measured in centipoise (cP). While the range of viscosity is a continuum. For example, as a frame of reference, not as a limitation of the meaning of viscosity, the viscosity values of about 1-4 cP generally are typified by fluid compositions. Viscosity values of about 5-14 cP generally are typified by gel-like compositions, while viscosity values of 15-20 cP are relatively hard compositions such as plastics. The viscosity of cell cytoplasm is about 11 cP. Viscosity can be measured with, for example, a Saybolt International B.V. (Vlaardingen, The Netherlands). One skilled in the art can also use other measurement techniques and devices common in the art.

In other embodiments, the polymer is formulated as a sponge. When the polymer is a sponge, a predetermined amount of a cell suspension can be transferred on top of a sponge matrix, and the cell suspension can be absorbed. Therapeutic Agents comprising cells expressing IL-15 and IL-15Ra in high amounts can be formulated with polymers which typically comprise a polymer fiber matrix with cells associated throughout the matrix. This allows for greater cell numbers to interact with fibers and the matrix is able to absorb large numbers of cells. In one embodiment, high amounts of IL-15/IL-15Ra complexes refer to amounts of IL-15/IL-15Ra complexes expressed by cells that are at least 1 fold, 2 fold, 3 fold, 4 fold, 5 fold, 6 fold, 7 fold, 8 fold, 9 fold, 10 fold, 20 fold, or more than 20 fold higher than amounts of IL-15/IL-15Ra complexes expressed endogenously by control cells (e.g., cells that have not been genetically engineered to recombinantly express IL-15, IL-15Ra, or both IL-15 and IL-15Ra, or cells comprising an empty vector).

In certain embodiments, the polymer is formulated as a membrane. The membranes may be porous or relatively continuous. In some embodiments the membranes are made of woven polymer fibers that have been combined with Therapeutic Agents comprising cells expressing IL-15 and IL-15Ra. In specific embodiments, Such membranes are particularly useful for delivery on the surface of the skin, surface of internal organs, or surface of lining of body cavities.

In some embodiments, Therapeutic Agents comprising cells recombinantly expressing IL-15, and another therapeutic agent (e.g., a cytokine, e.g., IL-12 or IL-15, or a soluble receptor, e.g., soluble IL-15Ra) are formulated with a polymer, e.g., a polymer described in Section 5.2, supra. In some embodiments, Therapeutic Agents comprising cells recombinantly expressing IL-15Ra, and another therapeutic agent (e.g., a cytokine, e.g., IL-12 or IL-15) are formulated with a polymer, e.g., a polymer described in Section 5.2, supra. In some embodiments, Therapeutic Agents comprising cells recombinantly expressing (i) IL-15, or IL-15Ra, or IL-15 and IL-15Ra, and (ii) another therapeutic polypeptide (e.g., a cytokine, e.g., IL-12, IL-6, or GM-CSF), are formulated with a polymer, e.g., a polymer described in Section 5.2, supra. In a particular embodiment, the cells are irradiated. In a specific embodiment, the cells are irradiated cancer cells engineered to recombinantly express IL-15, or IL-15Ra, or IL-15 and IL-15Ra.

In certain embodiments, the number of cells is at least about 100, 200, 300, 400, 500, 700, 1,000, 5,000, 10,000, 25,000, 50,000, or 100,000 cells. In specific embodiments, the number of cells is at least about 100, 200, 300, 400, or 500 cells. In other embodiments, the number of cells is at least about 300, 400, 500, 600, 700, 800, 900, 1,000, 2,000, 3,000, 4,000 or 5,000 cells. In yet other specific embodiments, the number of cells is at least about 700, 1,000, 5,000, 10,000, 15,000, or 20,000 cells. In some embodiments, the number of cells is at least about 5,000, 10,000, 25,000, 50,000, 75,000 or 100,000 cells. In yet another embodiment, the number of cells is at least about 50,000, 100,000, 200,000, 300,000, 400,000 or 500,000 cells. In other embodiments, the number of cells is at least about $1 \times 10^6$, $5 \times 10^6$, $1 \times 10^7$, $5 \times 10^7$, $1 \times 10^8$, $5 \times 10^8$ or more cells per mg of polymer fiber. In other embodiments, the number of cells is at least about $1 \times 10^6$, $5 \times 10^6$, or $1 \times 10^7$ or more cells per mg of polymer fiber. In some embodiments, the number of cells is at least $1 \times 10^7$, $5 \times 10^7$, $1 \times 10^8$ or more cells per mg of polymer fiber. In other embodiments, the number of cells is at least $5 \times 10^7$, $1 \times 10^8$, $5 \times 10^8$ or more cells per mg of polymer fiber. In some embodiments, the number of cells is less than $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, or $5 \times 10^8$ cells.

5.3.2. Formulations without Polymers

Pharmaceutical compositions for use in accordance with the present invention may be formulated in any conventional manner using one or more pharmaceutically acceptable carriers or excipients.

Generally, the components of the pharmaceutical compositions comprising Therapeutic Agents are supplied either separately or mixed together in unit dosage form, for example, as a dry lyophilized powder or water free concentrate in a hermetically sealed container such as an ampoule or sachette indicating the quantity of active agent. Where the Therapeutic Agent is to be administered by infusion, it can be dispensed with an infusion bottle containing sterile pharmaceutical grade water or saline (e.g., PBS). Where the Therapeutic Agent is administered by injection, an ampoule of sterile water for injection or saline can be provided so that the ingredients may be mixed prior to administration.

In some embodiments, Therapeutic Agents may be formulated for administration by any method known to one of skill in the art, including but not limited to, inhalation, insufflation (either through the mouth or the nose), oral, intradermal, transdermal, intraparenteral, intratumoral, and mucosal (such as buccal, vaginal, rectal, sublingual) administration.

In a specific embodiment, the Therapeutic Agents are formulated for local or systemic parenteral administration. In one embodiment, the Therapeutic Agents are formulated in a pharmaceutically compatible solution.

For oral administration, the pharmaceutical compositions comprising Therapeutic Agents that are polypeptides or nucleic acids may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the Therapeutic Agent or compositions thereof. For buccal administration the compositions may take the form of tablets or lozenges formulated in conventional manner.

For administration by inhalation, the Therapeutic Agents are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The Therapeutic Agents can be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The Therapeutic Agents may also be formulated in rectal compositions such as suppositories or retention enemas, e.g., containing conventional suppository bases such as cocoa butter or other glycerides.

In addition to the formulations described previously, the Therapeutic Agents may also be formulated for implantation (for example subcutaneously or intramuscularly) or by intramuscular injection.

In a specific embodiment, the formulation and administration of various chemotherapeutic, biological/immunotherapeutic and hormonal therapeutic agents for use in combination with Therapeutic Agents are known in the art and described in the *Physician's Desk Reference*, 61$^{st}$ ed (2007). In some embodiments, the Therapeutic Agents are formulated with other therapies, such as those described in Section 5.4 below. In some embodiments, Therapeutic Agents comprising cells recombinantly expressing IL-15, or IL-15Ra, or IL-15 and IL-15Ra are formulated as pharmaceutical compositions. In some embodiments, Therapeutic Agents comprising irradiated cancer cells recombinantly expressing IL-15, or IL-15Ra, or IL-15 and IL-15Ra are formulated as pharmaceutical compositions. In some embodiments, Therapeutic Agents comprising cells recombinantly expressing (i) IL-15, or IL-15Ra, or IL-15 and IL-15Ra; and (ii) another therapeutic polypeptide (e.g., a cytokine, e.g., IL-12, IL-6, or GM-CSF), are formulated as pharmaceutical compositions. In some embodiments, Therapeutic Agents comprising irradiated cancer cells recombinantly expressing (i) IL-15, or IL-15Ra, or IL-15 and IL-15Ra; and (ii) another therapeutic polypeptide (e.g., a cytokine, e.g., IL-12, IL-6, or GM-CSF), are formulated as pharmaceutical compositions. In some embodiments, a combination of (i) Therapeutic Agents that are cells recombinantly expressing IL-15, or IL-15Ra, or IL-15 and IL-15Ra; and (ii) one or more other therapies, e.g., a cytokine (e.g., IL-12, IL-6, GM-CSF); are formulated as pharmaceutical compositions. In some embodiments, a combination of (i) Therapeutic Agents that are irradiated cancer cells recombinantly expressing IL-15, or IL-15Ra, or IL-15 and IL-15Ra; and (ii) one or more other therapies, e.g., a cytokine (e.g., IL-12, IL-6, GM-CSF); are formulated as pharmaceutical compositions.

5.4. Prophylactic/Therapeutic Methods 5.4.1. Enhancing Immune Function

The invention provides methods for enhancing IL-15 mediated immune function in a subject, comprising administering an Agonistic Therapeutic Agent or a composition comprising an Agonistic Therapeutic Agent to a subject in need thereof. In a specific embodiment, the invention provides methods for preventing, treating, and/or managing diseases in which it is desirable to enhance immune function, comprising administering an Agonistic Therapeutic Agent or a composition comprising an Agonistic Therapeutic Agent to a subject in need thereof. In specific embodiments, the Agonistic Therapeutic Agents are formulated with polymers described in Section 5.2, supra. In other specific embodiments, the method comprises combination therapy, wherein the Agonistic Therapeutic Agent is administered to a subject in combination with another therapy, such as those described below, to enhance IL-15 mediated immune function. In a particular embodiment, the Agonistic Therapeutic Agent is administered in combination with a vaccine composition to induce or enhance the immune response elicited by the vaccine composition. Non-limiting examples of diseases that can be prevented, treated, or managed by an enhancement of immune function include, but are not limited to, cancer and infectious diseases. Various cancers and infectious diseases are described below. In a specific embodiment, an Agonistic Therapeutic Agent described herein can be used to treat or manage a condition associated with cancer or a condition resulting from the administration of an anti-cancer therapy (such as, e.g., chemotherapy or radiation). In another embodiment, an Agonistic Therapeutic Agent is administered to a patient diagnosed with cancer to increase the proliferation and/or effector function of one or more immune cell populations in the patient.

In a specific embodiment, an Agonistic Therapeutic Agent enhances or induces immune function in a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the immune function in a subject not administered the Agonistic Therapeutic Agent using assays well known in the art, e.g., ELISPOT, ELISA, and cell proliferation assays. In a specific embodiment, the immune function is cytokine release (e.g., interferon-gamma, IL-2, IL-5, IL-10, IL-12, or transforming growth factor (TGF)-beta). In one embodiment, the IL-15 mediated immune function is NK cell proliferation, which can be assayed, e.g., by flow cytometry to detect the number of cells expressing markers of NK cells (e.g., CD56). In another embodiment, the IL-15 mediated immune function is antibody production, which can be assayed, e.g., by ELISA. In some embodiments, the IL-15 mediated immune function is effector function, which can be assayed, e.g., by a cytotoxicity assay or other assays well known in the art.

In specific embodiments, non-limiting examples of immune function enhanced by the Agonistic Therapeutic Agent are proliferation/expansion of lymphocytes (e.g., increase in the number of lymphocytes), inhibition of apoptosis of lymphocytes, activation of dendritic cells (or antigen presenting cells), and antigen presentation. In particular embodiments, an immune function enhanced by the Agonistic Therapeutic Agent is proliferation/expansion in the number of or activation of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, dendritic cells (immature or mature), antigen presenting cells, macrophages, mast cells, natural killer T cells (NKT cells), tumor-resident T cells, CD122$^+$ T cells, or natural killer cells (NK cells). In one embodiment, the Agonistic Therapeutic Agent enhances the proliferation/expansion or number of lymphocyte progenitors. In some embodiments, an Agonistic Therapeutic Agent increases the number of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, dendritic cells (immature or mature), antigen presenting cells, macrophages, mast cells, natural killer T cells (NKT cells), tumor-resident T cells, CD12$^+$ T cells, or natural killer cells (NK cells) by approximately 1 fold, 2 fold, 3 fold, 4 fold, S fold, 6 fold, 7 fold, 8 fold, 9 fold, 10 fold, 20 fold, or more relative a negative control (e.g., number of the respective cells not treated, cultured, or contacted with an Agonistic Therapeutic Agent).

5.4.1.1. Cancer

The invention provides a method for preventing, treating, and/or managing cancer, comprising administering an effective amount of an Agonistic Therapeutic Agent or a composition comprising an Agonistic Therapeutic Agent to a subject in need thereof. In specific embodiments, the Agonistic Therapeutic Agents are formulated with polymers described in Section 5.2, supra.

The effect of an Agonistic Therapeutic Agent on proliferation of cancer cells can be detected by routine assays, such as by assays that measure the uptake of radiolabeled thymidine. Alternatively, cell viability can be measured by assays that measure lactate dehydrogenase (LDH), a stable cytosolic enzyme that is released upon cell lysis, or by the release of [$^{51}$Cr] upon cell lysis. In one embodiment, necrosis measured by the ability or inability of a cell to take up a dye such as neutral red, trypan blue, or ALAMAR™ blue (Page et al., 1993, Intl. J. of Oncology 3:473 476). In such an assay, the cells are incubated in media containing the dye, the cells are washed, and the remaining dye, reflecting cellular uptake of the dye, is measured spectrophotometrically.

In another embodiment, the dye is sulforhodamine B (SRB), whose binding to proteins can be used as a measure of cytotoxicity (Skehan et al., 1990, J. Nat'l Cancer Inst. 82:1107 12). In yet another embodiment, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55 63).

In other embodiments, apoptotic cells are measured in both the attached and "floating" compartments of the cultures. Both compartments are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature (see, e.g., Piazza et al., 1995, Cancer Research 55:3110 16). Features of this method include collecting both floating and attached cells, identification of the optimal treatment times and dose range for observing apoptosis, and identification of optimal cell culture conditions.

In another embodiment, apoptosis is quantitated by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34 37 (Roche Molecular Biochemicals).

In yet another embodiment, apoptosis can be observed morphologically.

Cancer cell lines on which such assays can be performed are well known to those of skill in the art. Apoptosis, necrosis and proliferation assays can also be performed on primary cells, e.g., a tissue explant.

In a specific embodiment, the proliferation or viability of cancer cells contacted with an Agonistic Therapeutic Agent or a composition comprising an Agonistic Therapeutic Agent is inhibited or reduced by at least 2 fold, preferably at least 2.5 fold, at least 3 fold, at least 4 fold, at least 5 fold, at least 7 fold, or at least 10 fold relative to the proliferation of the cancer cells when contacted with a negative control as measured using assays well known in the art, e.g., cell proliferation assays using CSFE, BrdU, and $^3$H-Thymidine incorporation. In another embodiment, the proliferation of cancer cells contacted with an Agonistic Therapeutic Agent or a composition comprising an Agonistic Therapeutic Agent is inhibited or reduced by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to cancer cells contacted with a negative control as measured using assays well known in the art, e.g., cell proliferation assays using CSFE, BrdU, and $^3$H-Thymidine incorporation, or those assays described above. In one aspect, the composition comprising an Agonistic Therapeutic Agent further comprises cells (e.g., NK cells or cytotoxic T cells) that are responsive to IL-15 signaling and that can target and exert cytotoxic effects on the cancer cells.

In a specific embodiment, the administration of an Agonistic Therapeutic Agent or a composition comprising an Agonistic Therapeutic Agent to a subject with cancer (in some embodiments, an animal model for cancer) inhibits or reduces the growth of a tumor by at least 2 fold, preferably at least 2.5 fold, at least 3 fold, at least 4 fold, at least 5 fold, at least 7 fold, or at least 10 fold relative to the growth of a tumor in a subject with cancer (in some embodiments, in the same animal model for cancer) administered a negative control as measured using assays well known in the art. In another embodiment, the administration of an Agonistic Therapeutic Agent or a composition comprising an Agonistic Therapeutic Agent to a subject with cancer (in some embodiments, an animal model for cancer) inhibits or reduces the growth of a tumor by at least 25%, at least 30%, at least 35%, at least 40%, at least 45%, at least 50%, at least 55%, at least 60%, at least 65%, at least 70%, at least 75%, at least 80%/o, at least 85%, at least 90%, or at least 95% relative to the growth of a tumor in a subject with cancer (in some embodiments, in the same animal model for cancer) administered a negative control as measured using assays well known in the art.

In a specific embodiment, the administration of an Agonistic Therapeutic Agent or a composition comprising an Agonistic Therapeutic Agent to a subject with cancer (in some embodiments, an animal model for cancer) reduces the size of a tumor by at least 2 fold, preferably at least 2.5 fold, at least 3 fold, at least 4 fold, at least 5 fold, at least 7 fold, or at least 10 fold relative to the growth of a tumor in a subject with cancer (in some embodiments, the same animal model for cancer) administered a negative control as measured using assays well known in the art. In another embodiment, the administration of an Agonistic Therapeutic Agent or a composition comprising an Agonistic Therapeutic Agent to a subject with (in some embodiments, an animal model for cancer) reduces the size of a tumor by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to the growth of a tumor in a subject with cancer (in some embodiments, the same animal model for cancer) administered a negative control as measured using assays well known in the art. In a specific embodiment, the cancer is melanoma, renal cancer, colon cancer, or prostate cancer.

In addition, an Agonistic Therapeutic Agent that is useful in the treatment or management of cancer is an irradiated tumor (or cancer) cell or irradiated tumor (or cancer) cell line that recombinantly expresses IL-15/IL-15Ra complexes. Such Agonistic Therapeutic Agents can be prepared by a method that comprises transducing or transfecting primary tumor dells or tumor cell lines with expression constructs for IL-15 and IL-15Ra, and following expression of the IL-15 and IL-15Ra proteins, irradiating the tumor cells. In one embodiment, the form of irradiation is γ-radiation. IL-15 and IL-15Ra can be expressed from the same construct or different constructs, and under the control of the same promoter or different promoters. The IL-15 and IL-15Ra expression construct(s) can be introduced into tumor (or cancer) cells by any means known to those of skill in the art, such as using a viral vector or mammalian expression vector. Alternatively, the native IL-15 and native IL-15Ra of the tumor (or cancer) cells may be activated using gene activation methods. Subsequently, the irradiated tumor (or cancer) cells recombinantly expressing IL-15/IL-15Ra complexes are administered into a cancer patient to induce and/or enhance an immune response to the cancer cells or to cancer antigens of the cancer cells. In a specific embodiment, the induced or enhanced immune response is increased production of antibodies to the cancer cells or to the cancer antigens of the cancer cells in the cancer patient. In another embodiment, the induced or enhanced immune response is an increase in effector cell function, e.g., antibody-dependent cellular cytotoxicity (ADCC) against cancer cells in the patient. In some embodiments, the induced or enhanced immune response is increase in lymphocyte number, lymphocyte proliferation, and/or lymphocyte activity.

An Agonistic Therapeutic Agent can be administered in combination with one or more other therapies, e.g., anti-cancer agents, cytokines or anti-hormonal agents, to treat and/or manage cancer. Non-limiting examples anti-cancer agents are described in Section 5.4.5.1 below. In one embodiment, the combination of an Agonistic Therapeutic Agent and one or more other therapies provides an additive therapeutic effect relative to the therapeutic effects of the Agonistic Therapeutic Agent alone or the one or more other therapies alone. In one embodiment, the combination of an Agonistic Therapeutic Agent and one or more other therapies provides more than an additive therapeutic effect relative to the therapeutic effects of the Agonistic Therapeutic Agent alone or the one or more other therapies alone. In one embodiment, the combination of an Agonistic Therapeutic Agent and one or more other therapies provides a synergistic therapeutic effect relative to the therapeutic effects of the Agonistic Therapeutic Agent alone or the one or more other therapies alone.

In one embodiment, the one or more therapies include, but are not limited to cytokines/growth factors, e.g., interleukin (IL) 1, IL-2, IL-3, IL-4, IL-5, IL-6, IL-7, IL-8, IL-10, IL-11, IL-12, IL-15, TNF-α, TNF-β, TGF-β, GM-CSF, and interferon-γ. In one embodiment, the one or more therapies include, but are not limited to receptors, antibodies, or other binding agents that bind to cytokines/growth factors, e.g., interleukin (IL) 1, IL-2, IL-3, IL-4, IL-5, IL-6, IL-7, IL-8, IL-10, IL-11, IL-12, TNF-α, TNF-β, TGF-β, GM-CSF, interferon-α, interferon-β, and interferon-γ. In some embodiments, the one or more therapies include, but are not limited to, cells recombinantly expressing a therapeutic protein (or polypepides), e.g., a cytokine, a growth factor, a chemokine, or a fragment or derivative thereof. In a particular embodiment, the one or more therapies include, but are not limited to, cells recombinantly expressing IL-12, IL-6, GM-CSF, interferon-α, interferon-β, interferon-γ or TNF-α. In one embodiment, the one or more therapies are not cells recombinantly expressing IL-12. In one embodiment, the one or more therapies are not cells recombinantly expressing IL-6. In one embodiment, the one or more therapies are not cells recombinantly expressing GM-CSF. In one embodiment, the one or more therapies are not cells recombinantly expressing TNF-α. In a specific embodiment, the cells recombinantly expressing a therapeutic protein (polypeptide) are cancer cells. In a specific embodiment, the cells recombinantly expressing a therapeutic protein (polypeptide) are irradiated cancer cells. In a specific embodiment, the cells recombinantly expressing a therapeutic protein (polypeptide) are irradiated cancer cells obtained from a patient. In one embodiment, the cells recombinantly express one or more therapeutic proteins (polypeptides). In one embodiment, the present invention provides for a combination of an Agonistic Therapeutic Agent and one or more other therapies, wherein the Agonistic Therapeutic Agent comprises cells recombinantly express IL-15 and IL-15Ra, and wherein the one or more other therapies comprise one or more exogenous cytokines (e.g., IL-12, IL-6, GM-CSF, interferon-α, interferon-β, interferon-γ or TNF-α). In one embodiment, the present invention provides for a combination of an Agonistic Therapeutic Agent and one or more other therapies, wherein the Agonistic Therapeutic Agent comprises cells recombinantly express IL-15 and IL-15Ra, and wherein the one or more other therapies comprise (i) exogenous IL-15 polypeptide or exogenous IL-15Ra polypeptide, and (ii) one or more other exogenous cytokines (e.g., IL-12, IL-6, GM-CSF, interferon-α, interferon-β, interferon- or TNF-α). In one embodiment, an Agonistic Therapeutic Agent comprises cells engineered to recombinantly express (i) IL-15, IL-15Ra, or IL-15 and IL-15Ra; and (ii) one or more cytokines/growth factors.

An Agonistic Therapeutic Agent can also be administered in combination with radiation therapy comprising, e.g., the use of x-rays, gamma rays and other sources of radiation to destroy the cancer cells. In specific embodiments, the radiation treatment is administered as external beam radiation or teletherapy wherein the radiation is directed from a remote source. In other embodiments, the radiation treatment is administered as internal therapy or brachytherapy wherein a radioactive source is placed inside the body close to cancer cells or a tumor mass. In one aspect, the Agonistic Therapeutic Agent can enhance the immune function of cancer patient with a compromised immune system due to anti-cancer therapy. An Agonistic Therapeutic Agent can also be administered in combination with chemotherapy. In one embodiment, an Agonistic Therapeutic Agent can be used before, during or after radiation therapy or chemotherapy. In one embodiment, an Agonistic Therapeutic Agent can be used before, during or after surgery. In one embodiment, the present invention provides for a combination of transplant and an Agonistic Therapeutic Agent.

Non-limiting examples of anti-hormonal agents are anti-hormonal agents that act to regulate or inhibit hormone action on tumors, such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® V exemestane, formestanie, fadrozole, RIVISOR® vorozole, FEMARA® letrozole, and ARIMIDEX® D anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELX® rmRH; Vinorelbine and Esperamicins (see U.S. Pat. No. 4,675,187), and pharmaceutically acceptable salts, acids or derivatives of any of the above.

Cancers and related disorders that can be prevented, treated, or managed in accordance with the methods described herein include, but are not limited to, the following: Leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, and chronic lymphocytic leukemia, hairy cell leukemia; polycythemia vera; lymphomas such as but not limited to Hodgkin's disease, and non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including but not limited to, ocular melanoma such as iris melanoma, choroidal melanoma, and cilliary body melanoma, and retinoblastoma; vaginal cancers, including but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including but not limited to, squamous cell carcinoma, and adenocarcinoma; uterine cancers including but not limited to, endometrial carcinoma and uterine sarcoma; ovarian cancers including but not limited to, ovarian epithelial carcinoma, borderline tumor, germ cell tumor, and stromal tumor; esophageal cancers including but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including but not limited to hepatocellular carcinoma and hepatoblastoma; gallbladder cancers including but not limited to, adenocarcinoma; cholangiocarcinomas including but not limited to, pappillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including but not limited to, germinal tumor, seminoma, anaplaslic, spermatocytic, nonseminoma, embryonal carcinoma, teratoma carcinoma, choriocarcinoma (yolk-sac tumor); prostate cancers including but not limited to, adenocarcinoma, leiomyosarcoma, and rhabdomyosarcoma; penal cancers; oral cancers including but not limited to, squamous cell carcinoma; basal cancers; salivary gland cancers including but not limited to, adenocarcinoma, mucoepidermoid carcinoma, and adenoidcystic carcinoma; pharynx cancers including but not limited to, squamous cell cancer, and verrucous; skin cancers including but not limited to, basal cell carcinoma, squamous cell carcinoma and melanoma, and superficial spreading melanoma, nodular melanoma, lentigo malignant melanoma, acral lentiginous melanoma; kidney cancers including but not limited to, renal cell cancer, renal cancer, adenocarcinoma, hypernephroma, fibrosarcoma, and transitional cell cancer (renal pelvis and/or uterer); Wilms' tumor; bladder cancers including but not limited to, transitional cell carcinoma, squamous cell cancer, adenocarcinoma, and carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In one embodiment, the cancer is benign, e.g., polyps and benign lesions. In other embodiments, the cancer is metastatic. The Agonistic Therapeutic Agents can be used in the treatment of pre-malignant as well as malignant conditions. Pre-malignant conditions include hyperplasia, metaplasia, and dysplasia. Treatment of malignant conditions includes the treatment of primary as well as metastatic tumors. In a specific embodiment the cancer is melanoma, colon cancer, and lung cancer.

In some embodiments, Agonistic Therapeutic Agents, compositions comprising Agonistic Therapeutic Agents, or combination therapies are administered to a subject suffering from or diagnosed with cancer. In other embodiments, Agonistic Therapeutic Agents, compositions comprising Agonistic Therapeutic Agents, or combination therapies are administered to a subject predisposed or susceptible to developing cancer. In some embodiments, Agonistic Therapeutic Agents, compositions comprising Agonistic Therapeutic Agents, or combination therapies are administered to a subject that lives in a region where there is a high occurrence rate of cancer. In a specific embodiment, the cancer is characterized by a pre-malignant tumor or a malignant tumor.

In certain embodiments, an Agonistic Therapeutic Agent, composition comprising an Agonistic Therapeutic Agent, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, an Agonistic Therapeutic Agent, composition comprising an Agonistic Therapeutic Agent, or a combination therapy is administered to a human at risk developing cancer. In certain embodiments, an Agonistic Therapeutic Agent, composition comprising an Agonistic Therapeutic Agent, or a combination therapy is administered to a human with cancer. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, an Agonistic Therapeutic Agent, composition comprising an Agonistic Therapeutic Agent, or a combination therapy is administered to a human infant or a premature human infant. In other embodiments, an Agonistic Therapeutic Agent, composition comprising an Agonistic Therapeutic Agent, or a combination therapy is administered to a human child. In other embodiments, an Agonistic Therapeutic Agent, composition comprising an Agonistic Therapeutic Agent, or a combination therapy is administered to a human adult in yet other embodiments, an Agonistic Therapeutic Agent, composition comprising an Agonistic Therapeutic Agent, or a combination therapy is administered to an elderly human.

In certain embodiments, an Agonistic Therapeutic Agent, composition comprising an Agonistic Therapeutic Agent, or a combination therapy is administered to a pet, e.g., a dog or cat. In certain embodiments, an Agonistic Therapeutic Agent, composition comprising an Agonistic Therapeutic Agent, or a combination therapy is administered to a farm animal or livestock, e.g., pig, cows, horses, chickens, etc.

In certain embodiments, an Agonistic Therapeutic Agent, composition comprising an Agonistic Therapeutic Agent, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, an Agonistic Therapeutic Agent, composition comprising an Agonistic Therapeutic Agent, or a combination therapy is administered to a subject receiving or recovering from immunosuppressive therapy. In certain embodiments, an Agonistic Therapeutic Agent, composition comprising an Agonistic Therapeutic Agent, or a combination therapy is administered to a subject that has or is at risk of getting AIDS, a viral infection, or a bacterial infection. In certain embodiments, a subject that is, will or has undergone surgery, chemotherapy and/or radiation therapy. In some embodiments, an Agonistic Therapeutic Agent, composition comprising an Agonistic Therapeutic Agent, or a combination therapy is administered to a subject that lives in a nursing home, a group home (i.e., a home for 10 or more subjects), or a prison.

In some embodiments, a patient is administered an Agonistic Therapeutic Agent, composition comprising an Agonistic Therapeutic Agent, or a combination therapy is before any adverse effects or intolerance to therapies other than Agonistic Therapeutic Agents develops. In some embodiments, Agonistic Therapeutic Agents, compositions comprising Agonistic Therapeutic Agents, or combination therapies are administered to refractory patients. In a certain embodiment, refractory patient is a patient refractory to a standard anti-cancer therapy. In certain embodiments, a patient with cancer, is refractory to a therapy when the cancer has not significantly been eradicated and/or the symptoms have not been significantly alleviated. The determination of whether a patient is refractory can be made either in vive or in vitro by any method known in the art for assaying the effectiveness of a treatment, using art-accepted meanings of "refractory" in such a context. In various embodiments, a patient with cancer is refractory when a cancerous tumor has not decreased or has increased.

In some embodiments, Agonistic Therapeutic Agents, compositions comprising Agonistic Therapeutic Agents, or combination therapies are administered to a patient to prevent the onset or reoccurrence of cancer in a patient at risk of developing such cancer. In some embodiments, Agonistic Therapeutic Agents, compositions comprising Agonistic Therapeutic Agents, or combination therapies are administered to a patient who are susceptible to adverse reactions to conventional therapies.

In some embodiments, one or more Agonistic Therapeutic Agents, compositions comprising Agonistic Therapeutic Agents, or combination therapies are administered to a patient who has proven refractory to therapies other than Agonistic Therapeutic Agents, but are no longer on these therapies. In certain embodiments, the patients being managed or treated in accordance with the methods described herein are patients already being treated with antibiotics, anti-cancer agents, or other biological therapy/immunotherapy. Among these patients are refractory patients, patients who are too young for conventional therapies, and patients with reoccurring viral infections despite management or treatment with existing therapies.

In some embodiments, the subject being administered one or more Agonistic Therapeutic Agents, compositions comprising Agonistic Therapeutic Agents, or combination therapies has not received a therapy prior to the administration of the Agonistic Therapeutic Agents, compositions comprising Agonistic Therapeutic Agents, or combination therapies. In other embodiments, one or more Agonistic Therapeutic Agents, compositions comprising Agonistic Therapeutic Agents, or combination therapies are administered to a subject who has received a therapy prior to administration of one or more Agonistic Therapeutic Agents, compositions comprising Agonistic Therapeutic Agents, or combination therapies. In some embodiments, the subject administered an Agonistic Therapeutic Agent or a composition comprising an Agonistic Therapeutic Agent was refractory to a prior therapy or experienced adverse side effects to the prior therapy or the prior therapy was discontinued due to unacceptable levels of toxicity to the subject.

5.4.1.2. Infectious Diseases

The invention provides a method for treating, preventing and/or managing an infectious disease in a subject, comprising administering an effective amount of an Agonistic Therapeutic Agent or a composition comprising an Agonistic Therapeutic Agent to a subject in need thereof.

In a particular embodiment, the Agonistic Therapeutic Agents are cells infected with a pathogen, wherein the cells are engineered to express IL-15 and IL-15Ra as described in Section 5.1.1, are irradiated, and are administered to a patient to induce and/or enhance an immune response to the infected cells or to antigens of the pathogen. In one embodiment, the pathogen is an intracellular pathogen, e.g., intracellular bacteria or virus. In a specific embodiment, the induced or enhanced immune response is increased production in the patient of antibodies to the infected cells or to the antigens of the pathogen. In one embodiment, the form of irradiation is γ-radiation. IL-15 and IL-15Ra can be expressed from the same construct or different constructs, and under the control of the same promoter or different promoters. The IL-15 and IL-15Ra expression construct(s) can be introduced into cells infected with a pathogen by any means known to those of skill in the art, such as using a viral vector or mammalian expression vector. Alternatively, the native IL-15 and native IL-15Ra of the cells infected with a pathogen may be activated using gene activation methods. Subsequently, the irradiated cells infected with a pathogen recombinantly expressing IL-15/IL-15Ra complexes are administered into a subject to induce and/or enhance an immune response to the pathogen or to antigens of the pathogen. In a specific embodiment, the induced or enhanced immune response is increased production of antibodies to the pathogen. In another embodiment, the induced or enhanced immune response is an increase in effector cell function, e.g., antibody-dependent cellular cytotoxicity (ADCC) against the pathogen and/or cells infected with a pathogen in the patient. In some embodiments, the induced or enhanced immune response is increase in lymphocyte number, lymphocyte proliferation, and/or lymphocyte activity. In another embodiment, the induced or enhanced immune response is an increase in effector cell function, e.g., cytotoxic cells or antibody-dependent cellular cytotoxicity (ADCC) against the infected cells in the patient.

In other embodiments, an Agonistic Therapeutic Agent can be administered in combination with one or more other therapies. Non-limiting examples of other therapies that can be used in combination with Agonistic Therapeutic Agents are described in Sections 5.4.5.2 and 5.4.5.3. In one embodiment, the combination of an Agonistic Therapeutic Agent and one or more other therapies provides an additive therapeutic effect relative to the therapeutic effects of the Agonistic Therapeutic Agent alone or the one or more other therapies alone. In one embodiment, the combination of an Agonistic Therapeutic Agent and one or more other therapies provides more than an additive therapeutic effect relative to the therapeutic effects of the Agonistic Therapeutic Agent alone or the one or more other therapies alone. In one embodiment, the combination of an Agonistic Therapeutic Agent and one or more other therapies provides a synergistic therapeutic effect relative to the therapeutic effects of the Agonistic Therapeutic Agent alone or the one or more other therapies alone.

In one embodiment, the one or more therapies include, but are not limited to cytokines/growth factors, e.g., interleukin (IL) 1, IL-2, IL-3, IL-4, IL-5, IL-6, IL-7, IL-8, IL-10, IL-11, IL-12, IL-15, TNF-$\alpha$, TNF-$\beta$, TGF-$\beta$, GM-CSF, and interferon-$\gamma$. In one embodiment, the one or more therapies include, but are not limited to receptors, antibodies, or other binding agents that bind to cytokines/growth factors, e.g., interleukin (IL) 1, IL-2, IL-3, IL-4, IL-5, IL-6, IL-7, IL-8, IL-10, IL-11, IL-12, TNF-$\alpha$, TNF-$\beta$, TGF-$\beta$, GM-CSF, interferon-$\alpha$, interferon-$\beta$, and interferon-$\gamma$. In some embodiments, the one or more therapies include, but are not limited to, cells recombinantly expressing a therapeutic protein (or polypeptides), e.g., a cytokine, a growth factor, a chemokine, or a fragment or derivative thereof. In a particular embodiment, the one or more therapies include, but are not limited to, cells recombinantly expressing IL-12, IL-6, GM-CSF, interferon-$\alpha$, interferon-$\beta$, interferon-$\gamma$ or TNF-$\alpha$. In one embodiment, the one or more therapies are not cells recombinantly expressing IL-12. In one embodiment, the one or more therapies are not cells recombinantly expressing IL-6. In one embodiment, the one or more therapies are not cells recombinantly expressing GM-CSF. In one embodiment, the one or more therapies are not cells recombinantly expressing TNF-$\alpha$. In a specific embodiment, the cells recombinantly expressing a therapeutic protein (polypeptide) are cells infected with a pathogen or infectious agent. In a specific embodiment, the cells recombinantly expressing a therapeutic protein (polypeptide) are irradiated cells infected with a pathogen or infectious agent. In a specific embodiment, the cells recombinantly expressing a therapeutic protein (polypeptide) are irradiated cells infected with a pathogen or infectious agent obtained from a patient. In one embodiment, the cells recombinantly express one or more therapeutic proteins (polypeptides). In one embodiment, the present invention provides for a combination of an Agonistic Therapeutic Agent and one or more other therapies, wherein the Agonistic Therapeutic Agent comprises cells recombinantly express IL-15 and IL-15Ra, and wherein the one or more other therapies comprise one or more exogenous cytokines (e.g., IL-12, IL-6, GM-CSF, interferon-$\alpha$, interferon-b, interferon-$\gamma$ or TNF-$\alpha$). In one embodiment, the present invention provides for a combination of an Agonistic Therapeutic Agent and one or more other therapies, wherein the Agonistic Therapeutic Agent comprises cells recombinantly express IL-15 and EL-15Ra, and wherein the one or more other therapies comprise (i) exogenous IL-15 polypeptide or exogenous IL-15Ra polypeptide, and (ii) one or more other exogenous cytokines (e.g., IL-12, IL-6, GM-CSF, interferon-$\alpha$, interferon-$\alpha$, interferon-$\gamma$ or TNF-$\alpha$). In one embodiment, an Agonistic Therapeutic Agent comprises cells engineered to recombinantly express (i) IL-15, IL-15Ra, or IL-15 and IL-15Ra; and (ii) one or more cytokines/growth factors.

Infectious diseases that can be treated, prevented, and/or managed by Agonistic Therapeutic Agents are caused by infectious agents including but not limited to bacteria, fungi, protozae, and viruses.

Viral diseases that can be prevented, treated and/or managed in accordance with the methods described herein include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovicus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral miningitis, encephalitis, dengue or small pox.

Bacterial diseases caused by bacteria (e.g., *Escherichia coli, Klebsiella pneumnoniae, Staphylococcus aureus, Enterococcus faecials, Candida albicans, Proteus vulgaris, Staphylococcus viridans*, and *Pseudomonas aeruginosa*) that can be prevented, treated and/or managed in accordance with the methods described herein include, but are not limited to, mycobacteria *rickettsia, mycoplasma, neisseria, S. pneumonia, Borrelia burgdorferi* (Lyme disease), *Bacillus antracis* (anthrax), *tetanus, streptococcus, staphylococcus, mycobacterium, pertissus, cholera, plague, diptheria, chlamydia, S. aureus* and *legionella*.

Protozoal diseases caused by protozoa that can be prevented, treated and/or managed in accordance with the methods described herein include, but are not limited to, *leishmania, kokzidioa, trypanosoma* or malaria.

Parasitic diseases caused by parasites that can be prevented, treated and/or managed in accordance with the methods described herein include, but are not limited to, *chlamydia* and *rickettsia*.

In certain embodiments, administering an Agonistic Therapeutic Agent or a composition comprising an Agonistic Therapeutic Agent to a subject (in some embodiments, an animal model) infected with an infectious agent inhibits or reduces replication of the infectious agent by at least 20% to 25%, preferably at least 25% to 30%, at least 30% to 35%, at least 35% to 40%, at least 40° % to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, administering an Agonistic Therapeutic Agent or a composition comprising an Agonistic Therapeutic Agent to a subject (in some embodiments, an animal model) infected with an infectious agent inhibits or reduces replication of the infectious agent by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, administering an Agonistic Therapeutic Agent or a composition comprising an Agonistic Therapeutic Agent to a subject (in some embodiments, an animal model) infected with an infectious agent inhibits or reduces replication of the infectious agent by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, administering an Agonistic Therapeutic Agent or a composition comprising an Agonistic Therapeutic Agent to a subject (in some embodiments, an animal model) infected with an infectious agent reduces the titer of the infectious agent by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, administering an Agonistic Therapeutic Agent or a composition comprising an Agonistic Therapeutic Agent to a subject (in some embodiments, an animal model) infected with an infectious agent reduces the titer of the infectious agent by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, administering an Agonistic Therapeutic Agent or a composition comprising an Agonistic Therapeutic Agent to a subject (in some embodiments, an animal model) infected with an infectious agent reduces the titer of the infectious agent by 1 log, 1.5 logs, 2 logs, 2.5 logs, 3 logs, 3.5 logs, 4 logs, 5 logs or more relative to a negative control as determined using an assay described herein or others known to one of skill in the art.

In some embodiments, Agonistic Therapeutic Agents, compositions comprising Agonistic Therapeutic Agents, or combination therapies are administered to a subject suffering from an infectious disease caused by infectious agents including, but not limited to bacteria, fungi, protozae, and viruses. In other embodiments, Agonistic Therapeutic Agents, compositions comprising Agonistic Therapeutic Agents, or combination therapies are administered to a subject predisposed or susceptible to an infectious disease. In some embodiments, Agonistic Therapeutic Agents, compositions comprising Agonistic Therapeutic Agents, or combination therapies are administered to a subject that lives in a region where there has been or might be an outbreak with infections by infectious agents. In some embodiments, the infection is a latent infection. In other embodiments, the infection by the infectious agent is an active infection. In yet other embodiments, the infection by the infectious agent is a chronic viral infection. In a specific embodiment, the infection is a viral infection. In a specific embodiment, the virus infects humans.

In certain embodiments, an Agonistic Therapeutic Agent, composition comprising an Agonistic Therapeutic Agent, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, an Agonistic Therapeutic Agent, composition comprising an Agonistic Therapeutic Agent, or a combination therapy is administered to a human at risk for a virus infection. In certain embodiments, an Agonistic Therapeutic Agent, composition comprising an Agonistic Therapeutic Agent, or a combination therapy is administered to a human with a virus infection. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, an Agonistic Therapeutic Agent, composition comprising an Agonistic Therapeutic Agent, or a combination therapy is administered to a human infant or premature human infant. In other embodiments, an Agonistic Therapeutic Agent, composition comprising an Agonistic Therapeutic Agent, or a combination therapy is administered to a human child. In other embodiments, an Agonistic Therapeutic Agent, composition comprising an Agonistic Therapeutic Agent, or a combination therapy is administered to a human adult. In yet other embodiments, an Agonistic Therapeutic Agent, composition comprising an Agonistic Therapeutic Agent, or a combination therapy is administered to an elderly human.

In certain embodiments, an Agonistic Therapeutic Agent, composition comprising an Agonistic Therapeutic Agent, or a combination therapy is administered to a pet, e.g., a dog or cat. In certain embodiments, an Agonistic Therapeutic Agent, composition comprising an Agonistic Therapeutic Agent, or a combination therapy is administered to a farm animal or livestock, e.g., pig, cows, horses, chickens, etc. In certain embodiments, an Agonistic Therapeutic Agent, composition comprising an Agonistic Therapeutic Agent, or a combination therapy is administered to a bird, e.g., ducks or chicken.

In certain embodiments, an Agonistic Therapeutic Agent, composition comprising an Agonistic Therapeutic Agent, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, an Agonistic Therapeutic Agent, composition comprising an Agonistic Therapeutic Agent, or a combination therapy is administered to a subject receiving or recovering from immunosuppressive therapy. In certain embodiments, an Agonistic Therapeutic Agent, composition comprising an Agonistic Therapeutic Agent, or a combination therapy is administered to a subject that has or is at risk of getting cancer, AIDS, another infection, or a bacterial infection. In certain embodiments, a subject that is, will or has undergone surgery, chemotherapy and/or radiation therapy. In certain embodiments, an Agonistic Therapeutic Agent, composition comprising an Agonistic Therapeutic Agent, or a combination therapy is administered to a subject that has cystic fibrosis, pulmonary fibrosis, or another disease which makes the subject susceptible to an infection. In certain embodiments, an Agonistic Therapeutic Agent, composition comprising an Agonistic Therapeutic Agent, or a combination therapy is administered to a subject that has, will have or had a tissue transplant. In some embodiments, an Agonistic Therapeutic Agent, composition comprising an Agonistic Therapeutic Agent, or a combination therapy is administered to a subject that lives in a nursing home, a group home (i.e., a home for 10 or more subjects), or a prison. In some embodiments, an Agonistic Therapeutic Agent, composition comprising an Agonistic Therapeutic Agent, or a combination therapy is administered to a subject that attends school (e.g., elementary school, middle school, junior high school, high school or university) or daycare. In some embodiments, an Agonistic Therapeutic Agent, composition comprising an Agonistic Therapeutic Agent, or a combination therapy is administered to a subject that works in the healthcare area, such as a doctor or a nurse, or in a hospital. In certain embodiments, an Agonistic Therapeutic Agent, composition comprising an Agonistic Therapeutic Agent, or a combination therapy is administered to a subject that is pregnant or will become pregnant.

In some embodiments, a patient is administered an Agonistic Therapeutic Agent, composition comprising an Agonistic Therapeutic Agent, or a combination therapy before any adverse effects or intolerance to therapies other than Agonistic Therapeutic Agents develops. In some embodiments, Agonistic Therapeutic Agents, compositions comprising Agonistic Therapeutic Agents, or combination therapies are administered to refractory patients. In a certain embodiment, refractory patient is a patient refractory to a standard therapy. In certain embodiments, a patient with an infection, is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with an infection is refractory when replication of the infectious agent has not decreased or has increased.

In some embodiments, Agonistic Therapeutic Agents, compositions comprising Agonistic Therapeutic Agents, or combination therapies are administered to a patient to prevent the onset or reoccurrence of infections (e.g., viral infections) in a patient at risk of developing such infections. In some embodiments, Agonistic Therapeutic Agents, compositions comprising Agonistic Therapeutic Agents, or combination therapies are administered to a patient who are susceptible to adverse reactions to conventional therapies.

In some embodiments, one or more Agonistic Therapeutic Agents, compositions comprising Agonistic Therapeutic Agents, or combination therapies are administered to a patient who has proven refractory to therapies other than Agonistic Therapeutic Agents, but are no longer on these therapies. In certain embodiments, the patients being managed or treated in accordance with the methods of this invention are patients already being treated with antibiotics, anti-vitals, anti-fungals, or other biological therapy/immunotherapy. Among these patients are refractory patients, patients who are too young for conventional therapies, and patients with reoccurring viral infections despite management or treatment with existing therapies.

In some embodiments, the subject being administered one or more Agonistic Therapeutic Agents, compositions comprising Agonistic Therapeutic Agents, or combination therapies has not received a therapy prior to the administration of the Agonistic Therapeutic Agents, compositions comprising Agonistic Therapeutic Agents, or combination therapies. In other embodiments, one or more Agonistic Therapeutic Agents, compositions comprising Agonistic Therapeutic Agents, or combination therapies are administered to a subject who has received a therapy prior to administration of one or more Agonistic Therapeutic Agents or compositions comprising one or more Agonistic Therapeutic Agents, or combination therapies. In some embodiments, the subject administered an Agonistic Therapeutic Agent or a composition comprising an Agonistic Therapeutic Agent was refractory to a prior therapy or experienced adverse side effects to the prior therapy or the prior therapy was discontinued due to unacceptable levels of toxicity to the subject.

5.4.2. Suppressing Immune Function

The invention provides methods for suppressing the IL-15 mediated immune function in a subject, comprising administering an Antagonistic Therapeutic Agent or a composition comprising an Antagonistic Therapeutic Agent to a subject in need thereof. In a specific embodiment, the invention provides methods for preventing, treating, and/or managing diseases in which it is desirable to suppress immune function, comprising administering an Antagonistic Therapeutic Agent or a composition comprising an Antagonistic Therapeutic Agent to a subject in need thereof. In specific embodiments, the Antagonistic Therapeutic Agents are formulated with polymers described in Section 5.2, supra. In other embodiments, an Antagonistic Therapeutic Agent can be administered in combination with one or more other therapies to suppress an IL-15 mediated immune function. Non-limiting examples of diseases that can be prevented, treated, or managed by suppressing immune function include, but are not limited to, autoimmune disease, inflammatory disorders, graft versus host disease, and transplant rejection.

In a specific embodiment, an Antagonistic Therapeutic Agent suppresses or reduces IL-15 mediated immune function, e.g., NK cell proliferation and cytokine production.

In a specific embodiment, an Antagonistic Therapeutic Agent suppresses IL-15 mediated immune function in a subject (in some embodiments, an animal model) by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the immune function in a subject not administered the Therapeutic Agent using assays well known in the art, e.g., ELISPOT, ELISA, and cell proliferation assays. In a specific embodiment, the immune function is cytokine release or production (e.g., interferon-gamma). In one embodiment, the IL-15 mediated immune function is NK cell proliferation, which can be assayed, e.g., by flow cytometry to detect the number of cells expressing markers of NK cells (e.g., CD56). In one embodiment, the IL-15 mediated immune function is T cell ($CD4^+$ cell and/or $CD8^+$ cell) proliferation and/or activation.

In specific embodiments, an Antagonistic Therapeutic Agent can inhibit or reduce proliferation/expansion of lymphocytes (e.g., number of lymphocytes), induce or increase of apoptosis of lymphocytes, inhibit activation of dendritic cells (or antigen presenting cells), and antigen presentation. In particular embodiments, an immune function suppressed by an Antagonistic Therapeutic Agent is proliferation/expansion/activation of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, dendritic cells (immature or mature), antigen presenting cells, macrophages, mast cells, or natural killer cells. In one embodiment, an Antagonistic Therapeutic Agent decreases/reduces the proliferation/expansion or number of lymphocyte progenitors.

In a specific embodiment, an Antagonistic Therapeutic Agent suppresses IL-15 mediated immune function in a cell-based assay (e.g., assaying proliferation of an IL-15-responsive cell line such at CTLL-2 or TFβ1) by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to a negative control as determined using assays well known in the art, e.g., cell proliferation assays with CSFE, BrdU, and $^3$H-Thymidine incorporation. In a specific embodiment, the immune function is cytokine release (e.g., interferon-gamma). In particular embodiments, the activity of an Antagonistic Therapeutic Agent in cell-based assays and in animal model experiments correlate with the in vivo function of the Antagonistic Therapeutic Agent to suppress IL-15 mediate immune function.

Various autoimmune and inflammatory diseases that can be prevented, treated and/or managed are listed below.

5.4.2.1. Autoimmune and Inflammatory Disorders

The invention provides a method for treating, preventing and/or managing an autoimmune disorder or inflammatory disorder in a subject, comprising administering an effective amount of an. Antagonistic Therapeutic Agent or a composition comprising an Antagonistic Therapeutic Agent to a subject in need thereof. The invention also provides a method for reducing inflammation in a subject, comprising administering an effective amount of an Antagonistic Therapeutic Agent or a composition comprising an Antagonistic Therapeutic Agent to a subject in need thereof. Non-limiting examples of autoimmune disorders and inflammatory disorders include transplant rejection and graft versus host disease (GVHD). GVHD occurs when a donor's immune cells (e.g., donor's T cells) attack cells in the recipient subject's body. Transplant rejection occurs when a transplanted organ or tissue fails to be accepted by the body of the transplant recipient. In general, the transplant rejection is due to the immune system of the recipient (e.g., recipient's T cells) attacking the transplanted organ or tissue.

In a specific embodiment, administering an Antagonistic Therapeutic Agent or composition comprising an Antagonistic Therapeutic Agent to a subject (in some embodiments, an animal model) reduces the inflammation in an subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an subject not administered the Antagonistic Therapeutic Agent using methods known in the art. For example, reduction in inflammation can be measured by the reduction in cytokine secretion (e.g., tumor necrosis factor alpha, interferon gamma). In a specific embodiment, administering an Antagonistic Therapeutic Agent or composition comprising an Antagonistic Therapeutic Agent to a subject (in some embodiments, an animal model) reduces the inflammation in an subject by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to the inflammation in an subject not administered the Antagonistic Therapeutic Agent using methods known in the art. For example, reduction in inflammation can be measured by the reduction cytokine secretion (e.g., tumor necrosis factor alpha, interferon gamma).

In other embodiments, an Antagonistic Therapeutic Agent can be administered in combination with one or more other therapies to suppress IL-15 mediated immune function in a subject. Various anti-inflammatory agents known in the art can be used in combination with Antagonistic Therapeutic Agents.

Examples of autoimmune disorders that can be prevented, treated and/or managed in accordance with the methods described herein include, but are not limited to, celiac (coeliac disease), alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. Some autoimmune disorders are associated with an inflammatory condition. Thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods described herein include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

In some embodiments, Antagonistic Therapeutic Agents, compositions comprising Antagonistic Therapeutic Agents, or combination therapies are administered to a subject suffering from an autoimmune disease or inflammatory disorder. In other embodiments, Antagonistic Therapeutic Agents, compositions comprising Antagonistic Therapeutic Agents, or combination therapies are administered to a subject predisposed or susceptible to developing an autoimmune disease or inflammatory disorder.

In certain embodiments, an Antagonistic Therapeutic Agent, composition comprising an Antagonistic Therapeutic Agent, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, an Antagonistic Therapeutic Agent, composition comprising an Antagonistic Therapeutic Agent, or a combination therapy is administered to a human at risk developing an autoimmune disease or inflammatory disorder. In certain embodiments, an Antagonistic Therapeutic Agent, composition comprising an Antagonistic Therapeutic Agent, or a combination therapy is administered to a human with an autoimmune disease or inflammatory disorder. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, an Antagonistic Therapeutic Agent, composition comprising an Antagonistic Therapeutic Agent, or a combination therapy is administered to a human infant or premature human infant. In other embodiments, an Antagonistic Therapeutic Agent, composition comprising an Antagonistic Therapeutic Agent, or a combination therapy is administered to a human child. In other embodiments, an Antagonistic Therapeutic Agent, composition comprising an Antagonistic Therapeutic Agent, or a combination therapy is administered to a human adult. In yet other embodiments, an Antagonistic Therapeutic Agent, composition comprising an Antagonistic Therapeutic Agent, or a combination therapy is administered to an elderly human.

In certain embodiments, an Antagonistic Therapeutic Agent, composition comprising an Antagonistic Therapeutic Agent, or a combination therapy is administered to a pet, e.g., a dog or cat. In certain embodiments, an Antagonistic Therapeutic Agent, composition comprising an Antagonistic Therapeutic Agent, or a combination therapy is administered to a farm animal or livestock, e.g., pig, cows, horses, chickens, etc.

In certain embodiments, an Antagonistic Therapeutic Agent, composition comprising an Antagonistic Therapeutic Agent, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, an Antagonistic Therapeutic Agent, composition comprising an Antagonistic Therapeutic Agent, or a combination therapy is administered to a subject receiving or recovering from immunosuppressive therapy. In certain embodiments, an Antagonistic Therapeutic Agent, composition comprising an Antagonistic Therapeutic Agent, or a combination therapy is administered to a subject that has or is at risk of getting AIDS, a viral infection, or a bacterial infection. In certain embodiments, a subject that is, will or has undergone surgery, chemotherapy and/or radiation therapy.

In some embodiments, a patient is administered an Antagonistic Therapeutic Agent, composition comprising an Antagonistic Therapeutic Agent, or a combination therapy before any adverse effects or intolerance to therapies other than Antagonistic Therapeutic Agents develops. In some embodiments, Antagonistic Therapeutic Agents, compositions comprising Antagonistic Therapeutic Agents, or combination therapies are administered to refractory patients. In a certain embodiment, refractory patient is a patient refractory to a standard therapy. In certain embodiments, a patient with an autoimmune disease or inflammatory disorder, is refractory to a therapy when the autoimmune disease or inflammatory disorder, respectively, has not significantly been eradicated and/or the symptoms have not been significantly alleviated. The determination of whether a patient is refractory can be made either in vivo or in vitro by any method known in the art for assaying the effectiveness of a treatment, using art-accepted meanings of "refractory" in such a context. In various embodiments, a patient with a inflammatory disorder is refractory when inflammation has not decreased or has increased.

In some embodiments, Antagonistic Therapeutic Agents, compositions comprising Antagonistic Therapeutic Agents, or combination therapies are administered to a patient who are susceptible to adverse reactions to conventional therapies.

In some embodiments, one or more Antagonistic Therapeutic Agents, compositions comprising Antagonistic Therapeutic Agents, or combination therapies are administered to a patient who has proven refractory to therapies other than Antagonistic Therapeutic Agents, but are no longer on these therapies. In certain embodiments, the patients being managed or treated in accordance with the methods described herein are patients already being treated with antibiotics, anti-cancer agents, anti-inflammatory agents, or other biological therapy/immunotherapy. Among these patients are refractory patients, patients who are too young for conventional therapies.

In some embodiments, the subject being administered one or more Antagonistic Therapeutic Agents, compositions comprising Antagonistic Therapeutic Agents, or combination therapies has not received a therapy prior to the administration of the Antagonistic Therapeutic Agents, compositions comprising Antagonistic Therapeutic Agents, or combination therapies. In other embodiments, one or more Antagonistic Therapeutic Agents, compositions comprising Antagonistic Therapeutic Agents, or combination therapies are administered to a subject who has received a therapy prior to administration of one or more Antagonistic Therapeutic Agents, compositions comprising Antagonistic Therapeutic Agents, or combination therapies. In some embodiments, the subject administered an Antagonistic Therapeutic Agent or a composition comprising an Antagonistic Therapeutic Agent was refractory to a prior therapy or experienced adverse side effects to the prior therapy or the prior therapy was discontinued due to unacceptable levels of toxicity to the subject.

5.43. Mode of Administration

Therapeutic Agents can be administered via any route known in the art. In a specific embodiment, Therapeutic Agents formulated with polymers are especially suited for local delivery, but such formulations can also be for systemic administration.

Therapeutic Agents or compositions thereof can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to deliver the Therapeutic Agents or compositions thereof and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, intratumoral, or topically, particularly to the ears, nose, eyes, or skin. The mode of administration is left to the discretion of the practitioner. In some embodiments, administration will result in the release of a Therapeutic Agent into the bloodstream.

In specific embodiments, it may be desirable to administer a Therapeutic Agent locally. This may be achieved, for example, and not by way of limitation, by local infusion, topical application, e.g., in conjunction with a wound dressing, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce a Therapeutic Agent into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

In certain embodiments, a Therapeutic Agent is formulated as a suppository, with traditional binders and vehicles such as triglycerides.

For viral infections or melanoma with cutaneous manifestations, the Therapeutic Agent can be administered topically.

In another embodiment, a Therapeutic Agent is delivered in a vesicle, in particular a liposome (See Langer, 1990, Science 249:1527 1533; Treat et al., in Liposomes in the Therapy of Infectious Disease and Bacterial infection, Lopez-Berestein and Fidler (eds.), Liss, New York, pp. 353 365 (1989); Lopez Berestein, ibid., pp. 317 327).

In another embodiment, a Therapeutic Agent is delivered in a controlled release system (See, e.g., Goodson, in Medical Applications of Controlled Release, supra, vol. 2, pp. 115 138 (1984)). Examples of controlled-release systems are discussed in the review by Langer, 1990, Science 249:1527 1533 may be used. In one embodiment, a pump may be used (See Langer, supra; Sefton, 1987, CRC Crit. Ref. Biomed. Eng. 14:201; Buchwald et at, 1980, Surgery-88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Pappas, 1983, J. Macromnol. Sci. Rev. Macromol. Chem. 23:61; See also Levy or al., 1985, Science 228:190; During et al, 1989, Ann. Neural. 25:351; Howard et al., 1989, J. Neurosurg. 71:105). In a specific embodiment, a controlled-release system comprising a Therapeutic Agent is placed in close proximity to the tissue affected by the disease to be prevented, treated and/or managed. In accordance with this embodiment, the close proximity of the controlled-release system to the affected tissue may result in only a fraction of the dose of the Therapeutic Agent required if it is systemically administered.

In a specific embodiment, the Therapeutic Agent formulated with a polymer is administered locally to the area or tissue of a patient for enhancement or reduction of IL-15 function. In some embodiments, an Agonistic Therapeutic Agent formulated with polymers can be administered locally to a tumor in a cancer patient to enhance or induce IL-15 function and immune response to the tumor. In other embodiments, an Agonistic Therapeutic Agent formulated with polymers can be administered locally to a tissue infected with a pathogen in a subject to enhance or induce IL-15 function and an immune response to the pathogen. In certain embodiments, the Agonistic Therapeutic Agent includes the IL-15/IL-15Ra complex or nucleic acids encoding IL-15 and IL-15Ra. In other embodiments, the Agonistic Therapeutic Agent includes cells expressing IL-15 and IL-15Ra in high amounts and polymers. In one embodiment, high amounts of IL-15/IL-15Ra complexes refer to amounts of IL-15/IL-15Ra complexes expressed by cells that are at least 1 fold, 2 fold, 3 fold, 4 fold, 5 fold, 6 fold, 7 fold, 8 fold, 9 fold, 10 fold, 20 fold, or more than 20 fold higher than amounts of IL-15/IL-15 Ra complexes expressed endogenously by control cells (e.g., cells that have not been genetically engineered to recombinantly express IL-15, IL-15Ra, or both IL-15 and IL-15Ra, or cells comprising an empty vector).

In some embodiments, an Antagonistic Therapeutic Agent formulated with polymers is administered locally to a site of inflammation in a subject suffering from an autoimmune or inflammatory disorder to suppress or reduce IL-15 function and the immune response elicited at the site of inflammation. In other embodiments, an Antagonistic Therapeutic Agent formulated with polymers is administered locally to a site of a transplanted tissue/organ in a subject to suppress or reduce IL-15 function and immune response to the transplanted tissue.

5.4.4. Dosages & Frequency of Administration

The amount of a Therapeutic Agent, or the amount of a composition comprising a Therapeutic Agent, that will be effective in the prevention, treatment and/or management of a disease that is affected by IL-15 function can be determined by standard clinical techniques. In vitro or in vivo assays may optionally be employed to help identify optimal dosage ranges. The precise dose to be employed will also depend, e.g., on the route of administration, the type of symptoms, and the seriousness of the symptoms, and should be decided according to the judgment of the practitioner and each patient's or subject's circumstances.

In some embodiments, the dosage of a Therapeutic Agent or compositions thereof is determined by extrapolating from the no observed adverse effective level (NOAEL), as determined in animal studies. This extrapolated dosage is useful in determining the maximum recommended starting dose for human clinical trials. For instance, the NOAELs can be extrapolated to determine human equivalent dosages (HED). Typically, HED is extrapolated from a non-human animal dosage based on the doses that are normalized to body surface area (i.e., mg/m2). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, See Guidance for Industry Estimating the Maximum Safe Starting Dose in Initial Clinical Trials for Therapeutics in Adult Healthy Volunteers, U.S. Department of Health and Human Services Food and Drug Administration Center for Drug Evaluation and Research (CDER), Pharmacology and Toxicology, July 2005. In one embodiment, a Therapeutic Agent or composition thereof is administered at a dose that is lower than the human equivalent dosage (HED) of the NOAEL over a period of 1 week, 2 weeks, 3 weeks, 1 month, 2 months, three months, four months, six months, nine months, 1 year, 2 years, 3 years, 4 years or more.

In certain embodiments, a dosage regime for a human subject can be extrapolated from animal model studies using the dose at which 10% of the animals die (LD10). In general the starting dose of a Phase I clinical trial is based on preclinical testing. A standard measure of toxicity of a drug in preclinical testing is the percentage of animals that die because of treatment. It is well within the skill of the art to correlate the LD10 in an animal study with the maximal-tolerated dose (MTD) in humans, adjusted for body surface area, as a basis to extrapolate a starting human dose. In some embodiments, the interrelationship of dosages for one animal model can be converted for use in another animal, including humans, using conversion factors (based on milligrams per meter squared of body surface) as described, e.g., in Freireich et al, Cancer Chemother. Rep., 1966, 50:219-244. Body surface area may be approximately determined from height and weight of the patient. See, e.g., Scientific Tables, Geigy Pharmaceuticals, Ardley, N.Y., 1970, 537, In certain embodiments, the adjustment for body surface area includes host factors such as, for example, surface area, weight, metabolism, tissue distribution, absorption rate, and excretion rate. In addition, the route of administration, excipient usage, and the specific disease or virus to target are also factors to consider. In one embodiment, the standard conservative starting dose is about 1/10 the murine LD10, although it may be even lower if other species (i.e., dogs) were more sensitive to the Therapeutic Agent. In other embodiments, the standard conservative starting dose is about 1/100, 1/95, 1/90, 1/85, 1/80, 1/75, 1/70, 1/65, 1/60, 1/55, 1/50, 1/45, 1/40, 1/35, 1/30, 1/25, 1/20, 1/15, 2/10, 3/10, 4/10, or 5/10 of the murine LD10. In other embodiments, an starting dose amount of a Therapeutic Agent in a human is lower than the dose extrapolated from animal model studies. In another embodiment, an starting dose amount of a Therapeutic Agent in a human is higher than the dose extrapolated from animal model studies. It is well within the skill of the art to start doses of the active composition at relatively low levels, and increase or decrease the dosage as necessary to achieve the desired effect with minimal toxicity.

Exemplary doses of Therapeutic Agents comprising polypeptides or antibodies or compositions thereof include milligram or microgram amounts per kilogram of subject or sample weight (e.g., about 1 microgram per kilogram to about 500 milligrams per kilogram, about 5 micrograms per kilogram to about 100 milligrams per kilogram, or about 1 microgram per kilogram to about 50 micrograms per kilogram). In specific embodiments, a daily dose is at least 50 mg, 75 mg, 100 mg, 150 mg, 250 mg, 500 mg, 750 mg, or at least 1 g.

In one embodiment, the dosage is a concentration of 0.01 to 5000 mM, 1 to 300 mM, 10 to 100 mM and 10 mM to 1 µM. In another embodiment, the dosage is a concentration of at least 5 µM, at least 10 µM, at least 50 µM, at least 100 µM, at least 500 µM, at least 1 mM, at least 5 mM, at least 10 mM, at least 50 mM, at least 100 mM, or at least 500 mM.

In one embodiment, the dosage is a concentration of 0.01 to 5000 mM, 1 to 300 mM, 10 to 100 mM and 10 mM to 1 µM. In another embodiment, the dosage is a concentration of at least 5 µM, at least 10 µM, at least 50 µM, at least 100 µM, at least 500 µM, at least 1 mM, at least 5 mM, at least 10 mM, at least 50 mM, at least 100 mM, or at least 500 mM. In a specific embodiment, the dosage is 0.25 µg/kg or more, preferably 0.5 µg/kg or more, 1 µg/kg or more, 2 µg/kg or more, 3 µg/kg or more, 4 µg/kg or more, 5 µg/kg or more, 6 µg/kg or more, 7 µg/kg or more, 8 µg/kg or more, 9 µg/kg or more, or 10 µg/kg or more, 25 µg/kg or more, preferably 50 µg/kg or more, 100 µg/kg or more, 250 µg/kg or more, 500 µg/kg or more, 1 mg/kg or more, 5 mg/kg or more, 6 mg/kg or more, 7 mg/kg or more, 8 mg/kg or more, 9 mg/kg or more, or 10 mg/kg or more of a patient's body weight.

In another embodiment, the dosage is a unit dose of 5 mg, preferably 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 5 mg to about 100 mg, about 100 µg to about 200 µg, about 150 mg to about 300 mg, about 150 mg to about 400 mg, 250 µg to about 500 mg, about 500 mg to about 800 mg, about 500 mg to about 1000 mg, or about 5 mg to about 1000 mg.

Exemplary doses of Therapeutic Agents comprising nucleic acids or compositions thereof include 0.1 µg, 0.5 µg, 1 µg, 1.5 µg, 2 µg, 3 µg, 4 µg, 5 µg, 6 µg, 7 µg, 8 µg, 9 µg, 10 µg, 15 µg, 20 µg, 25 µg, 30 µg, 35 µg, 40 µg, 45 µg, 50 µg, or 60 µgg of nucleic acids per dose. In a specific embodiment, the dose is in the range of 10 ng to 100 mg, or 50 ng to 100 mg, or 100 ng to 100 mg of nucleic acids per dose. In some specific embodiments, the dose is in the range of 10 µg to 100 mg, or 50 µg to 100 mg, or 100 µg to 100 mg, or 100 µg to 100 ng of nucleic acids per dose.

In certain embodiments, suitable dosage ranges for oral administration are about 0.001 milligram to about 500 milligrams of a Therapeutic Agent, per kilogram body weight per day. In specific embodiments, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one Therapeutic Agent is administered, then, in some embodiments, the dosages correspond to the total amount administered. In a specific embodiment, oral compositions contain about 10% to about 95% a Therapeutic Agent by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. In some embodiments, suitable dosage ranges for intranasal administration are about 0.01 µg/kg body weight per day to about 1 mg/kg body weight per day. Suppositories generally contain about 0.01 milligram to about 50 milligrams of a Therapeutic Agent per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 500 milligrams per kilogram of body weight per day. Suitable doses for topical administration include doses that are in the range of about 0.001 milligram to about 50 milligrams, depending on the area of administration.

In another embodiment, a subject is administered one or more doses of a prophylactically or therapeutically effective amount of a Therapeutic Agent or a composition thereof, wherein the prophylactically or therapeutically effective amount is not the same for each dose. In another embodiment, a subject is administered one or more doses of a prophylactically or therapeutically effective amount of a Therapeutic Agent or a composition thereof, wherein the dose of a prophylactically or therapeutically effective amount administered to said subject is increased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 Kg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses. In another embodiment, a subject is administered one or more doses of a prophylactically or therapeutically effective amount of a Therapeutic Agent or composition thereof, wherein the dose is decreased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses.

For Therapeutic Agents comprising cells expressing IL-15 and IL-15Ra in high amounts, the suitable dosage range for administration by any route of administration can be at least 100, 200, 300, 400, 500, 700, 1,000, 5,000, 10,000, 25,000, 50,000, or 100,000 cells. In specific embodiments, the number of cells is at least 100, 200, 300, 400, 500 cells. In other embodiments, the number of cells is at least 300, 400, 500, 700, 1,000 cells. In yet other specific embodiments, the number of cells is at least 700, 1,000, 5,000, 10,000 cells. In some embodiments, the number of cells is at least 5,000, 10,000, 25,000, 50,000, or 100,000 cells. In yet another embodiment, the number of cells is at least 50,000, or 100,000 cells. In other embodiments, the number of cells is at least $1\times10^6$, $5\times10^6$, $1\times10^7$, $5\times10^7$, $1\times10^8$, $5\times10^8$ or more cells. In other embodiments, the number of cells is at least $1\times10^6$, $5\times10^6$, or $1\times10^7$ or more cells. In some embodiments, the number of cells is at least $1\times10^7$, $5\times10^7$, $1\times10^8$ or more cells. In other embodiments, the number of cells is at least $5\times10^7$, $1\times10^8$, $5\times10^8$ or more cells. In specific embodiments, the number of cells is between $1\times10^4$ to $1\times10^6$, $5\times10^4$ to $5\times10^6$, $1\times10^5$ to $1\times10^7$, $1\times10^5$ to $5\times10^8$, $1\times10^6$ to $1\times10^8$, or $1\times10^6$ to $1\times10^7$, or $1\times10^4$ to $1\times10^5$ cells.

In certain embodiments, a subject is administered a Therapeutic Agent or composition thereof in an amount effective to inhibit or reduce symptoms associated with a disease or disorder by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art.

In certain embodiments to treat, a subject is administered a Therapeutic Agent or a composition thereof in an amount effective to inhibit or reduce symptoms associated with a disease or disorder by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or other known to one of skill in the art.

In certain embodiments to treat or manage an infectious disease, a subject is administered an Agonistic Therapeutic Agent or composition thereof in an amount effective to inhibit or reduce replication of an infectious agent by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered an Agonistic Therapeutic Agent or composition thereof in an amount effective to inhibit or reduce replication of an infectious agent by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered an Agonistic Therapeutic Agent or composition thereof in an amount effective to inhibit or reduce replication of an infectious agent by at least 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments to prevent, treat, and/or manage cancer, a subject is administered an Agonistic Therapeutic Agent or composition thereof in an amount effective to inhibit or reduce tumor growth or cancer cell proliferation by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an Agonistic Therapeutic Agent or composition thereof in an amount effective to inhibit or reduce tumor growth or cancer cell proliferation by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments to treat or manage autoimmune or inflammatory diseases, a subject is administered an Antagonistic Therapeutic Agent or composition thereof in an amount effective to suppress or reduce certain aspects of the immune function by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an Antagonistic Therapeutic Agent or composition thereof in an amount effective to suppress or reduce certain aspects of the immune function by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments to, a subject is administered an Agonistic Therapeutic Agent or composition thereof in an amount effective to induce or enhance an immune response by at least 20% to 25%, preferably at least 25% to 30%, at least 30% to 35%, at least 35% to 40%, at least 40% to 45%, at least 45% to 50%/o, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an Agonistic Therapeutic Agent or composition thereof in an amount effective to induce or enhance an immune response by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments to, a subject is administered an Agonistic Therapeutic Agent or composition thereof in an amount effective to increase or enhance the number of lymphocytes (in some embodiments, in a specific target body compartment) by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an Agonistic Therapeutic Agent or composition thereof in an amount effective to increase or enhance the number of lymphocytes (in some embodiments, in a specific target body compartment) by at least 1.5 fold, at least 2 fold, at least 2.5 fold, at least 3 fold, at least 4 fold, at least 5 fold, at least 8 fold, at least 10 fold, at least 15 fold; or at least 20 fold; or by approximately 2 to 5 fold, 2 to 10 fold, 5 to 10 fold, or 5 to 20 fold relative to a negative control as determined using an assay described herein or others known to one of skill in the art. In some embodiments, the specific target body compartment where the number of lymphocytes is increased or enhanced by an Agonistic Therapeutic Agent is the lung, stomach, heart, kidney, liver, small intestines, large intestines, breast, prostate, or bladder. In particular embodiments, the specific target body compartment where the number of lymphocytes is increased or enhanced is the body compartment affected by a disease or disorder (e.g., cancer or infectious disease). In some embodiments, the specific target body compartment where the number of lymphocytes is increased or enhanced is the lymph node, spleen, or peripheral blood.

In certain embodiments, a dose of a Therapeutic Agent or composition thereof is administered to a subject every day, every other day, every couple of days, every third day, once a week, twice a week, three times a week, or once every two weeks. In other embodiments, two, three or four doses of a Therapeutic Agent or composition thereof is administered to a subject every day, every couple of days, every third day, once a week or once every two weeks. In some embodiments, a dose(s) of a Therapeutic Agent or composition thereof is administered for 2 days, 3 days, 5 days, 7 days, 14 days, or 21 days. In certain embodiments, a dose of a Therapeutic Agent or composition thereof is administered for 1 month, 1.5 months, 2 months, 2.5 months, 3 months, 4 months, 5 months, 6 months or more.

The dosages of prophylactic or therapeutic agents which have been or are currently used for the prevention, treatment and/or management of a disease or disorder that is affected by IL-15 function/signaling, e.g., cancer, infectious disease, autoimmune and inflammatory disease, and transplant rejection, can be determined using references available to a clinician such as, e.g., the Physicians' Desk Reference (61st ed. 2007). Preferably, dosages lower than those which have been or are currently being used to prevent, treat and/or manage the disease or disorder are utilized in combination with one or more Therapeutic Agents or compositions thereof.

For agents which have been approved for uses other than prevention, treatment or management of disease or disorder that is affected by IL-15 function/signaling, e.g., cancer, infectious disease, autoimmune and inflammatory disease, and transplant rejection, safe ranges of doses can be readily determined using references available to clinicians, such as e.g., the Physician's Desk Reference (61st ed. 2007).

The above-described administration schedules are provided for illustrative purposes only and should not be considered limiting. A person of ordinary skill in the art will readily understand that all doses are within the scope of the invention.

5.4.5. Additional/Combination Therapy

Other therapies that can be used in combination with Therapeutic Agents (i.e., Agonistic Therapeutic Agents and Antagonistic Therapeutic Agents) for the prevention, treatment and/or management of a disease that is affected by IL-15 function/signaling, e.g., cancer, infectious disease, autoimmune and inflammatory disease, and transplant rejection, include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such therapies include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, and non-steroidal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gangcyclovir, vidarabine, idoxuridine, rifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used or is currently being used for the prevention, management, and/or treatment of a disease that is affected by IL-15 function/signaling can be used in combination with Therapeutic Agents. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M.D. et at (eds.), 17th Ed., Merck Sharp & Dohme Research Laboratories, Rahway, N J, 1999; Cecil Textbook of Medicine, 20th Ed., Bennett and Plum (eds.), W. B. Saunders, Philadelphia, 1996, and Physicians' Desk Reference (61st ed. 2007) for information regarding therapies (e.g., prophylactic or therapeutic agents) which have been or are currently being used for preventing, treating and/or managing disease or disorder that is affected by IL-15 function/signaling, e.g., cancer, infectious disease, autoimmune and inflammatory disease, graft versus host disease, and transplant rejection.

5.4.5.1. Anti-Cancer Agents

Non-limiting examples of one or more other therapies that can be used in combination with a Therapeutic Agent include immunomodulatory agents, such as but not limited to, chemotherapeutic agents and non-chemotherapeutic immunomodulatory agents. Non-limiting examples of chemotherapeutic agents include methotrexate, cyclosporin A, leflunomide, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan. Examples of non-chemotherapeutic immunomodulatory agents include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (MedImmune, Inc., International Publication Nos. WO 02/098370 and WO 02/069904), anti-CD11a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), anti-IL-12 antibodies and anti-IL-23 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, IL-23, TNF-α, TNF-β, interferon (IFN)-α, IFN-β, IFN-γ, and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-α antibodies, and anti-IFN-γ antibodies), and antibodies that immunospecifically bind to tumor-associated antigens (e.g., Herceptin®). In certain embodiments, an immunomodulatory agent is an immunomodulatory agent other than a chemotherapeutic agent. In other embodiments an immunomodulatory agent is an immunomodulatory agent other than a cytokine or hemapoietic such as IL-1, IL-2, IL-4, IL-12, IL-15, TNF, IFN-α, IFN-β, IFN-γ, M-CSF, G-CSF, IL-3 or erythropoietin. In yet other embodiments, an immunomodulatory agent is an agent other than a chemotherapeutic agent and a cytokine or hemapoietic factor.

Non-limiting examples of anti-cancer agents that can be used as therapies in combination with Therapeutic Agents, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofirin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin II derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinarnycin; lenograstim; lentinan sulfate; leptolstatin; letrozole; leukemia inhibiting factor; leukocyte alpha interferon; leuprolide+ estrogen+progesterone; leuprorelin; levanmisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple ttunor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreoide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonennin; sparfosic acid; spicamycin D; spiromustine; splenopentin; spongistatin 1; squalamine; stem cell inhibitor; stem-cell division inhibitors; stipiarnide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In specific embodiments, a anti-cancer agent is not a chemotherapeutic agent.

In other specific embodiments, a Therapeutic Agent can be administered in combination with the administration of one or more therapies such as, but not limited to anti-cancer agents such as those disclosed in Table 1 with standard doses. When used in a combination therapy, the dosages and/or the frequency of administration listed in Table 1 may be decreased.

TABLE 1

| Therapeutic Agent | Dose/Administration/Formulation | | |
|---|---|---|---|
| doxorubicin hydrochloride (Adriamycin RDF ® and Adriamycin PFS ®) | Intravenous | 60-75 mg/m² on Day 1 | 21 day intervals |
| epirubicin hydrochloride (Ellence ™) | Intravenous | 100-120 mg/m² on Day 1 of each cycle or divided equally and given on Days 1-8 of the cycle | 3-4 week cycles |
| fluorousacil | Intravenous | How supplied: 5 mL and 10 mL vials (containing 250 and 500 mg flourouracil respectively) | |
| docetaxel (Taxotere ®) | Intravenous | 60-100 mg/m² over 1 hour | Once every 3 weeks |
| paclitaxel (Taxol ®) | Intravenous | 175 mg/m² over 3 hours | Every 3 weeks for 4 courses (administered sequentially to doxorubicin-containing combination chemotherapy) |
| tamoxifen citrate (Nolvadex ®) | Oral (tablet) | 20-40 mg Dosages greater than 20 mg should be given in divided doses (morning and evening) | Daily |
| leucovorin calcium for injection | intravenous or intramuscular injection | How supplied: 350 mg vial | Dosage is unclear from text. PDR 3610 |
| luprolide acetate Lupron ®) | single subcutaneous injection | 1 mg (0.2 mL or 20 unit mark) | Once a day |
| flutamide (Eulexin ®) | Oral (capsule) | 50 mg (capsules contain 125 mg flutamide each) | 3 times a day at 8 hour intervals (total daily dosage 750 mg) |
| nilutamide (Nilandron ®) | Oral (tablet) | 300 mg or 150 mg (tablets contain 50 or 150 mg nilutamide each) | 300 mg once a day for 30 days followed by 150 mg once a day |
| bicalutamide (Casodex ®) | Oral (tablet) | 50 mg (tablets contain 50 mg bicalutamide each) | Once a day |
| progesterone | Injection | USP in sesame oil 50 mg/mL | |
| ketoconazole (Nizoral ®) | Cream | 2% cream applied once or twice daily depending on symptoms | |
| prednisone | Oral (tablet) | Initial dosage may vary from 5 mg to 60 mg per day depending on the specific disease entity being treated. | |
| estramustine phosphate sodium (Emcyt ®) | Oral (capsule) | 14 mg/kg of body weight (i.e. one 140 mg capsule for each 10 kg or 22 lb of body weight) | Daily given in 3 or 4 divided doses |
| etoposide or VP-16 | Intravenous | 5 mL of 20 mg/mL solution (100 mg) | |
| dacarbazine (DTIC-Dome ®) | Intravenous | 2-4.5 mg/kg | Once a day for 10 days. May be repeated at 4 week intervals |
| polifeprosan 20 with carmustine implant (BCNU) (nitrosourea) (Gliadel ®) | wafer placed in resection cavity | 8 wafers, each containing 7.7 mg of carmustine, for a total of 61.6 mg, if size and shape of resection cavity allows | |
| cisplatin | Injection | [n/a in PDR 861] How supplied: solution of 1 mg/mL in multi-dose vials of 50 mL and 100 mL | |

TABLE 1-continued

| Therapeutic Agent | Dose/Administration/Formulation | | |
|---|---|---|---|
| mitomycin | Injection | supplied in 5 mg and 20 mg vials (containing 5 mg and 20 mg mitomycin) | |
| gemcitabine HCl (Gemzar ®) | Intravenous | For NSCLC-2 schedules have been investigated and the optimum schedule has not been determined 4 week schedule- administration intravenously at 1000 mg/m² over 30 minutes on 3 week schedule- Gemzar administered intravenously at 1250 mg/m² over 30 minutes | 4 week schedule- Days 1, 8 and 15 of each 28-day cycle. Cisplatin intravenously at 100 mg/m² on day 1 after the infusion of Gemzar. 3 week schedule- Days 1 and 8 of each 21 day cycle. Cisplatin at dosage of 100 mg/m² administered intravenously after administration of Gemzar on day 1. |
| carboplatin (Paraplatin ®) | Intravenous | Single agent therapy: 360 mg/m² I.V. on day 1 (infusion lasting 15 minutes or longer) Other dosage calculations: Combination therapy with cyclophosphamide, Dose adjustment recommendations, Formula dosing, etc. | Every 4 weeks |
| ifosamide (Ifex ®) | Intravenous | 1.2 g/m² daily | 5 consecutive days Repeat every 3 weeks or after recovery from hematologic toxicity |
| topotecan hydrochloride (Hycamtin ®) | Intravenous | 1.5 mg/m² by intravenous infusion over 30 minutes daily | 5 consecutive days, starting on day 1 of 21 day course |
| Bisphosphonates Pamidronate Alendronate Risedronate | Intravenous or Oral take with 6-8 oz water. | 60 mg or 90 mg single infusion over 4-24 hours to correct hypercalcemia in cancer patients 5 mg/d daily for 2 years and then 10 mg/d for 9 month to prevent or control bone resorption. 5.0 mg to prevent or control bone resorption. | |
| Lovastatin (Mevacor ™) | Oral | 10-80 mg/day in single or two divided dose. | |

5.4.5.2. Antiviral Agents

Antiviral agents that can be used in combination with Therapeutic Agents include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emnticitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfnavir, ritonavir, and saquinavir. In another embodiment, the antiviral agent is a fusion inhibitor such as enfuvirtide.

Additional, non-limiting examples of antiviral agents for use in combination with Therapeutic Agents include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; avridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

5.4.5.3. Antibacterial Agents

Antibacterial agents, including antibiotics, that can be used in combination with Therapeutic Agents include, but are not limited to, aminoglycoside antibiotics, glycopeptides, amphenicol antibiotics, ansamycin antibiotics, cephalosporins, cephamycins oxazolidinones, penicillins, quinolones, streptogamins, tetracyclins, and analogs thereof. In some embodiments, antibiotics are administered in combination with a Therapeutic Agent to prevent and/or treat a bacterial infection.

In a specific embodiment, Therapeutic Agents are used in combination with other protein synthesis inhibitors, including but not limited to, streptomycin, neomycin, erythromycin, carbomycin, and spiramycin.

In one embodiment, the antibacterial agent is selected from the group consisting of ampicillin, amoxicillin, ciprofloxacin, gentamycin, kanamycin, neomycin, penicillin G, streptomycin, sulfanilamide, and vancomycin. In another embodiment, the antibacterial agent is selected from the group consisting of azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, and trimethoprim.

Additional, non-limiting examples of antibacterial agents for use in combination with Therapeutic Agents include the following: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifamnpin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithomycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o benethamine, penicillin 0, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). Additional examples include cycloserine, mupirocin, tuberin amphomycin, bacitracin, capreomycin, colistin, enduracidin, enviomycin, and 2,4 diaminopyrimidines (e.g., brodimoprim).

5.5. Biological Activity 5.5.1. Assays for Testing the Function of the Therapeutic Agent 5.5.1.1. Cell-Based Assays The invention provides for methods to identify agents that modulate the activity of IL-15/IL-15Ra complexes. The activity of an agent can be assayed with an IL-15 sensitive cell line, e.g., CTLL-2 cells, a mouse cytotoxic T lymphoma cell line (ATCC Accession No. TIB-214) or TF1-β cells. See, e.g., International Publication No. WO 05/085282. For example, to identify antagonists of IL-15 mediated function, proliferation of CTLL-2 or TF1-β cells cultured with an IL-15/IL-15Ra complex in the presence or absence of one or more Antagonist Therapeutic Agents (e.g., antibody) can be assessed by $^3$H-thymidine incorporation assays well known in the art and described in International Publication No. WO 05/085282, which is incorporated by reference herein in its entirety.

To assess the activity of Therapeutic Agents (e.g., polypeptides or nucleic acids encoding IL-15 and/or IL-15Ra and cells expressing those polypeptides) as agonists, proliferation of CTLL-2 or TF1-β cells cultured in the presence or absence of one or more Therapeutic Agents (e.g., IL-15/IL-15Ra complex) can be assessed by $^3$H-thymidine incorporation assays well known in the art and described in International Publication No. WO 05/085282.

Various assays known in the art can be used to assess whether a Therapeutic Agent enhances or suppresses immune function. In one aspect, the Therapeutic Agent increases an immune response that can be, e.g., an antibody response (humoral response) or a cellular immune response, e.g., cytokine secretion (e.g., interferon-gamma), helper activity or cellular cytotoxicity. In one embodiment, the increased immune response is increased cytokine secretion, antibody production, effector function, T cell proliferation, and/or NK cell proliferation. Various assays to measure such activities are well known in the art, and exemplary descriptions of such assays are provided below.

For example, enzyme-linked immunosorbent assays (ELISA) are well known in the art and are described, e.g., in Section 2.1 of Current Protocols in Immunology, Coligan et al. (eds.), John Wiley and Sons, Inc. 1997. ELISA can be used, e.g., to assay the amount or concentration of IL-15 or IL-15Ra polypeptide.

In another method, the "tetramer staining" assay (Altman et al., 1996, Science 274: 94-96) may be used to identify antigen-specific T-cells and to assess how Therapeutic Agents modulate (e.g., enhance or suppress) antigen-specific T cell responses. For example, an MHC molecule containing a specific peptide antigen, such as a tumor-specific antigen, is multimerized to make soluble peptide tetramers and labeled, for example, by complexing to streptavidin. The MHC-peptide antigen complex is then mixed with a population of T cells obtained from a subject administered with an immunogenic composition alone or in combination with a Therapeutic Agent. Biotin is then used to stain T cells which express the tumor-specific antigen of interest.

Furthermore, using the mixed lymphocyte target culture assay, the cytotoxicity of T cells can be tested in a $^{51}$Cr-release assay as described, e.g., in Palladino et al., 1987, Cancer Res. 47:5074-5079. Briefly, the mixed lymphocyte culture is added to a target cell suspension to give different effector:target (E:T) ratios (usually 1:1 to 40:1). The target cells are pre-labeled by incubating 1×10$^6$ target cells in culture medium containing 500 µCi of $^{51}$Cr per ml for one hour at 37° C. The cells are washed three times following labeling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are pelleted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

In another embodiment, an ELISPOT assay can be used to measure cytokine release in vitro by T cells after administration of an effective amount of a Therapeutic Agent to a subject. Cytokine release is detected by antibodies which are specific for a particular cytokine, e.g., interleukin-2, tumor necrosis factor γ or interferon-γ (see, e.g., Scheibenbogen et al., 1997, Int J. Cancer 71:932-936). The assay is carried out in a microtitre plate which has been pre-coated with an antibody specific for a cytokine of interest which captures the cytokine secreted by T cells. After incubation of T cells for 24-48 hours in the coated wells, the T cells are removed and replaced with a second labeled antibody that recognizes a different epitope on the cytokine. After extensive washing to remove unbound antibody, an enzyme substrate which produces a colored reaction product is added to the plate. The number of cytokine-producing cells is counted under a microscope. This method has the advantages of short assay time, and sensitivity without the need of a large number of cytotoxic T cells.

In some aspects, the immune response induced or enhanced by an Agonistic Therapeutic Agent is enhanced or increased by at least 2 fold, 3 fold, 4 fold, 5 fold, 6 fold, 7 fold, 8 fold, 9 fold, 10 fold, 11 fold, or 12 fold relative to an immune response elicited by a negative control as determined by any known assay in the art. In certain embodiments, the immune response induced by the Agonistic Therapeutic Agent is enhanced by at least 0.5-2 times, at least 2-5 times, at least 5-10 times, at least 10-50 times, at least 50-100 times, at least 100-200 times, at least 200-300 times, at least 300-400 times or at least 400-500 times relative to the immune response induced by a negative control as assayed by any known method in the art. In specific embodiments, the assay used to assess immune response measures the level of antibody production, cytokine production, or cellular cytotoxicity, and such assays are well known in the art. In some embodiments, the assay used to measure the immune response is an enzyme-linked immunosorbent assay (ELISA) that determines antibody or cytokine levels, an ELISPOT assay that determines cytokine release, or a $^{51}Cr$ release assay that determines cellular cytotoxicity.

In specific embodiments, the Agonistic Therapeutic Agent induces or enhances an immune response in a subject that is measured by antibody titer in the serum of the subject, and the antibody titer is at least 0.2 to 5 times, 5 to 20 times, 10 to 30 times, 20 to 50 times, 50 to 200 times, 100 to 500, 200 to 1000 times, or 500 to 2,000 times higher as compared to the antibody titer in the serum of a subject administered a negative control. In specific embodiments, the mean serum antibody titer against the antigen in the subject administered the Agonistic Therapeutic Agent is increased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum antibody titer in the subject administered a negative control as determined by methods well known in the art.

In another specific embodiment, the invention provides methods of administering Agonistic Therapeutic Agents to induce or enhance the level of cytokine production or secretion, e.g., interferon-γ, (that may be 0.5 to 500 times higher) as compared to the level of cytokine production or secretion in a negative control sample. In specific embodiments, the Agonistic Therapeutic Agent induces or enhances an immune response that is measured by increased cytokine release, and the cytokine concentration is at least 0.2 to 5 times, 5 to 20 times, 10 to 30 times, 20 to 50 times, 50 to 200 times, 100 to 500, 200 to 1000 times, or 500 to 2,000 times higher as compared to the cytokine concentration of a negative control. In specific embodiments, the mean serum cytokine concentration of samples obtained from a subject administered the Agonistic Therapeutic Agent is increased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum cytokine concentration of samples obtained from a subject administered a negative control as determined by methods well known in the art. In some embodiments, the negative control can be samples from the subject prior to administration of the Agonistic Therapeutic Agent.

In specific embodiments, the Agonistic Therapeutic Agent induces or enhances NK cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to NK cell proliferation in a negative control. In specific embodiments, the Therapeutic Agent induces or enhances T cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to T cell proliferation in a negative control as determined by methods well known in the art, e.g., flow cytometry, CSFE staining, 3H-thymidine incorporation.

The increase in antibody (humoral) or cellular immune response induced by an effective amount of the Therapeutic Agent can be assessed using various methods well known in the art.

For assessing the activity of an Antagonistic Therapeutic Agent that is an antibody that immunospecifically binds to the IL-15/IL-15Ra complex, a cell culture assay can be carried out to determine the ability of the antibody to reduce the binding affinity of the IL-15/IL-15Ra complex to the βγ receptor complex expressed on the surface of cells. Cells that endogenously or recombinantly express the βγ receptor complex can be used in this assay. The cells are contacted with the IL-15/IL-15Ra complex in the presence or absence of the Antagonistic Therapeutic Agent antibody. The IL-15/IL-15Ra complex is labeled with a fluorophore, radioisotope, or other detection markers, and the level of binding of the labeled IL-15/IL-15Ra complex to the βγ receptor complex expressed the cell surface of cells are assayed in the presence and absence of the antibody using methods known in the art, e.g., flow cytometry fluorescent markers, or other compatible machines to detect the detectin marker. In a specific embodiment, the Antagonistic Therapeutic Agent antibody reduces the amount of labeled IL-15/IL-15Ra complexes that bind to the βγ receptor complex on the cell surface.

5.5.1.2. In Vitro Assays

The identification of antibodies that immunospecifically bind to the IL-15/IL-15Ra complex can be assessed using any method well known in the art, e.g., ELISA, coimmunoprecipitation, Biacore assays, and KinEx A assays.

Binding assays can be used to determine the binding affinity of an antibody to IL-15/IL-15Ra complexes. Binding assays may be performed either as direct binding assays or as competition-binding assays. Binding can be detected using standard ELISA or standard Flow Cytometry assays. In a direct binding assay, a candidate antibody is tested for binding to the IL-15/IL-15Ra complex.

Competition-binding assays, on the other hand, assess the ability of a candidate antibody to compete with a known antibodies or other compound that binds IL-15/IL-5Ra complexes.

In a direct binding assay, the IL-15/IL-15Ra complex is contacted with a candidate antibody under conditions that allow binding of the candidate antibody to the IL-15/IL-15Ra complexes. The binding may take place in solution or on a solid surface. Preferably, the candidate antibody is previously labeled for detection. Any detectable compound may be used for labeling, such as but not limited to, a luminescent, fluorescent, or radioactive isotope or group containing same, or a nonisotopic label, such as an enzyme or dye. After a period of incubation sufficient for binding to take place, the reaction is exposed to conditions and manipulations that remove excess or non-specifically bound antibody. Typically, it involves washing with an appropriate buffer. Finally, the presence of a IL-15/IL-15Ra-antibody complex is detected.

In a competition-binding assay, a candidate antibody is evaluated for its ability to inhibit or displace the binding of a known anti-IL-15/IL-15Ra complex antibody (or other compound) to the IL-15/IL-15Ra complex. A labeled known binder of IL-15/IL-15Ra complex may be mixed with the candidate antibody, and placed under conditions in which the interaction between them would normally occur, with and without the addition of the candidate antibody. The amount of labeled known binder of IL-15/IL-15Ra complex that binds the IL-15/IL-15Ra complex may be compared to the amount bound in the presence or absence of the candidate antibody.

In one embodiment, the binding assay is carried out with one or more components immobilized on a solid surface to facilitate antibody antigen complex formation and detection. In various embodiments, the solid support could be, but is not restricted to, polycarbonate, polystyrene, polypropylene, polyethylene, glass, nitrocellulose, dextran, nylon, polyacrylamide and agarose. The support configuration can include beads, membranes, microparticles, the interior surface of a reaction vessel such as a microtiter plate, test tube or other reaction vessel. The immobilization of IL-15/IL-15Ra complex, or other component, can be achieved through covalent or non-covalent attachments. In one embodiment, the attachment may be indirect, i.e., through an attached antibody. In another embodiment, the IL-15/IL-15Ra complex and negative controls are tagged with an epitope, such as glutathione S-transferase (GST) so that the attachment to the solid surface can be mediated by a commercially available antibody such as anti-GST (Santa Cruz Biotechnology).

For example, such an affinity binding assay may be performed using the IL-1/IL-15Ra complex which is immobilized to a solid support. Typically, the non-mobilized component of the binding reaction, in this case the candidate anti-IL-15/IL-15Ra complex antibody, is labeled to enable detection. A variety of labeling methods are available and may be used, such as luminescent, chromophore, fluorescent, or radioactive isotope or group containing same, and nonisotopic labels, such as enzymes or dyes. In one embodiment, the candidate antibody is labeled with a fluorophore such as fluorescein isothiocyanate (FITC, available from Sigma Chemicals, St. Louis). Such an affinity binding assay may be performed using the IL-15/IL-15Ra complex antigen immobilized on a solid surface. Antibodies are then incubated with the antigen and the specific binding of antibodies is detected by methods known in the art including, but not limited to, BiaCore Analyses, ELISA, FMET and RIA methods.

Finally, the label remaining on the solid surface may be detected by any detection method known in the art. For example, if the candidate antibody is labeled with a fluorophore, a fluorimeter may be used to detect complexes.

In one embodiment, the antibody is added to binding assays in the form of intact cells that express IL-15/IL-15Ra complex antigen, or isolated membranes containing IL-15/IL-15Ra complex. Thus, direct binding to IL-15/IL-15Ra complex antigen may be assayed in intact cells in culture or in animal models in the presence and absence of the candidate antibody. A labeled candidate antibody may be mixed with cells that express human IL-15/IL-15Ra complex, or with crude extracts obtained from such cells, and the candidate antibody may be added. Isolated membranes may be used to identify candidate antibodies that interact with IL-15/IL-15Ra complex. For example, in a typical experiment using isolated membranes, cells may be genetically engineered to express IL-15/IL-15Ra complex antigen. Membranes can be harvested by standard techniques and used in an in vitro binding assay. Labeled candidate antibody (e.g., fluorescent labeled antibody) is bound to the membranes and assayed for specific activity; specific binding is determined by comparison with binding assays performed in the presence of excess unlabeled (cold) candidate antibody. Alternatively, soluble IL-15/IL-15Ra complex may be recombinantly expressed and utilized in non-cell based assays to identify antibodies that bind to the IL-15/IL-15Ra complex. The recombinantly expressed IL-15/IL-15Ra polypeptides can be used in the non-cell based screening assays.

Alternatively, the binding reaction may be carried out in solution. In this assay, the labeled component is allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner and so on.

In another specific embodiment, the solid support is membrane containing IL-15/IL-15Ra complex attached to a microtiter dish. Candidate antibodies, for example, can bind cells that express library antibodies cultivated under conditions that allow expression of the library members in the microtiter dish. Library members that bind to the IL-15/IL-15Ra complex are harvested. Such methods, are generally described by way of example in Parrmley and Smith, 1988, Gene, 73:305-318; Fowlkes et al., 1992, BioTechniques, 13:422-427; PCT Publication No. WO94/18318; and in references cited hereinabove.

Various methods described above or known in the art can be adapted to assay the binding affinity of IL-15 derivatives to native IL-15Ra, IL-15Ra derivatives to native IL-15, IL-15 derivatives to IL-15Ra derivatives, and IL-15/IL-15Ra complexes to the f receptor complex.

5.5.2. Animal Models

Therapeutic Agents are preferably assayed in vivo for the desired therapeutic or prophylactic activity prior to use in humans. For example, in one embodiment, a Therapeutic Agent can be administered to the animal at the same time as the onset of a disease or disorder in the animal. In another embodiment, a Therapeutic Agent can be administered to the animal prior to the onset of a disease or disorder in the animal. In another embodiment, a Therapeutic Agent can be administered to the animal subsequent to the onset of a disease or disorder in the animal. In a specific embodiment, the Therapeutic Agent is administered to the animal more than one time. In another specific embodiment, the Therapeutic Agent is administered in combination with another therapy.

Therapeutic Agent can be tested in animal models systems including, but are not limited to, rats, mice, chicken, cows, monkeys, pigs, goats, sheep, dogs, rabbits, guinea pigs, etc. In a specific embodiment, Therapeutic Agents are tested in a mouse model system. Such model systems are widely used and well-known to the skilled artisan.

In certain embodiments, an animal, such as six weeks old female Balb/c mice, are administered nucleic acids encoding IL-15 and IL-15Ra by hydrodynamic injection and the plasma levels of IL-15 and/or the bioactivity of IL-15 is assessed. Briefly, animals (e.g., mice) are injected with the IL-15 plasmid alone or in combination with IL-15Ra plasmid in sterile 0.9% NaCl through their tail vein within 7 seconds using a 27.5 gauge needle. Mice are bled after a certain number of days (e.g., at day 1 and day 3) after injection and the plasma levels of IL-15 are measured using, e.g., an IL-15 chemiluminescent immunoassay (QuantiGlo, R&D systems). After a certain number of days (e.g., 3 days) after injection, mice are sacrificed and liver, lungs, spleen, and mesenteric lymph nodes are collected and analyzed to assess IL-15 bioactivity. To make single cell suspensions, spleens are be gently squeezed through a 100 µm Cell Strainer (Thomas) and washed in RPMI (Gibco) to remove any remaining organ stoma. The cells are resuspended in media (e.g., RPMI containing 10% fetal calf serum (FCS)) and counted using, e.g., Acridine Orange (Molecular Probes)/Ethidium Bromide (Fisher) dye. Lung and liver are minced and incubated with collagenase (Sigma) and DNase (Roche) for a period of time (e.g., 1 hour) at 37° C. to make single cell suspensions. Single cells are collected and resuspended in media (e.g., complete RPMI with 10% FCS). The bioactivity of IL-15 in vivo may be measured in liver, lung and spleen using multicolor Flow Cytometry. Briefly, the cells are washed in FACS buffer containing 0.2% FCS and stained with the following panel of conjugated rat anti-mouse antibodies: CD3-APCCy7, CD4-PerCP, CD8-PECy7, CD44-APC, CD49b-FITC and CD62L-PE (BD Pharmingen). Samples are acquired using FACSAria (BD) and the data is analyzed by FlowJo software (Tree Star, San Carlos, Calif.).

The anti-cancer activity of the Therapeutic Agent can be determined by using various experimental animal models for the study of cancer well known in the art as described in. e.g., Relevance of Tumor Models for Anticancer Drug Development (1999, eds. Fiebig and Burger); Contributions to Oncology (1999, Karger); The Nude Mouse in Oncology Research (1991, eds. Boven and Winograd); and Anticancer Drug Development Guide (1997 ed. Teicher), incorporated herein by reference in their entireties.

Animal models for cancer can be used to assess the efficacy of a Therapeutic Agent, a composition thereof, or a combination therapy comprising a Therapeutic Agent. Non-limiting examples of animal models for lung cancer include, but are not limited to, lung cancer animal models described by Zhang & Roth (1994, In vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCR-β and p53 double knockout mouse (see, e.g., Kado et at, 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ohaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Ape mouse models (see, e.g., Fodde & Smits, 2001, Trends Mol Med 7(8):369-73 and Kuraguchi et al., 2000, Oncogene 19(50):5755-63).

For animal models of infectious diseases, the effectiveness of a Therapeutic Agent relative to a negative control can be assessed in animals infected with virus. Samples obtained from these animals (e.g., serum, urine, sputum, semen, saliva, plasma, or tissue sample) can be tested for enhancement of immune function, e.g., enhancement in cytokine release, enhancement in antibody production, T cell proliferation, NK cell proliferation, with methods well known in the art and described herein. Samples obtained from these animals (e.g., serum, urine, sputum, semen, saliva, plasma, or tissue sample) can also be tested for reduction in viral replication via well known methods in the art, e.g., those that measure altered viral replication (as determined, e.g., by plaque formation) or the production of viral proteins (as determined, e.g., by Western blot, ELISA, or flow cytometry analysis) or viral nucleic acids (as determined, e.g., by RT-PCR, northern blot analysis or southern blot). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody. Non-limiting exemplary animal models described below can be adapted for other viral systems.

Various animal models for infectious diseases that are well known in the art can be employed to assess the efficacy of Therapeutic Agents in preventing, treating, and/or managing infectious diseases, e.g.: mouse models of herpes simplex virus (HSV) are described in Crute et al., Nature Medicine, 2002, 8:386-391 and Bolger et al., Antiviral Res., 1997, 35:157-165; guinea pig models of HSV are described in Chen et al., Virol. J, 2004 Nov. 23, 1:11; animal models of mouse cytomegalovirus (MCMV) and human cytomegalovirus (HCMV) are described in Kern et al., Antimicrob. Agents Chemother., 2004, 48:4745-4753; Guinea pig models of CMV is described in Boume et al., Antiviral Res., 2000, 47:103-109, Bravo et al., Antiviral Res., 2003, 60:41-49 and Bravo et al, J. Infectious Diseases, 2006, 193:591-597; animal models of influenza virus are described in Sidwell et al, Antiviral Res., 2000, 48:1-16; and McCauley et al., Antiviral Res., 1995, 27:179-186; mouse models of hepatitis B virus (HBV) are described in Cavanaugh et al., J. Virol., 1997, 71:3236-3243 and Guidotti et al., J. Virol., 1995, 69:6158-6169; mouse models of hepatitis C virus (HCV) are described in Zhu et al., Antimicrobial Agents and Chemother., 2006, 50:3260-3268, Bright et al., Nature, 2005, 436:973-978, Hsu et al., Nat. Biotechnol., 2003, 21:519-525, Ilan et al., J. Infect. Dis. 2002, 185:153-161, Kneteman et al., Hepatology, 2006, 43:1346-1353, Mercer et al., Nat. Med., 2001, 7:927-933, and Wu et al., Gastroenterology, 2005, 128:1416-1423; animal models of HIV are described in Ayash-Rashkovsky et al., FASEB J., 2005, 19:1149-1151, Mosier et al., Semin. Immunol., 1996, 8:255-262, Mosier et al., Hosp. Pract. (Off Ed)., 1996, 31:41-48, 53-55, 59-60, Bonyhadi et al., Mol. Med. Today, 1997, 3:246-253, Jolicoeur et al., Leukemia, 1999, 13:S78-S80, Browning et al., Proc. Natl. Acad. Sci. USA, 1997, 94:14637-14641, and Sawada et al, J. Exp. Med., 1998, 187:1439-1449, and Schito et al., Curr. HIV Res., 2006, 4:379-386.

Other animal models for viral infections can also be used to assess the efficacy of a Therapeutic Agent, a composition thereof, or a combination therapy comprising a Therapeutic Agent, e.g., animal models for viral infections such as EBV-associated diseases, gammaherpesviruses, infectious mononucleosis, simian immunodeficiency virus ("SIV"), Borna disease virus infection, hepatitis, varicella virus infection, viral pneumonitis, Epstein-Barr virus pathogenesis, feline immunodeficiency virus ("FIV"), HTLV type 1 infection, human rotaviruses, and genital herpes have been developed (see, e.g., Hayashi et al., 2002, Histol Histopathol 17(4): 1293-310; Arico et al., 2002, J Interferon Cytokine Res 22(11):1081-8; Flano et a, 2002, Immunol Res 25(3): 201-17; Sauermann, 2001, Curr Mol Med 1(4):515-22; Pletnikov et al., 2002, Front Biosci 7:d593-607; Engler et al., 2001, Mol Immunol 38(6):457-65; White et al., 2001, Brain Pathol 11(4):475-9; Davis & Matalon, 2001, News Physiol Sci 16:185-90; Wang, 2001, Curr Top Microbiol Immunol. 258:201-19; Phillips et al., 2000, J Psychopharmacol. 14(3):244-50; Kazanji, 2000, AIDS Res Hum Retroviruses. 16(16):1741-6; Saif et al, 1996, Arch Virol Suppl. 12:153-61; and Hsiung et al., 1984, Rev Infect Dis. 6(1): 33-50).

Other animal models for viral respiratory infections include, but not limited to, PIV (see, e.g., Shephard et al, 2003 Res Vet Sci 74(2): 187-190; Ottolini et al., 2002 J Infect Dis 186(12): 1713-1717), and RSV (see, e.g., Culley et al., 2002 J Exp Med 196(10): 1381-1386; and Curtis et al., 2002 Exp Biol Med 227(9): 799-802).

The Therapeutic Agent, composition thereof, or combination therapy comprising the Therapeutic Agent can be tested for their ability to decrease the time course of viral infection.

Animal models for bacterial infections can also be used to assess the efficacy of a Therapeutic Agent, a composition thereof, or a combination therapy comprising a Therapeutic Agent. Animal models for bacterial infections such as *H. pylori*-infection, genital mycoplasmosis, primary sclerosing cholangitls, cholera, chronic lung infection with *Pseudomonas aeruginosa*, Legionnaires' disease, gastroduodenal ulcer disease, bacterial meningitis, gastric *Helicobacter* infection, pneumococcal otitis media, experimental allergic neuritis, leprous neuropathy, mycobacterial infection, endocarditis, *Aeromonas*-associated enteritis, *Bacteroides fragilis* infection, syphilis, streptococcal endocarditis, acute hematogenous osteomyelitis, human scrub typhus, toxic shock syndrome, anaerobic infections, *Escherichia coli* infections, and *Mycoplasma pneumoniae* infections have been developed (see, e.g., Sugiyama et al., 2002, J Gastruenterol. 37 Suppl 13:6-9; Brown et al., 2001, Am J Reprod Immunol. 46(3): 232-41; Vierling, 2001, Best Pract Res Clin Gastroenterol, 15(4):591-610; Kiose, 2000, Trends Microbiol. 8(4):189-91; Stotland et al., 2000, Pediatr Pulmonol. 30(5):413-24; Brieland et al., 2000, Immunophannacology 48(3):249-52; Lee, 2000, Baillieres Best Pract Res Clin Gastroenterol. 14(1): 75-96; Koedel & Pfister, 1999, Infect Dis Clin North Am. 13(3):549-77; Nedrud, 1999, FEMS Immunol Med Microbiol. 24(2):243-50; Prellner et al., 1999, Microb Drug Resist. 5(1):73-82; Vriesendorp, 1997, J Infect Dis. 176 Suppl 2:S164-8; Shetty & Antia, 1996, Indian J Lepr. 68(1):95-104; Balasubramanian et al., 1994, Immunobiology 191(4-5):395-401; Carbon et al., 1994, Int J Biomed Comput. 36(1-2):59-67; Haberberger et al., 1991, Experientia. 47(5):426-9; Onderdonk et al., 1990, Rev Infect Dis. 12 Suppl 2:S169-77; Wicher & Wicher, 1989, Crit Rev Microbiol. 16(3):181-234; Scheld, 1987, J Aitimicrob Chernother. 20 Suppl A:71-85; Emslie & Nade, 1986, Rev Infect Dis. 8(6):841-9; Ridgway et al., 1986, Lab Anim Sci. 36(5):481-5; Quimby & Nguyen, 1985, Crit Rev Microbiol. 12(1):1-44; Onderdonk et al., 1979, Rev Infect Dis. 1(2): 291-301; Smith, 1976, Ciba Found Symp. (42):45-72, and Taylor-Robinson, 1976, Infection. 4(1 Suppl):4-8).

The Therapeutic Agent, composition thereof, or combination therapy comprising the Therapeutic Agent can be tested for their ability to decrease the time course of bacterial infection, e.g., a bacterial respiratory infection by at least 25%, at least 50%, at least 60%, at least 75%, at least 85%, at least 95%, or at least 99% relative to a negative control using methods well known in the art.

The efficacy of Therapeutic Agents, compositions thereof, or combination therapies comprising Therapeutic Agents for the prevention, treatment and/or management of a fungal infection can be assessed in animal models for such infections. Animal models for fungal infections such as *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fimngal peritonitis, *Curvularia geniculata* infection, staphylococcal endophthalmitis, sporotrichosis, and dermatophytosis have been developed (see, e.g., Arendrup at al., 2002, Infection 30(5):286-91; Kamei, 2001, Mycopathologia 152(1):5-13; Guhad at al., 2000, FEMS Microbiol Lett. 192(1):27-31; Yamagata et al., 2000, J Clin Microbiol. 38(9):32606; Andrutis et al., 2000, J Clin Microbiol. 38(6):2317-23; Cock et al., 2000, Rev Inst Med Trop Sao Paulo 42(2):59-66; Shibuya et al, 1999, Microb Pathog. 27(3):123-31; Beers et al., 1999, J Lab Clin Med. 133(5):423-33; Najvar et al., 1999, Antimicrob Agents Chemother.43(2):413-4; Williams et al, 1988, J Infect Dis. 178(4):1217-21; Yoshida, 1988, Kansenshogaku Zasshi. 1998 June; 72(6):621-30; Alexandrakis et al., 1998, Br J Ophthalmol 82(3):306-11; Chakrabarti et al., 1997, J Med Vet Mycol. 35(4):295-7; Martin et al., 1997, Antimicrob Agents Chemother. 41(1):13-6; Chu et al., 1996, Avian Dis. 40(3):715-9; Fidel et al., 1996, J Infect Dis. 173(2): 425-31; Cole et al., 1995, FEMS Microbiol Lett. 15; 126 (2):177-80; Pollock et al., 1995, Nat Genet. 9(2):202-9; Uchida et al., 1994, Jpn J Antibiot. 47(10):1407-12; Maebashi et al., 1994, J Med Vet Mycol. 32(5):349-59; Jensen &

Schonheyder, 1993, J Exp Anima Sci. 35(4):155-60; Gokaslan & Anaissie, 1992, Infect Immun. 60(8):3339-44; Kurup et al., 1992, J Immunol. 148(12):3783-8; Singh et al., 1990, Mycopathologia. 112(3):127-37; Salkowski & Balish, 1990, Infect Immun, 58(10):3300-6; Ahmad et al., 1986, Am J Kidney Dis. 7(2):153-6; Alture-Werber E, Edberg S C, 1985, Mycopathologia. 89(2):69-73; Kane et al., 1981, Antimicrob Agents Chemother. 20(5):595-9; Barbee et al., 1977, Am J Pathol. 86(1):281-4; and Maestrone et al., 1973, Am J Vet Res. 34(6):833-6). Animal models for fungal respiratory infections such as *Candida albicans, Aspergillus fumigatus*, invasive pulmonary aspergillosis, *Pneumocystis carinii*, pulmonary cryptococcosis, *Pseudomonas aeruginosa, Cunninghamella bertholletia* (see, e.g., Aratani et al., 2002 Med Mycol 40(6):557-563; Bozza et al., 2002 Microbes Infect 4(13): 1281-1290; Kurup et al., 2002 Int Arch Allergy Immunol 129(2):129-137; Hori et al., 2002 Eur J Immuno 32(5): 1282-1291; Rivera et al., 2002 J Immuno 168(7): 3419-3427; Vassallo et al., 2001, Am J Respir Cell Mol Biol 25(2): 203-211; Wilder et al., 2002 Am J Respir Cell Mol Biol 26(3): 304-314; Yonezawa et al., 2000 J Infect Chemother 6(3): 155-161; Cacciapuoti et al., 2000 Antimicrob Agents Chemother 44(8): 2017-2022; and Honda et al., 1998 Mycopathologia 144(3):141-146).

The Therapeutic Agents, compositions thereof, or combination therapies comprising Therapeutic Agents can be tested for their ability to decrease the time course of fungal respiratory infection by at least 25%, at least 50%, at least 60%, at least 75%, at least 85%, at least 95%, or at least 99%. Techniques known to those of skill in the art can be used to analyze the function of the Therapeutic Agents, compositions thereof, or combination therapies comprising Therapeutic Agents in vivo.

Animal models for autoimmune disorders can also be used to assess the efficacy of a Therapeutic Agent, composition thereof, or combination therapy comprising a Therapeutic Agent. Animal models for autoimmune disorders such as type 1 diabetes, thyroid autoimmunity, systemic lupus erythematosus, and glomerulonephritis have been developed (Flanders et al., 1999, Autoimmunity 29:235-246; Krogh et al., 1999, Biochimie 81:511-515; Foster, 1999, Semin. Nephrol. 19:12-24).

Efficacy in preventing, treating and/or managing an autoimmune disorder may be demonstrated, e.g., by detecting the ability of an antibody, a composition, or a combination therapy described herein to reduce one or more symptoms of the autoimmune disorder, to reduce mean absolute lymphocyte counts, to decrease T cell activation, to decrease T cell proliferation, to reduce cytokine production, or to modulate one or more particular cytokine profiles. Efficacy in preventing or treating psoriasis may be demonstrated, e.g., by detecting the ability of a Therapeutic Agent or composition thereof to reduce one or more symptoms of psoriasis, to reduce mean absolute lymphocyte counts, to reduce cytokine production, to modulate one or more particular cytokine profiles, to decrease scaling, to decrease erythema, to decrease plaque elevation, to decrease T cell activation in the dermis or epidermis of an affected area, to decrease T cell infiltration to the dermis or epidermis of an affected area, to reduce PASI, to improve the physician's global assessment score, or to improve quality of life.

The anti-inflammatory activity of a Therapeutic Agent, a composition thereof, or a combination therapy comprising a Therapeutic Agent can be determined by using various experimental animal models of inflammatory arthritis known in the art and described in Crofford L. J. and Wilder R. L., "Arthritis and Autoimmunity in Animals," in Arthritis and Allied Conditions: A Textbook of Rheumatology, McCarty (eds.), Chapter 30 (Lee and Febiger, 1993). Experimental and spontaneous animal models of inflammatory arthritis and autoimmune rheumatic diseases can also be used to assess the anti-inflammatory activity of the Therapeutic Agents, compositions thereof, or combination therapies comprising Therapeutic Agents.

The anti-inflammatory activity of a Therapeutic Agent, a composition thereof, or a combination therapy comprising a Therapeutic Agent can also be assessed by measuring the inhibition of carrageenan-induced paw edema in the rat, using a modification of the method described in Winter C. A. et al., "Carrageenan Induced Edema in Hind Paw of the Rat as an Assay for Anti-inflammatory Drugs" Proc. Soc. Exp. Biol Med. 111, 544-547, (1962). This assay has been used as a primary in vivo screen for the anti-inflammatory activity of most NSAIDs, and is considered predictive of human efficacy. The anti-inflammatory activity of the test therapies (e.g., The Therapeutic Agents, compositions thereof, or combination therapies comprising Therapeutic Agents) is expressed as the percent inhibition of the increase in hind paw weight of the test group relative to the vehicle dosed control group.

In a specific embodiment where the experimental animal model used is adjuvant-induced arthritis rat model, body weight can be measured relative to a control group to determine the anti-inflammatory activity of a Therapeutic Agent, a composition thereof, or a combination therapy.

Animal models for allergies and asthma are known in the art, such as constant-flow inflation with end-inspiratory occlusion described in Ewart et al., 1995 J. Appl Physiol 79(2):560-566 and other assays described in, e.g., Komai et al., 2003 Br J Pharmacol 138(5): 912-920; Kenyon et al., 2003 Toxicol Appl Pharmacol 186(2): 90-100; Path et al., 2002 Am J Resp & Critical Care Med 166(6): 818-826; Martins et al., 1990 Crit Care Med 19:515-519; Nicolaides et al., 1997 Proc Natl Acad Sci USA 94:13175-13180; McLane et al., 1998 19:713-720; and Temann et al., 1998 J. Exp Med 188(7): 1307-1320. For example, the murine adoptive transfer model is an animal model used to assess the efficacy a Therapeutic Agent, a composition thereof, or a combination therapy for the prevention, treatment, management, and/or asthma include. In the murine adoptive transfer model, aeroallergen provocation of TH1 or TH2 recipient mice results in TH effector cell migration to the airways and is associated with an intense neutrophilic (TH1) and eosinophilic (TH2) lung mucosal inflammatory response (Cohn et al, 1997, J. Exp. Med. 1861737-1747). Airway hypersensitivity can be induced in mice by ovalbumin (Tomkinson et al., 2001, J. Immunol. 166:5792-5800) or *Schistosoma mansoni* egg antigen (Tesciuba el at, 2001, J. Immunol. 167:1996-2003).

Efficacy in preventing or treating an inflammatory disorder may be demonstrated, e.g., by detecting the ability of a Therapeutic Agent, a composition thereof, or a combination therapy comprising a Therapeutic Agent to reduce one or more symptoms of the inflammatory disorder, to decrease T cell activation, to decrease T cell proliferation, to modulate one or more cytokine profiles, to reduce cytokine production, to reduce inflammation of a joint, organ or tissue or to improve quality of life.

Changes in inflammatory disease activity may also be assessed through tender and swollen joint counts, patient and physician global scores for pain and disease activity, and the ESRICRP. Progression of structural joint damage may be assessed by quantitative scoring of X-rays of hands, wrists, and feet (Sharp method). Changes in functional status in humans with inflammatory disorders may be evaluated using the Health Assessment Questionnaire (HAQ), and quality of life changes are assessed with the SF.

The efficacy of a Therapeutic Agent, a composition thereof, or a combination therapy comprising a Therapeutic Agent in preventing, treating and/or managing Type 1 allergic reaction may be assessed by its ability to induce anti-IgE antibodies that inhibit IgE from binding to is receptor on mast cells or basophils in vitro. IgE levels can be assayed by immunoassays, gel electrophoresis followed by visualization, radioimmunosorbent test (RIST), radioallergosorbent test (RAST), or any other method known to those skilled in the art.

5.5.3. Toxicity

The toxicity and/or efficacy of the prophylactic and/or therapeutic protocols described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any therapy used in the method, e.g., as described herein, the therapeutically effective dose can be estimated initially from cell culture assays. A dose may be formulated in animal models to achieve a circulating plasma concentration range that includes the IC50 (i.e., the concentration of the Therapeutic Agent that achieves a half-maximal inhibition of symptoms) as determined in cell culture. Such information can be used to more accurately determine useful doses in humans. Levels in plasma may be measured, for example, by high performance liquid chromatography.

In yet another embodiment, apoptotic cells are measured in both the attached and "floating" compartments of the cultures. Both compartments are collected by removing the supernatant, trypsinizing the attached cells, and combining both preparations following a centrifugation wash step (10 minutes, 2000 rpm).

In yet another embodiment, apoptosis is quantitated by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34 37 (Roche Molecular Biochemicals).

In yet another embodiment, apoptosis can be observed morphologically.

Cell lines on which such assays can be performed are well known to those of skill in the art. Apoptosis, necrosis and proliferation assays can also be performed on primary cells, e.g., a tissue explant.

6. EXAMPLES

Human 293 cells were transfected with nucleic acid expression construct for IL-15 (see, e.g., FIG. 5A-D) alone or in combination with a nucleic acid expression construct for IL-15sRa (see, e.g., FIG. 7A-D) or IL-15Ra (see, e.g., FIG. 6A-D) together with a plasmid conferring hygromycin resistance. IL15tPA indicates the optimized nucleic acid expression construct having the tPA prepro peptide (i.e., signal peptide) replacing the natural IL-15 secretory signal. "Ra" and "sRa" indicate the optimized expression vectors used for expression of the full-length IL-15Ra and the extracellular portion of IL-15Ra (soluble form), respectively. Transfected cells were treated with hygromycin (250 µg/ml), and rapidly growing resistant cell foci were isolated and expanded. Supernatants of the different clones were assayed for IL-15 expression after 2 days in culture by ELISA (R&D Systems Quantikine human IL-5 Elisa kit). IL-15 production is higher in cells receiving both genes (p=0.0166). Two measurements of IL-15 were determined for most clones.

TABLE 2

| IL-15/million cells (ng/ml) | clone# | genes |
|---|---|---|
| 9.2 | 3.1 | IL15tPA |
| 14.0 | 3.1 | IL15tPA |
| 37.7 | 3.3 | IL15tPA |
| 74.0 | 3.3 | IL15tPA |
| 147.2 | 7.5 | IL15tPA + sRA |
| 136.8 | 6.4 | IL15tPA + sRA |
| 266.2 | 6.4 | IL15tPA + sRA |
| 135.9 | 6.5 | IL15tPA + sRA |
| 133.8 | 6.5 | IL15tPA + sRA |
| 184.1 | 6.8 | IL15tPA + sRA |
| 192.7 | 6.8 | IL15tPA + sRA |
| 37.5 | 6.9 | IL15tPA + sRA |
| 37.8 | 6.9 | IL15tPA + sRA |
| 101.3 | 7.2 | IL15tPA + sRA |
| 176.0 | 7.2 | IL15tPA + sRA |
| 294.5 | 7.21 | IL15tPA + sRA |
| 390.0 | 7.21 | IL15tPA + sRA |
| 81.2 | 4.2 | IL15tPA + RA |
| 194.2 | 4.2 | IL15tPA + RA |
| 54.0 | 4.4 | IL15tPA + RA |
| 100.8 | 4.4 | IL15tPA + RA |
| 18.3 | 5.6 | IL15tPA + RA |
| 46.2 | 5.6 | IL15tPA + RA |
| 31.2 | 5.2 | IL15tPA + RA |
| 22.5 | 5.2 | IL15tPA + RA |

Clone 7.21 was further cultured and selected for the ability to grow in serum-free medium in shake flasks and selected for cells with the ability to grow under such conditions. Briefly, the clones were cultured at a 1:1 medium ratio of old (10% fetal calf serum) to new media (serum-free) until two population doublings were observed. This procedure was repeated until cells that could be grown well in serum free medium were obtained. The serum free medium used was a 1:1 mix of 2 commercial media: (i) HyClone HyQ SFM4HEK293 (cat. #SH30521.02) and (ii) Invitrogen FreeStyle 293 (cat. #12338-026). The typical yield of recombinant IL-15 produced by cells adapted to grow in serum-free medium in shake flasks from clone 7.21 is approximately 3 to 4 mg/L of medium and 0.6 µg/$10^6$ cells as measured by ELISA (R&D Systems, Quantikine human IL-15 ELISA kit).

7. SPECIFIC EMBODIMENTS, CITATION AND REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein; the disclosure of each such reference is hereby incorporated herein by reference in its entirety.

What is claimed is:

1. A method of recombinantly producing a human IL-15 and a human IL-15Ra complex, comprising:
   (a) culturing a cell expressing a human IL-15 encoded by a nucleic acid sequence with at least 95% identity to nucleic acid residues 1 to 489 of SEQ ID NO:2; and a human IL15Ra encoded by: (i) a nucleic acid sequence with at least 95% identity to nucleic acid residues 1 to 804 of SEQ ID NO:5; or (ii) a nucleic acid sequence with at least 95% identity to nucleic acid residues 1 to 615 of SEQ ID NO:6 and
   (b) purifying the human IL-15 and human IL-15Ra complex,
   wherein the cell expresses at least 150 ng/million cells of human IL-15 per day when cultured in serum-free media.

2. The method of claim 1, wherein the human IL-15 is encoded by the nucleic acid sequence comprising nucleic acid residues 1 to 489 of SEQ ID NO:2; and the human IL15Ra is encoded by the nucleic acid sequence comprising nucleic acid residues 1 to 804 of SEQ ID NO:5.

3. The method of claim 1, wherein the human IL-15 is encoded by the nucleic acid sequence comprising nucleic acid residues 1 to 489 of SEQ ID NO:2; and the human IL15Ra is encoded by the nucleic acid sequence comprising nucleic acid residues 1 to 615 of SEQ ID NO:6.

4. The method of claim 1, wherein the cell is selected from the group consisting of: 293, COS, CHO, HeLa, NIH3T3, HepG2, MCF7, RD, PC12, K562, skBr3, BT274, A204, MO7Sb, TFB I, Raji, Jurkat, MOLT-4, CTLL-2, MC-IXC, SK-N-MC, SK-N-DZ, SH-SYSSY, C I27 and BE(2)-C cell line.

* * * * *